US006607880B1

(12) United States Patent
Shore et al.

(10) Patent No.: US 6,607,880 B1
(45) Date of Patent: Aug. 19, 2003

(54) METHODS AND REAGENTS FOR MODULATING APOPTOSIS

(75) Inventors: Gordon C. Shore, Quebec (CA); Florence W. H. Ng, Quebec (CA); Mai Nguyen, Quebec (CA); Philip E. Branton, Quebec (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/033,524

(22) Filed: Mar. 2, 1998

(30) Foreign Application Priority Data

Mar. 3, 1997 (CA) .............................................. 2198988

(51) Int. Cl.[7] .......................... C12Q 1/68; G01N 33/53; G01N 33/566
(52) U.S. Cl. .............................. 435/6; 435/7.8; 436/501
(58) Field of Search ....................... 435/6, 9.8; 436/501

(56) References Cited

U.S. PATENT DOCUMENTS 5,283,173 A * 2/1994 Fields et al. .................... 435/6

OTHER PUBLICATIONS

Callard et al. The Cytokine Facts Book. New York:Academic Press. p. 31, 1987.*
Florence W.H. Ng et al., "P28 Bap31, a Bcl–2/Bcl–$X_L$–and Procaspase–8–associated protein in the endoplasmic reticulum," Journal of Cell Biology 139: 327–338, 1997.
Ng and Shore, "Bcl–$X_L$ cooperatively associates with the Bap31 complex in the endoplasmic reticulum, dependent on procaspase–8 and Ced–4 Adaptor," The Journal of Biological Chemistry 273: 3140–3143, 1998.

Nguyen et al., "Role of Membrane Anchor Domain of Bcl–2 in Suppression of Apoptosis Caused by E1B–defective Adenovirus," J. Biol. Chem. 269: 16521–16524, 1994.
Teodoro et al., "Adenovirus E1A proteins induce apoptosis by both p53–dependent and p53–independent mechanisms," Oncogene 11: 467–474, 1995.
GenBank accession No. X81817. Aug. 9, 1996.
GenBank accession No. Z31696. Jun. 28, 1995.
Kim et al., "Two new proteins preferentially associated with membrane immunoglobulin D," EMBO J. 13:3793–3800, 1994.
Adachi et al., "The specificity of association of the IgD molecule with the accessory proteins BAP31/BAP29 lies in the IgD transmembrane sequence," EMBO J. 15: 1534–1541, 1996.
Chinnayan et al., "Interaction of CED–4 with CED–3 and CED–9: A Molecular Framework for Cell Death," Science 275: 1122–1126, 1997.
Annaert et al., "Export of cellubrevin from the endoplasmic reticulum is controlled by BAP31," J. Cell Biol.139: 1397–1410, 1997.

* cited by examiner

*Primary Examiner*—Gabrielle Bugaisky
(74) *Attorney, Agent, or Firm*—Clark & Elbing LLP; Kristina Bieker-Brady

(57) ABSTRACT

The invention provides a novel apoptosis protein: p28 Bap31. Also provided are p28 Bap31 polypeptide fragments, p28 Bap31 antisense nucleic acid molecules, anti-p28 Bap31 antibodies, and methods for modulating apoptosis and for detecting compounds which modulate apoptosis.

21 Claims, 20 Drawing Sheets

```
                                  TM1
  1    MTLQWT AVATFLYAĚVFVVLLLCIPFI SPK

TM2
 31    RWQKIFKSRLVE LLVSYGNTFFVVLIVILV

61    LLVI DAVREIRKYDDVTEKVNLQNNPGAME
                          TM3
 91    HFHMKLFRAQR NLYIAGFSLLLSFLLR̈RLV

121    TLI SQQATLLASNEAFKKQAESASEAAKKY
                        ↓
151    MEENDQLKKGAAVDGGKLDVGNAEVKLEEE

181    NRSLKAD*L*QKLKDE*L*ASTKQK*L*EKAENEVL
                                       ↓
211    A*M*RKQSEG*L*TKEYDR*L*LEEHAK*LQ***AAVDG***P

241    MDKKEE    (SEQ ID NO: 1)
``` p28 / BAP31 / CDM

Fig. 2C

| | | (SEQ ID NO:4) |
| Human BAP31 (124-168) | SQQATLLASNEAFKKQAESASEAAKKYMEENDQLKKGAAVDGGKL | (SEQ ID NO:5) |
| Mouse BAP31 (124-168) | SQQATLLASNEAFKKQAESASEAAKKYMEENDQLKKGAAEDGGKL | |

| | | |
|---|---|---|
| Human BAP31 (169-231) | DVGNAEVKIEEENRSIK-ADIQKIK----DELASTIQKLEKAENEVIAMRKQSEGIIKEYDRIIEIEHA | (SEQ ID NO:6) |
| Mouse BAP31 (169-230) | DIGNTEMKII--EENKSIK-NDIRKEK----DELASTIKKLEKAENEAIAMQKQSEGIIKEYDRIIEIEHA | (SEQ ID NO:7) |
| Human FLICE (97-164) | QISARVMLYQISEEVSRSEIRSEMLLQEEISKCLIDDMNLIDIIEMEKRVIIEGKIDIKRVC | (SEQ ID NO:13) |
| Human Mch4 (111-174) | RVSLIRNIIYEISEGIDSENIKDMITILKDISLRK----TEMTSLSEIAFIEEKQGKIIEDNITCLEIDIC | (SEQ ID NO:31) |
| Human PEA15 (1-67) | -MVEIGTSIIQDLTNNITLEDIEQIKSAIKIDISEIISEEFITTGSAWIESFIESHNKIIDKDNESIIEHII | (SEQ ID NO:8) |
| Mouse PEA15 (1-67) | -MAEIGTLIIQDLTNNITLEDIFEQIKSAIKIDIISEIISEKSEEFITTGSAWESFIESHNKIIDKDNLSVIEHII | (SEQ ID NO:9) |
| Human FADD (1-67) | -MDPIILVIEIISHSVSSSSESSSEIITEIEAKILGRIVGKRIILERIIVQSGIDLISMILEQNDIEPGHTEIIRIIII | (SEQ ID NO:10) |
| Mouse FADD (1-67) | -MDPELVLIIHSLSGSIISGNDIIMEKIIOLIIGRTRVSKRIILERVQSGIDIITVILEQNDIERGHTGIERIDIL | (SEQ ID NO:11) |
| Human FLICE (1-66) | -MD--IESRNIYDIGEQEIDSEDLASIIKIILSLDIYIIRQRKQEPIKDALMIIQRIQEKRMIIESNIISIIEKEII | (SEQ ID NO:12) |
| Human Mch4 (16-83) | CKVSIFREKILIIDSNIIGVQIVENIIKFLIIGLIAPNKKLEKSSSASIVIEHIILAEDLISEEDPFFLAIELII | (SEQ ID NO:32) |

| | | |
|---|---|---|
| Human BAP31 (232-246) | KLQAAVDGPMDKKEE | (SEQ ID NO:14) |
| Mouse BAP31 (231-245) | KLQASVRGPSVKKEE | (SEQ ID NO:15) |

Fig. 2D

```
MSLQWTTVAT FLYAEVFAVL LLCIPFISPK RWQKVFKSRL VELVVTYGNT
FFVVLIVILV LLVIDAVREI LKYDDVTEKV NLQNNPGAME HFHMKLFRAQ
RNLYIAGLSL LLSFLLRRLV TLISQQATLL ASNEAFKKQA ESASEAAKKY
MEENDQLKKG AAEDGDKLDI GNTEMKLEEN KSLKNDLRKL KDELASTKKK
LEKAENEALA MQKQSEGLTK EYDRLLEEHA KLQASVRGPS VKKEE
```

Fig. 2E

SEQUENCE LISTING

<160> NUMBER OF SEQ ID NOS: 33

<210> SEQ ID NO 1
<211> LENGTH: 246
<212> TYPE: PRT
<213> ORGANISM: Homo sapiens

<400> SEQUENCE: 1

```
Met Thr Leu Gln Trp Thr Ala Val Ala Thr Phe Leu Tyr Ala Glu Val
 1               5                  10                  15

Phe Val Val Leu Leu Leu Cys Ile Pro Phe Ile Ser Pro Lys Arg Trp
            20                  25                  30

Gln Lys Ile Phe Lys Ser Arg Leu Val Glu Leu Leu Val Ser Tyr Gly
        35                  40                  45

Asn Thr Phe Phe Val Val Leu Ile Val Ile Leu Val Leu Leu Val Ile
    50                  55                  60

Asp Ala Val Arg Glu Ile Arg Lys Tyr Asp Asp Val Thr Glu Lys Val
65                  70                  75                  80

Asn Leu Gln Asn Asn Pro Gly Ala Met Glu His Phe His Met Lys Leu
                85                  90                  95

Phe Arg Ala Gln Arg Asn Leu Tyr Ile Ala Gly Phe Ser Leu Leu Leu
            100                 105                 110

Ser Phe Leu Leu Arg Arg Leu Val Thr Leu Ile Ser Gln Gln Ala Thr
        115                 120                 125

Leu Leu Ala Ser Asn Glu Ala Phe Lys Lys Gln Ala Glu Ser Ala Ser
    130                 135                 140

Glu Ala Ala Lys Lys Tyr Met Glu Glu Asn Asp Gln Leu Lys Lys Gly
```

-continued

```
            145                 150                 155                 160
Ala Ala Val Asp Gly Gly Lys Leu Asp Val Gly Asn Ala Glu Val Lys
                    165                 170                 175

Leu Glu Glu Asn Arg Ser Leu Lys Ala Asp Leu Gln Lys Leu Lys
                180                 185                 190

Asp Glu Leu Ala Ser Thr Lys Gln Lys Leu Glu Lys Ala Glu Asn Glu
                195                 200                 205

Val Leu Ala Met Arg Lys Gln Ser Glu Gly Leu Thr Lys Glu Tyr Asp
        210                 215                 220

Arg Leu Leu Glu Glu His Ala Lys Leu Gln Ala Ala Val Asp Gly Pro
225                 230                 235                 240

Met Asp Lys Lys Glu Glu
                245
```

<210> SEQ ID NO 2
<211> LENGTH: 5
<212> TYPE: PRT
<213> ORGANISM: Homo sapiens

<400> SEQUENCE: 2

```
Ala Ala Val Asp Gly
1               5
```

<210> SEQ ID NO 3
<211> LENGTH: 4
<212> TYPE: PRT
<213> ORGANISM: Artificial Sequence
<220> FEATURE:
<221> NAME/KEY: VARIANT
<222> LOCATION: (1)...(4)
<223> OTHER INFORMATION: Xaa = Any Amino Acid
<220> FEATURE:
<223> OTHER INFORMATION: based on Homo sapiens

<400> SEQUENCE: 3

```
Lys Lys Xaa Xaa
1
```

<210> SEQ ID NO 4
<211> LENGTH: 45
<212> TYPE: PRT
<213> ORGANISM: Homo sapiens

<400> SEQUENCE: 4

```
Ser Gln Gln Ala Thr Leu Leu Ala Ser Asn Glu Ala Phe Lys Lys Gln
1               5                   10                  15

Ala Glu Ser Ala Ser Glu Ala Ala Lys Lys Tyr Met Glu Glu Asn Asp
                20                  25                  30

Gln Leu Lys Lys Gly Ala Ala Val Asp Gly Gly Lys Leu
            35                  40                  45
```

<210> SEQ ID NO 5
<211> LENGTH: 45
<212> TYPE: PRT
<213> ORGANISM: Mus musculus

<400> SEQUENCE: 5

```
Ser Gln Gln Ala Thr Leu Leu Ala Ser Asn Glu Ala Phe Lys Lys Gln
1               5                   10                  15

Ala Glu Ser Ala Ser Glu Ala Ala Lys Lys Tyr Met Glu Glu Asn Asp
                20                  25                  30
```

```
Gln Leu Lys Lys Gly Ala Ala Glu Asp Gly Asp Lys Leu
        35                  40                  45

<210> SEQ ID NO 6

<211> LENGTH: 63
<212> TYPE: PRT

<213> ORGANISM: Homo sapiens

<400> SEQUENCE: 6

Asp Val Gly Asn Ala Glu Val Lys Leu Glu Glu Asn Arg Ser Leu
 1               5                  10                  15

Lys Ala Asp Leu Gln Lys Leu Lys Asp Glu Leu Ala Ser Thr Lys Gln
                20                  25                  30

Lys Leu Glu Lys Ala Glu Asn Glu Val Leu Ala Met Arg Lys Gln Ser
                35                  40                  45

Glu Gly Leu Thr Lys Glu Tyr Asp Arg Leu Leu Glu Glu His Ala
        50                  55                  60

<210> SEQ ID NO 7
<211> LENGTH: 62

<212> TYPE: PRT
<213> ORGANISM: Mus musculus

<400> SEQUENCE: 7

Asp Ile Gly Asn Thr Glu Met Lys Leu Glu Glu Asn Lys Ser Leu Lys
 1               5                  10                  15

Asn Asp Leu Arg Lys Leu Lys Asp Glu Leu Ala Ser Thr Lys Lys
                20                  25                  30

Leu Glu Lys Ala Glu Asn Glu Ala Leu Ala Met Gln Lys Gln Ser Glu
                35                  40                  45

Gly Leu Thr Lys Glu Tyr Asp Arg Leu Leu Glu Glu His Ala
        50                  55                  60

<210> SEQ ID NO 8

<211> LENGTH: 67
<212> TYPE: PRT
<213> ORGANISM: Homo sapiens

<400> SEQUENCE: 8

Met Val Glu Tyr Gly Thr Leu Phe Gln Asp Leu Thr Asn Asn Ile Thr
 1               5                  10                  15

Leu Glu Asp Leu Glu Gln Leu Lys Ser Ala Cys Lys Glu Asp Ile Pro
                20                  25                  30

Ser Glu Lys Ser Glu Glu Ile Thr Thr Gly Ser Ala Trp Phe Ser Phe
                35                  40                  45

Leu Glu Ser His Asn Lys Leu Asp Lys Asp Asn Leu Ser Ile Ile Glu
        50                  55                  60

His Ile Phe
65

<210> SEQ ID NO 9
<211> LENGTH: 67
<212> TYPE: PRT
<213> ORGANISM: Mus musculus

<400> SEQUENCE: 9
```

-continued

Met Ala Glu Tyr Gly Thr Leu Leu Gln Asp Leu Thr Asn Asn Ile Thr
1               5                   10                  15

Leu Glu Asp Leu Glu Gln Leu Lys Ser Ala Cys Lys Glu Asp Ile Pro
            20                  25                  30

Ser Glu Lys Ser Glu Glu Ile Thr Thr Gly Ser Ala Trp Phe Ser Phe
            35                  40                  45

Leu Glu Ser His Asn Lys Leu Asp Lys Asp Asn Leu Ser Tyr Ile Glu
        50                  55                  60

His Ile Phe
65

<210> SEQ ID NO 10
<211> LENGTH: 67
<212> TYPE: PRT
<213> ORGANISM: Homo sapiens

<400> SEQUENCE: 10

Met Asp Pro Phe Leu Val Leu Leu His Ser Val Ser Ser Ser Leu Ser
1               5                   10                  15

Ser Ser Glu Leu Thr Glu Leu Lys Phe Leu Cys Leu Gly Arg Val Gly
            20                  25                  30

Lys Arg Lys Leu Glu Arg Val Gln Ser Gly Leu Asp Leu Phe Ser Met
            35                  40                  45

Leu Leu Glu Gln Asn Asp Leu Glu Pro Gly His Thr Glu Leu Leu Arg
        50                  55                  60

Glu Leu Leu
65

<210> SEQ ID NO 11
<211> LENGTH: 67
<212> TYPE: PRT
<213> ORGANISM: Mus musculus

<400> SEQUENCE: 11

Met Asp Pro Phe Leu Val Leu Leu His Ser Leu Ser Gly Ser Leu Ser
1               5                   10                  15

Gly Asn Asp Leu Met Glu Leu Lys Phe Leu Cys Arg Glu Arg Val Ser
            20                  25                  30

Lys Arg Lys Leu Glu Arg Val Gln Ser Gly Leu Asp Leu Phe Thr Val
            35                  40                  45

Leu Leu Glu Gln Asn Asp Leu Glu Arg Gly His Thr Gly Leu Leu Arg
        50                  55                  60

Glu Leu Leu
65

<210> SEQ ID NO 12
<211> LENGTH: 66
<212> TYPE: PRT
<213> ORGANISM: Homo sapiens

<400> SEQUENCE: 12

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

```
Gln Glu Lys Arg Met Leu Glu Glu Ser Asn Leu Ser Phe Leu Lys Glu
    50                  55                  60

Leu Leu
65

<210> SEQ ID NO 13
<211> LENGTH: 68
<212> TYPE: PRT
<213> ORGANISM: Homo sapiens

<400> SEQUENCE: 13

Gln Ile Ser Ala Tyr Arg Val Met Leu Tyr Gln Ile Ser Glu Glu Val
1               5                   10                  15

Ser Arg Ser Glu Leu Arg Ser Phe Lys Phe Leu Leu Gln Glu Glu Ile
            20                  25                  30

Ser Lys Cys Lys Leu Asp Asp Asp Met Asn Leu Leu Asp Ile Phe Ile
        35                  40                  45

Glu Met Glu Lys Arg Val Ile Leu Gly Glu Gly Lys Leu Asp Ile Leu
    50                  55                  60

Lys Arg Val Cys
65

<210> SEQ ID NO 14
<211> LENGTH: 15
<212> TYPE: PRT
<213> ORGANISM: Homo sapiens

<400> SEQUENCE: 14

Lys Leu Gln Ala Ala Val Asp Gly Pro Met Asp Lys Lys Glu Glu
1               5                   10                  15

<210> SEQ ID NO 15
<211> LENGTH: 15
<212> TYPE: PRT
<213> ORGANISM: Mus musculus

<400> SEQUENCE: 15

Lys Leu Gln Ala Ser Val Arg Gly Pro Ser Val Lys Lys Glu Glu
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: Synthetic, based on Homo sapiens

<400> SEQUENCE: 16

Glu Gln Lys Leu Ile Ser Glu Glu Asp Leu
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic, based on Orthomyxoviridae
      Influenza A virus

<400> SEQUENCE: 17

Tyr Pro Tyr Asp Val Pro Asp Tyr Ala
1               5
```

```
<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Met Asp Tyr Lys Asp Asp Asp Asp Lys Ala
 1               5                  10

<210> SEQ ID NO 19
<211> LENGTH: 33
<212> TYPE: DNA
<213> ORGANISM: Homo sapiens

<400> SEQUENCE: 19
ctagcgcccg ccgcgcctct gtggaattct gaa                            33

<210> SEQ ID NO 20
<211> LENGTH: 33
<212> TYPE: DNA
<213> ORGANISM: Homo sapiens

<400> SEQUENCE: 20
agctttcaga attccacaga ggcgcggcgg gcg                            33

<210> SEQ ID NO 21
<211> LENGTH: 26
<212> TYPE: DNA
<213> ORGANISM: Homo sapiens

<400> SEQUENCE: 21
tctctagaac aaacagaagt actgga                                    26

<210> SEQ ID NO 22
<211> LENGTH: 24
<212> TYPE: DNA
<213> ORGANISM: Homo sapiens

<400> SEQUENCE: 22
gatctagaca tcttcctgtg ggaa                                      24

<210> SEQ ID NO 23
<211> LENGTH: 26
<212> TYPE: DNA
<213> ORGANISM: Homo sapiens
<220> FEATURE:

<400> SEQUENCE: 23
gcggatccat gagtctgcag tggact                                    26

<210> SEQ ID NO 24
<211> LENGTH: 26
<212> TYPE: DNA
<213> ORGANISM: Homo sapiens

<400> SEQUENCE: 24
gcgaattctt actcttcctt cttgtc                                    26

<210> SEQ ID NO 25
<211> LENGTH: 26
<212> TYPE: DNA
<213> ORGANISM: Homo sapiens
```

-continued

```
<400> SEQUENCE: 25
gcggatccat gagtctgcag tggact                                          26

<210> SEQ ID NO 26
<211> LENGTH: 27
<212> TYPE: DNA
<213> ORGANISM: Homosapiens

<400> SEQUENCE: 26
gcgaattcag tcaacagcag ctccctt                                         27

<210> SEQ ID NO 27
<211> LENGTH: 28
<212> TYPE: DNA
<213> ORGANISM: Homo sapiens

<400> SEQUENCE: 27
gcgcggatcc ctcatttcgc agcaggcc                                        28

<210> SEQ ID NO 28
<211> LENGTH: 27
<212> TYPE: DNA
<213> ORGANISM: Homo sapiens

<400> SEQUENCE: 28
gcgaattcag tcaacagcag ctccctt                                         27

<210> SEQ ID NO 29
<211> LENGTH: 26
<212> TYPE: DNA
<213> ORGANISM: Homo sapiens

<400> SEQUENCE: 29
gcggatccgg aggcaagttg gatgtc                                          26

<210> SEQ ID NO 30
<211> LENGTH: 26
<212> TYPE: DNA
<213> ORGANISM: Homo sapiens

<400> SEQUENCE: 30
gcgaattctt actcttcctt cttgtc                                          26

<210> SEQ ID NO 31
<211> LENGTH: 64
<212> TYPE: PRT
<213> ORGANISM: Homo sapiens

<400> SEQUENCE: 31

Arg Val Ser Leu Phe Arg Asn Leu Leu Tyr Glu Leu Ser Glu Gly Ile
 1               5                  10                  15

Asp Ser Glu Asn Leu Lys Asp Met Ile Phe Leu Leu Lys Asp Ser Leu
            20                  25                  30

Pro Lys Thr Glu Met Thr Ser Leu Ser Phe Leu Ala Phe Leu Glu Lys
        35                  40                  45

Gln Gly Lys Ile Asp Glu Asp Asn Leu Thr Cys Leu Glu Asp Leu Cys
    50                  55                  60

<210> SEQ ID NO 32
<211> LENGTH: 68
<212> TYPE: PRT
<213> ORGANISM: Homo sapiens
```

```
<400> SEQUENCE: 32

Cys Lys Val Ser Phe Arg Glu Lys Leu Leu Ile Ile Asp Ser Asn Leu
  1               5                  10                  15

Gly Val Gln Asp Val Glu Asn Leu Lys Phe Leu Cys Ile Gly Leu Val
             20                  25                  30

Pro Asn Lys Lys Leu Glu Lys Ser Ser Ser Ala Ser Asp Val Phe Glu
         35                  40                  45

His Leu Leu Ala Glu Asp Leu Leu Ser Glu Glu Asp Pro Phe Phe Leu
     50                  55                  60

Ala Glu Leu Leu
 65

<210> SEQ ID NO 33
<211> LENGTH: 245
<212> TYPE: PRT
<213> ORGANISM: Mus musculus

<400> SEQUENCE: 33

Met Ser Leu Gln Trp Thr Thr Val Ala Thr Phe Leu Tyr Ala Glu Val
  1               5                  10                  15

Phe Ala Val Leu Leu Leu Cys Ile Pro Phe Ile Ser Pro Lys Arg Trp
             20                  25                  30

Gln Lys Val Phe Lys Ser Arg Leu Val Glu Leu Val Thr Tyr Gly
         35                  40                  45

Asn Thr Phe Phe Val Val Leu Ile Val Ile Leu Val Leu Leu Val Ile
     50                  55                  60

Asp Ala Val Arg Glu Ile Leu Lys Tyr Asp Asp Val Thr Glu Lys Val
 65                   70                  75                  80

Asn Leu Gln Asn Asn Pro Gly Ala Met Glu His Phe His Met Lys Leu
                 85                  90                  95

Phe Arg Ala Gln Arg Asn Leu Tyr Ile Ala Gly Leu Ser Leu Leu Leu
            100                 105                 110

Ser Phe Leu Leu Arg Arg Leu Val Thr Leu Ile Ser Gln Gln Ala Thr
            115                 120                 125

Leu Leu Ala Ser Asn Glu Ala Phe Lys Lys Gln Ala Glu Ser Ala Ser
        130                 135                 140

Glu Ala Ala Lys Lys Tyr Met Glu Glu Asn Asp Gln Leu Lys Lys Gly
145                 150                 155                 160

Ala Ala Glu Asp Gly Asp Lys Leu Asp Ile Gly Asn Thr Glu Met Lys
                165                 170                 175

Leu Glu Glu Asn Lys Ser Leu Lys Asn Asp Leu Arg Lys Leu Lys Asp
            180                 185                 190

Glu Leu Ala Ser Thr Lys Lys Leu Glu Lys Ala Glu Asn Glu Ala
        195                 200                 205

Leu Ala Met Gln Lys Gln Ser Glu Gly Leu Thr Lys Glu Tyr Asp Arg
    210                 215                 220

Leu Leu Glu Glu His Ala Lys Leu Gln Ala Ser Val Arg Gly Pro Ser
225                 230                 235                 240

Val Lys Lys Glu Glu
                245
```

METHODS AND REAGENTS FOR MODULATING APOPTOSIS

BACKGROUND OF THE INVENTION

This invention relates to apoptosis.

Apoptosis, which is also referred to as programmed cell death, is a form of cell death characterized by membrane blebbing and nuclear DNA fragmentation. Apoptotic cell death is morphologically distinct from necrotic cell death and is important in the normal development and maintenance of multicellular organisms. Dysregulation of apoptosis has been implicated in a number of human diseases. An inappropriate suppression of apoptosis in a cell may lead to the uncontrolled propagation of that cell. Such an event would favor, for example, the development of cancer. In contrast, a failure to control the extent of apoptotic cell death may lead to degeneration of specific tissues and cell-types. For example, an inappropriately high level of apoptosis in leukocytes may result in acquired immunodeficiency. Likewise, certain neurodegenerative disorders may result from an inappropriately high level of apoptosis in neuronal cells and tissues.

Although apoptotic cell death is initially triggered by a specific death signal received, for example, by ligation of the Fas cell surface molecule, execution of the apoptotic pathway occurs only upon the activation of members of the Ced-3/ICE (caspase) family of cysteine proteases. There are at least 10 known members of the caspase family whose activities lead to site-specific cleavage and consequent activation/inactivation of various target molecules. FLICE and related caspases may initiate apoptosis by activating a downstream caspase cascade, including CPP32 (caspase-3).

The decision to engage the apoptotic execution pathway in response to specific death signals depends on the status of various cellular regulators of apoptosis, including p53 and the Bcl-2/Bax set point. The latter set point arises through heterodimerization between the Bcl-2/Bcl-$X_L$ family of suppressors and promoters, respectively, in which the ratio of the heterodimerizing partners determines the outcome—cell death or cell survival—in response to various death signals. Bad, a more distantly related family member, is a direct regulator of the set point, by a mechanism that is governed by phosphorylation. The phosphorylation may, in turn, be affected by Bcl-2-dependent recruitment of Raf-1 kinase.

Although it is now known that Bcl-2/Bcl-$X_L$ controls the apoptotic execution pathway at a point that is either at or upstream of pro-enzyme activation of the caspases, how this is achieved remains to be elucidated. There thus remains a need to identify Bcl-2 binding proteins that are functionally linked to apoptosis. There also remains a need to identify factors that interact with Bcl-2 and modulate the apoptotic signalling pathway. Further, it would be useful to identify factors which enable a signalling of the apoptotic pathway from Bcl-2 and interacting factors to the caspases involved therein.

SUMMARY OF THE INVENTION

We have discovered that p28 Bap31 polypeptides, nucleic acids, and antibodies may be used for the detection and treatment of conditions involving apoptosis and for the identification of therapeutic molecules.

In a first aspect, the invention features a substantially pure p28 Bap31 polypeptide fragment that modulates apoptosis.

In a second aspect, the invention features a substantially purified nucleic acid molecule encoding a substantially pure p28 Bap31 polypeptide fragment that modulates apoptosis.

In various embodiments of the first two aspects of the invention, the fragment includes a domain that is required for an association of p28 Bap31 with pro-FLICE, or a domain that is required for an association of p28 Bap31 with a Bcl-2 protein (e.g., Bcl-2 or Bcl-$X_L$). In other preferred embodiments, the fragment either increases apoptosis or inhibits apoptosis. In yet another embodiment of the first and second aspects of the invention, the fragment is from a mammal (e.g., a human or a mouse).

In an third aspect, the invention features a substantially pure polypeptide that modulates apoptosis, the polypeptide having 50% or greater amino acid sequence identity to the amino acid sequence of SEQ ID NO: 1. In preferred embodiments, the polypeptide has 70% or greater amino acid sequence identity to the amino acid sequence of SEQ ID NO: 1, or has 80% or greater amino acid sequence identity to the amino acid sequence of SEQ ID NO: 1.

In a fourth aspect, the invention features a method for modulating apoptosis in a cell that includes administering to the cell a compound that alters p28 Bap31 biological activity, the compound being administered at a dosage which is sufficient to modulate the p28 Bap31 biological activity. In various preferred embodiments of this aspect of the invention, the p28 Bap31 biological activity may be cleavage of the p28 Bap31 polypeptide to produce a p20 product, formation of a complex of the p28 Bap31 polypeptide with pro-FLICE, formation of a complex of the p28 Bap31 polypeptide with a Bcl-2 protein (e.g., Bcl-2 or Bcl-$X_L$), binding of the p28 Bap31 polypeptide by an antibody that specifically binds to p28 Bap31, or expression of the p28 Bap31 polypeptide in the cell. In various other embodiments, the cell is from a mammal (e.g., a human or a rodent).

In another embodiment of the fourth aspect of the invention, the modulating is inhibiting. In another embodiment, where the modulating is inhibiting, the cell is in a mammal with a degenerative disease (e.g., a neurodegenerative disease, cirrhosis of the liver, a myelodysplastic syndrome, an ischemic injury, an infection with HIV, or a bone degenerative disease). In yet an other embodiment, where the modulating is inhibiting, the compound may be a p28 Bap31 antisense nucleic acid molecule, an antibody that specifically binds to p28 Bap31 (e.g., a p28 Bap31 neutralizing antibody), a p20 antisense nucleic acid molecule, an antibody that specifically binds to p20 (e.g., a p20 neutralizing antibody), a p20-inhibiting amount of a Bcl-2 protein, or a p20-inhibiting amount of a nucleic acid molecule encoding a Bcl-2 polypeptide, where the nucleic acid molecules are positioned for expression in said cell.

In another embodiment of the fourth aspect of the invention, the modulating is increasing. In another embodiment, where the modulating is increasing, the cell is in a mammal with a neoplasia. In another embodiment, where the modulating is increasing, the compound may be a p28 Bap31 polypeptide, a p20 product that is a cleavage product of p28 Bap31, or a nucleic acid molecule encoding a p28 Bap31 polypeptide, where the nucleic acid molecule is positioned for expression in the cell.

In a fifth aspect, the invention features a method for detecting a compound that modulates apoptosis that includes the steps of: (a) providing a cell having: (i) a reporter gene operably linked to a DNA-binding-protein recognition site; (ii) a first fusion gene capable of expressing a first fusion protein, the first fusion protein including a polypeptide fragment of p28 Bap31 covalently bonded to a binding moiety, the binding moiety capable of specifically binding to the DNA-binding-protein recognition site; and (iii) a second fusion gene capable of expressing a second fusion protein, the second fusion protein including a polypeptide fragment of a second protein covalently bonded to a gene activating moiety; (b) exposing the cell to the compound; and (c) measuring reporter gene expression in the cell, a change in the reporter gene expression identifying a compound that modulates apoptosis. In one embodiment of this aspect, the cell is a yeast cell.

In a sixth aspect, the invention features a method for detecting a compound that modulates apoptosis that includes the steps of: (a) providing a cell having: (i) a reporter gene operably linked to a DNA-binding-protein recognition site; (ii) a first fusion gene capable of expressing a first fusion protein, the first fusion protein including a polypeptide fragment of a second protein covalently bonded to a binding moiety, the binding moiety capable of specifically binding to the DNA-binding-protein recognition site; and (iii) a second fusion gene capable of expressing a second fusion protein, the second fusion protein including a polypeptide fragment of p28 Bap31 covalently bonded to a gene activating moiety; (b) exposing the cell to the compound; and (c) measuring reporter gene expression in the cell, a change in the reporter gene expression identifying a compound that modulates apoptosis. In one embodiment of this aspect, the cell is a yeast cell.

In a seventh aspect, the invention features a method for identifying a compound that modulates apoptosis that includes the steps of: (a) providing a first polypeptide including a region of p28 Bap31, the region of p28 Bap31 including a first domain that interacts with a second protein; (b) allowing an interaction of the first polypeptide with a second polypeptide that includes a region of the second protein, the region of the second protein including a second domain that interacts with the p28 Bap31; (c) contacting the interaction of the first polypeptide and the second polypeptide with a candidate compound; and (d) measuring the interaction of the first polypeptide and the second polypeptide, a change in the interaction of the first polypeptide and the second polypeptide in the presence of the candidate compound relative to an interaction of the first polypeptide and the second polypeptide not contacted with the candidate compound identifying the presence of a compound that modulates apoptosis.

In various embodiments of the fifth, sixth, and seventh aspects of the invention, the second protein is a Bcl-2 protein (e.g., Bcl-2 or Bcl-$X_L$).

In an eighth aspect, the invention features a method for identifying a compound that modulates apoptosis that includes: (a) providing a cell expressing p28 Bap31 polypeptide; and (b) contacting the cell with a candidate compound and monitoring the level of p28 Bap31 biological activity, a change in the level of p28 Bap31 biological activity in response to the candidate compound relative to a level of p28 Bap31 biological activity in a cell not contacted with the candidate compound identifying a compound that modulates apoptosis.

In various preferred embodiments of the eighth aspect of the invention, the p28 biological activity may be cleavage of the p28 Bap31 polypeptide to produce a p20 product, formation of a complex of the p28 Bap31 polypeptide with pro-FLICE, formation of a complex of the p28 Bap31 polypeptide with a Bcl-2 protein (e.g., Bcl-2 or Bcl-$X_L$), binding of the p28 Bap31 polypeptide by an antibody that specifically binds to p28 Bap31, or expression of the p28 Bap31 polypeptide in the cell. In various other embodiments, the cell is from a mammal (e.g., a human or a rodent).

In another embodiment of the fifth, sixth, seventh, and eighth aspects of the invention, where the change is a decrease, the compound is useful for inhibiting apoptosis. In another embodiment, where the change is a decrease, the compound may be used to treat an animal with a degenerative disease (e.g., a neurodegenerative disease, cirrhosis of the liver, a myelodysplastic syndrome, an ischemic injury, an infection with HIV, or a bone degenerative disease). In yet another embodiment, where the change is an increase, the compound is useful for increasing apoptosis. In yet another embodiment, where the change is an increase, the compound may be used to treat an animal with neoplasia (e.g., a cancer, a hyperplastic disorder, or a benign tumor).

In a ninth aspect, the invention features a method for diagnosing a mammal for the presence of a disease involving altered apoptosis or an increased likelihood of developing the disease, where the method includes measuring the level of p28 Bap31 biological activity in a sample from the mammal, a change in the level of p28 Bap31 biological activity in the sample relative to a level of p28 Bap31 biological activity in a sample from an unaffected mammal being an indication that the mammal has the disease or increased likelihood of developing the disease.

In various preferred embodiments of the ninth aspect of the invention, the p28 biological activity may be cleavage of the p28 Bap31 polypeptide to produce a p20 product, formation of a complex of the p28 Bap31 polypeptide with pro-FLICE, formation of a complex of the p28 Bap31 polypeptide with a Bcl-2 protein (e.g., Bcl-2 or Bcl-$X_L$), binding of the p28 Bap31 polypeptide by an antibody that specifically binds to p28 Bap31, or expression of the p28 Bap31 polypeptide in the cell. In another embodiment, the mammal is a human or a rodent.

In another embodiment of the ninth aspect of the invention, where the change is a reduction indicates that the mammal has the disease or increased likelihood of developing the disease, wherein the disease is caused by decreased apoptosis. In another embodiment, where the change is a reduction, the disease may be neoplasia (e.g., a cancer, a hyperplastic disorder, or a benign tumor).

In yet another embodiment of the ninth aspect of the invention, where the change is an increase indicates that the mammal has the disease or increased likelihood of developing the disease, wherein the disease is caused by increased apoptosis. In another embodiment, where the change is an increase, the disease may be a degenerative disease (e.g., a neurodegenerative disease, cirrhosis of the liver, a myelodysplastic syndrome, an ischemic injury, an infection with HIV, or a bone degenerative disease).

In a tenth aspect, the invention features a method for identifying a nucleic acid molecule encoding a p28 Bap31 polypeptide that includes: (a) providing a cell; (b) introducing by transformation into the cell a candidate nucleic acid molecule, the nucleic acid molecule being positioned for expression in the cell; and (c) determining whether the transformed cell exhibits an increased level of apoptosis relative to a cell not transformed with the candidate nucleic acid molecule, wherein the increased level of apoptosis in the transformed cell identifies a nucleic acid molecule encoding a p28 Bap31 polypeptide.

In an eleventh aspect, the invention features a method for identifying a nucleic acid molecule encoding a p28 Bap31 polypeptide that includes: (a) providing a cell; (b) introducing by transformation into the cell a candidate nucleic acid molecule, the nucleic acid molecule being positioned for expression in the cell; and (c) determining whether the transformed cell exhibits an increased level of p28 Bap31 biological activity relative to a cell not transformed with the candidate nucleic acid molecule, wherein the increased level of p28 Bap31 biological activity in the transformed cell identifies a nucleic acid molecule encoding a p28 Bap31 polypeptide.

In a twelfth aspect, the invention features a method for identifying a nucleic acid molecule encoding a protease that cleaves p28 Bap31 into p20 that includes: (a) providing a cell expressing a p28 Bap31 polypeptide; (b) introducing by transformation into the cell a candidate nucleic acid molecule, the nucleic acid molecule being positioned for expression in the cell; and (c) determining whether the transformed cell exhibits an increased level of p20 expression relative to a cell not transformed with the candidate nucleic acid molecule, wherein the increased level of p20 expression in the transformed cell identifies a nucleic acid molecule encoding a protease that cleaves p28 Bap31 into p20.

In a thirteenth aspect, the invention features a method for identifying a nucleic acid molecule encoding a protease that cleaves p28 Bap31 into p20 that includes: (a) providing a cell expressing a p28 Bap31 polypeptide; (b) introducing by transformation into the cell a candidate nucleic acid molecule, the nucleic acid molecule being positioned for expression in the cell; and (c) determining whether the transformed cell exhibits an increased level of apoptosis relative to a cell not transformed with the candidate nucleic acid molecule, wherein the increased level of apoptosis in the transformed cell identifies a nucleic acid molecule encoding a protease that cleaves p28 Bap31 into p20.

In a preferred embodiment of the tenth, eleventh, twelfth, and thirteenth aspects of the invention, the cell is from a mammal (e.g., a human or a rodent).

In a fourteenth aspect, the invention features a kit for diagnosing a mammal for the presence of a disease involving altered apoptosis or an increased likelihood of developing the disease, where the kit includes a substantially pure antibody that specifically binds a p28 Bap31 polypeptide, where the antibody modulates apoptosis. In one embodiment of this aspect of the invention, the kit further includes a means for detecting the binding of the antibody to the p28 Bap31 polypeptide.

In a fifteenth aspect, the invention features a substantially pure antibody that specifically binds to the p28 Bap31 polypeptide, where the antibody modulates apoptosis. In preferred embodiments, the antibody is a polyclonal antibody, a monoclonal antibody, or a neutralizing antibody.

In a sixteenth aspect, the invention features a transgenic cell (e.g., an embryonal cell) that has a knockout mutation of an endogenous p28 Bap31 gene. In one embodiment, the mutation includes an insertion of exogenous DNA.

In a seventeenth aspect, the invention features a transgenic animal generated from a transgenic cell (e.g., an embryonal cell) that has a knockout mutation of an endogenous p28 Bap31 gene, where the endogenous p28 Bap31 gene is not expressed in the transgenic animal. In one embodiment of this aspect, the germ-line cells and somatic cells of the transgenic animal do not express the endogenous p28 Bap31 gene. In another embodiment, the transgenic animal includes germ-line cells and somatic cells expressing a nucleic acid molecule encoding a truncated or a mutated p28 Bap31 polypeptide.

In an eighteenth aspect, the invention features a vector including a knockout mutation in a DNA sequence encoding a p28 Bap31 gene, where the gene includes: (a) a first region corresponding to a 5' sequence of the p28 Bap31 gene, wherein the initiator methionine codon of the p28 Bap31 gene is absent from the sequence; (b) a second region including DNA including a drug-resistance cassette, the DNA capable of conferring resistance to the drug in a cell when the DNA is present in the cell; and (c) a third region corresponding to a 3' sequence of the p28 Bap31 gene.

In a nineteenth aspect, the invention features a vector including a knockout mutation in a DNA sequence encoding a p28 Bap31 gene, where the gene includes: (a) a first region corresponding to a 5' sequence of the p28 Bap31 gene, wherein the initiator methionine codon of the p28 Bap31 gene is absent from the sequence; (b) a second region including DNA including a drug-resistance cassette, the DNA capable of conferring resistance to the drug in a cell when the DNA is present in the cell; and (c) a third region corresponding to a 3' sequence of the p28 Bap31 gene.

In a twentieth aspect, the invention features a method of producing a transgenic mammal lacking expression of an endogenous p28 Bap31 polypeptide that includes: (a) introducing by homologous recombination a nucleic acid molecule encoding a knockout mutation of a p28 Bap31 gene into a locus occupied by an endogenous p28 Bap31 gene, the locus present in the genome of an embryonal cell of the mammal; and (b) growing the embryonal cell to produce the transgenic mammal.

In a twenty-first aspect, the invention features a therapeutic composition that includes, as an active ingredient, a p20 cleavage product of p28 Bap31, the active ingredient being formulated in a physiologically acceptable carrier, where the composition modulates apoptosis.

In a twenty-second aspect, the invention features a therapeutic composition that includes, as an active ingredient, a p28 Bap31 polypeptide, the active ingredient being formulated in a physiologically acceptable carrier, where the composition modulates apoptosis.

In a twenty-third aspect, the invention features a therapeutic composition that includes, as an active ingredient, an antibody that specifically binds p28 Bap31, the active ingredient being formulated in a physiologically acceptable carrier, where the composition modulates apoptosis.

In a twenty-fourth aspect, the invention features a therapeutic composition that includes, as an active ingredient, an antisense nucleic acid molecule that corresponds to p28 Bap31, the active ingredient being formulated in a physiologically acceptable carrier, where the composition modulates apoptosis.

In a twenty-fifth aspect, the invention features the use of a p28 Bap31 polypeptide for the manufacture of a medicament for the modulation of apoptosis.

In a twenty-sixth aspect, the invention features the use of an antibody that specifically binds to p28 Bap31 for the manufacture of a medicament for the modulation of apoptosis.

In a twenty-seventh aspect, the invention features the use of an antisense nucleic acid molecule corresponding to p28 Bap31 for the manufacture of a medicament for the modulation of apoptosis.

In a twenty-eighth aspect, the invention features the use of a p20 cleavage product of p28 Bap31 for the manufacture of a medicament for the modulation of apoptosis.

In a twenty-ninth aspect, the invention features the use of an antibody that specifically binds to a p20 cleavage product of p28 Bap31 for the manufacture of a medicament for the modulation of apoptosis.

In a thirtieth aspect, the invention features the use of an antisense nucleic acid molecule corresponding to a p20 cleavage product of p28 Bap31 for the manufacture of a medicament for the modulation of apoptosis.

As summarized above, a p28 Bap31 nucleic acid molecule, polypeptide, or antibody may be used to modulate apoptosis. Furthermore, a p28 Bap31 nucleic acid molecule, polypeptide, or antibody may be used in the discovery and/or manufacture of a medicament for the modulation of apoptosis.

By "p28 Bap31," "p28 Bap31 protein," or "p28 Bap31 polypeptide" is meant a protein, or a polypeptide fragment thereof, that can interact with a Bcl-2 protein (including, without limitation, Bcl-2 and Bcl-$X_L$) or a pro-FLICE protein, that can participate in apoptosis, or that can be cleaved to produce a p20 product (i.e., an approximately 20 kDa product), that can induce apoptosis when expressed in a cell. Preferably, a p28 Bap31 protein has an amino acid sequence that is at least 50% identical to the amino acid sequence of human Bap31 (GenBank accession number X81817) or to the amino acid sequence of human CDM (GenBank accession number Z31696), more preferably at least 60% identical, more preferably at least 70% identical, still more preferably at least 80% identical, and most preferably at least 90% identical to at least one of these sequences. It will be understood that a fragment thereof has a p28 Bap31 biological activity that is observed with full length p28 Bap31 protein; preferably, the p28 Bap31 biological activity is at least 50% as observed with full length p28 Bap31.

Polypeptide fragments of p28 Bap31 that are a part of the invention include those fragments that bind Bcl-2 polypeptides, those fragments that are capable of selecting an antibody which specifically binds p28 Bap31, and those fragments that can modulate apoptosis in a cell.

By "p28 Bap31 gene" is meant a gene encoding p28 Bap31. Preferably, sequences include sequences which encode polypeptide fragments of the p28 Bap31, as defined above. In preferred embodiments, included as a part of the gene are the nucleic acid sequences flanking the 5' and 3' regions of the coding region of the p28 Bap31 gene sequence. Mammalian p28 Bap31 genes include nucleotide sequences isolated from any mammalian source. Preferably, the mammal is a human.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., a p28 Bap31 specific antibody. A purified antibody may be obtained, for example, by affinity chromatography using recombinantly-produced polypeptide or conserved motif peptides and standard techniques.

By "specifically binds" is meant an antibody that recognizes and binds a polypeptide but that does not substantially recognize and bind other molecules in a sample, e.g., a biological sample, that naturally includes protein. One preferred antibody specifically binds to the p28 Bap31 polypeptide.

By "p28 Bap31 biological activity," as used herein in reference to p28 Bap31, is meant any one of the biological activities of a p28 Bap31 protein (or a polypeptide fragment thereof). P28 Bap31 biological activities include, without limitation, an ability of p28 Bap31 to be cleaved to produce a p20 product, an ability to form a complex with a Bcl-2 protein (e.g., Bcl-2 or Bcl-$X_L$), an ability to form a complex with pro-FLICE, an ability to be bound by an antibody that specifically binds p28 Bap31, an ability to be expressed, and an ability to participate in apoptosis.

By a "compound that alters p28 Bap31 biological activity," is meant a compound that increases or reduces any biological activity of p28 Bap31 (or a fragment thereof), as defined above. Such a compound may be, without limitation, a compound that increases the transcription of p28 Bap31, a compound that increases p28 Bap31 protein expression levels, a p28 Bap31 antisense nucleic acid molecule, an antibody that specifically binds to p28 Bap31, a p20 antisense nucleic acid molecule, an antibody that specifically binds to p20, a p20-inhibiting amount of a Bcl-2 protein, a p20-inhibiting amount of a Bcl-2-expressing nucleic acid molecule, a p28 Bap31 protein (or fragment thereof), a p20 product (or fragment thereof), and a nucleic acid molecule encoding a p28 Bap31 polypeptide (or fragment thereof).

By a "neutralizing antibody," as used herein in reference to an antibody that specifically binds p28 Bap31, is meant an antibody that interferes with any of the biological activities of the p28 Bap31 protein. For example, a p28 Bap31 neutralizing antibody may interfere with the ability of p28 Bap31 to participate in apoptosis, for example, by inhibiting cleavage of p28 Bap31 to produce the p20 product. A p28 Bap31 neutralizing antibody may also interfered with the ability of p28 Bap31 to form a complex with a Bcl-2 protein (e.g., Bcl-2 or Bcl-$X_L$) or to form a complex with pro-FLICE. Such p28 Bap31 neutralizing antibodies may reduce the ability of p28 Bap31 and polypeptide fragments thereof to participate in apoptosis and to associate with pro-FLICE and/or a Bcl-2 protein by, preferably 50%, more preferably by 70%, and most preferably by 90% or more. Standard assays of apoptosis and protein:protein interactions, including those described herein, may be used to assess potentially neutralizing p28 Bap31 antibodies.

By "modulating apoptosis" or "altering apoptosis" is meant increasing or decreasing the number of cells that would otherwise undergo apoptosis in a given cell population. Preferably, the cell population is selected from a group including T cells, neuronal cells, fibroblasts, myocardial cells, or any other cell line known to undergo apoptosis in a laboratory setting, for example, human epithelial KB cells infected with adenovirus type 5 lacking expression of E1B 19K (pm1716/2072). It will be appreciated that the degree of modulation provided by p28 Bap31 or p28 Bap31 modulating compounds in a given assay will vary, but that one skilled in the art can determine the statistically significant change in the level of apoptosis which identifies a p28 Bap31 or a compound which modulates this proteins.

By "increasing apoptosis" is meant any increase in the number of cells that undergo apoptosis relative to an untreated control. Preferably, the increase is at least 25%, more preferably the increase is at least 50%, and most preferably the increase is at least one-fold.

By "inhibiting apoptosis" is meant any decrease in the number of cells that undergo apoptosis relative to an untreated control. Preferably, the decrease is at least 25%, more preferably the decrease is at least 50%, and most preferably the decrease is at least one-fold.

By "protein" or "polypeptide" is meant any chain of more than two amino acids, regardless of post-translational modification such as glycosylation or phosphorylation.

By "substantially identical" is meant a polypeptide or nucleic acid exhibiting at least 50%, preferably at least 85%, more preferably at least 90%, and most preferably at least 95% identity to a reference amino acid or nucleic acid sequence. For polypeptides, the length of comparison sequences will generally be at least 16 amino acids, preferably at least 20 amino acids, more preferably at least 25 amino acids, and most preferably at least 35 amino acids. For nucleic acids, the length of comparison sequences will generally be at least 50 nucleotides, preferably at least 60 nucleotides, more preferably at least 75 nucleotides, and most preferably at least 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is a p28 Bap31 polypeptide that is at least 75%, more preferably at least 90%, and most preferably at least 99%, by weight, pure. A substantially pure p28 Bap31 polypeptide may be obtained, for example, by extraction from a natural source (e.g., a fibroblast, neuronal cell, or lymphocyte) by expression of a recombinant nucleic acid encoding a p28 Bap31 polypeptide, or by chemically synthesizing the protein. Purity can be measured by any appropriate method, e.g., by column chromatography, polyacrylamide gel electrophoresis, or HPLC analysis.

A polypeptide is substantially free of naturally associated components when it is separated from those contaminants which accompany it in its natural state. Thus, a polypeptide which is chemically synthesized or produced in a cellular system different from the cell from which it naturally originates will be substantially free from its naturally associated components. Accordingly, substantially pure polypeptides include those which naturally occur in eukaryotic organisms but are synthesized in E. coli or other prokaryotes, or are synthesized in viruses.

By "substantially pure nucleic acid" is meant nucleic acid that is free of the genes which, in the naturally-occurring genome of the organism from which the nucleic acid of the invention is derived, flank the nucleic acid. The term therefore includes, for example, a recombinant nucleic acid which is incorporated into a vector; into an autonomously replicating plasmid or virus; or into the genomic nucleic acid of a prokaryote or a eukaryote cell; or which exists as a separate molecule (e.g., a cDNA or a genomic or cDNA fragment produced by PCR or restriction endonuclease digestion) independent of other sequences. It also includes a recombinant nucleic acid which is part of a hybrid gene encoding additional polypeptide sequence.

By "embryonal cell" is meant a cell that is capable of being a progenitor to all the somatic and germ-line cells of an organism. Embryonal cells are also referred to as embryonic stem cells, or ES cells. Preferably, the embryonal cells of the invention are mammalian embryonal cells.

By "endogenous," as used herein in reference to a gene or a polypeptide, is meant a gene or polypeptide that is normally present in an organism.

By "germ-line cell" is meant a cell, progenitor, or progeny thereof, which is a product of a meiotic cell division.

By "transformed cell" is meant a cell into which (or into an ancestor of which) has been introduced, by means of recombinant nucleic acid techniques, a nucleic acid molecule encoding (as used herein) a p28 Bap31 polypeptide.

By "transformation" is meant any method for introducing foreign molecules into a cell. Lipofection, calcium phosphate precipitation, retroviral delivery, electroporation, and biolistic transformation are just a few of the teachings which may be used. For example, biolistic transformation is a method for introducing foreign molecules into a cell using velocity driven micro projectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., mitochondria), bacteria, yeast, animal tissue, and cultured cells.

By "transgene" is meant any piece of nucleic acid which is inserted by artifice into a cell, and becomes part of the genome of the organism that develops from that cell. Such a transgene may include a gene which is partly or entirely heterologous (i.e., foreign) to the transgenic organism, or may represent a gene homologous to an endogenous gene of the organism.

By "transgenic" is meant any cell which includes a nucleic acid sequence which is inserted by artifice into a cell and becomes part of the genome of the transgenic organism which develops from that cell. Such a transgene may be partly or entirely heterologous to the transgenic animal. Although transgenic mice represent a preferred embodiment of the invention, other transgenic mammals including, without limitation, transgenic rodents (for example, hamsters, guinea pigs, rabbits, and rats), and transgenic pigs, cattle, sheep, and goats may be constructed by standard techniques and are included in the invention. Preferably, the transgene is inserted by artifice into the nuclear genome.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift mutation, or a mis-sense mutation. Preferably, the mutation is an insertion or deletion (e.g., the p28 Bap31-NEO knockout gene described herein), or is a frameshift mutation that creates a stop codon.

By "positioned for expression" is meant that the nucleic acid molecule is operably linked to a nucleic acid sequence which directs transcription and translation of the sequence (i.e., facilitates the production of, e.g., a p28 Bap31 polypeptide, recombinant polypeptide, or an RNA molecule), such that the nucleic acid molecule that is positioned for expression in a cell is expressed in the cell.

By "promoter" is meant a minimal sequence sufficient to direct transcription of a desired nucleic acid molecule. Also included in the invention are those promoter elements which are sufficient to render promoter-dependent nucleic acid molecule expression controllable for cell type-specific, tissue-specific or inducible by external signals or agents; such elements may be located in the 5' or 3' regions of the native gene, and may be placed, by standard recombinant DNA manipulations, adjacent to or within the desired nucleic acid molecule.

By "operably linked" is meant that a nucleic acid molecule and one or more regulatory sequences are connected in such a way as to permit expression of the nucleic acid molecule when the appropriate molecules (e.g., transcriptional activator proteins) are bound to the regulatory sequences.

By "reporter gene" is meant any gene that encodes a product whose expression is detectable. A reporter gene product may have one of the following attributes, without restriction: fluorescence (e.g., green fluorescent protein), enzymatic activity (e.g., luciferase or chloramphenicol acetyl transferase), toxicity (e.g., ricin), or an ability to be specifically bound by a second molecule (e.g., biotin or a detectably labelled antibody).

By "conserved region" is meant any stretch of six or more contiguous amino acids exhibiting at least 30%, preferably 50%, and most preferably 70% amino acid sequence identity between two or more of the p28 Bap31 family members, (e.g., between human p28 Bap31 and murine p28 Bap31).

By "detectably-labelled" is meant any means for marking and identifying the presence of a molecule, e.g., an oligonucleotide probe or primer, a gene or fragment thereof, or a cDNA or RNA molecule. Methods for detectably-labeling a molecule are well known in the art and include, without limitation, radioactive labeling (e.g., with an isotope such as $^{32}P$ or $^{35}S$) and nonradioactive labeling (e.g., chemiluminescent labeling, e.g., fluorescein labeling).

By "antisense," as used herein in reference to nucleic acids, is meant a nucleic acid sequence that is complementary to the coding strand of a gene, preferably, a p28 Bap31 gene. Preferably the antisense nucleic acid molecule decreases the amount of transcription from the gene; more preferably, the decrease is at least 10%, and most preferably, the decrease is at least 50% when administered at the maximally effective dose.

By "pharmaceutically acceptable carrier" is meant a carrier that is physiologically acceptable to the treated mammal while retaining the therapeutic properties of the compound with which it is administered. One exemplary pharmaceutically acceptable carrier is physiological saline solution. Other physiologically acceptable carriers and their formulations are known to one skilled in the art and described, for example, in *Remington's Pharmaceutical Sciences*, (18$^{th}$ edition), ed. A. Gennaro, 1990, Mack Publishing Company, Easton, Pa.

Other features and advantages of the invention will be apparent from the following description of the preferred embodiments.

BRIEF DESCRIPTION OF THE DRAWINGS

FIG. 2C shows the polypeptide sequence of p28 Bap31/CDM (SEQ ID NO: 1). Peptide sequencing of p20 revealed a perfect match with amino acids 2–10 of human Bap31 (underlined) (GenBank accession number X81817). This was the only detectable sequence in fraction 54, and was detectable together with other sequences in fraction 53, but was not detected in fractions 52 and 55. Predicted transmembrane (TM) segments are boxed and contain charged amino acids in TM1 and TM3 (asterisks). The predicted caspase recognition sites, AAVDG (SEQ ID NO: 2), are highlighted and cleavage denoted by arrows following asp at positions 164 and 238. A potential leucine zipper located between the caspase recognition sites is denoted by bold letters, as is the KKXX (SEQ ID NO: 3) ER retention signal at the COOH-terminus.

FIG. 2D shows an amino acid alignment of the region between the two AAVDG sites in of p28 Bap31 with the death effector domains in indicated proteins. The sequences, given in the single letter amino acid code, were obtained from GenBank, and their relative positions in the molecule shown in parenthesis. Sequences were aligned using the PILEUP program of the GCG software package, and optimized by spacing (shown as dashes).

FIG. 2E shows the amino acid sequence of mouse p28 Bap31 (SEQ ID NO: 33)(GenBank accession number X81816).

Bap31 in the ER membrane. The orientation of the three transmembrane segments of Bap31 predicts a N(lumen)-C (cytosol) topology in the ER membrane. The region of the 13 kDa cytosolic domain containing putative death effector homology (D) and leucine zipper (L) domains, flanked on either side by caspase-8 recognition sites (asterisks), is boxed. Amino acid positions used for generating deletion mutants are indicated. The Flag epitope was inserted immediately upstream of the C-terminal KKEE ER retrieval signal.

Figure 4A:
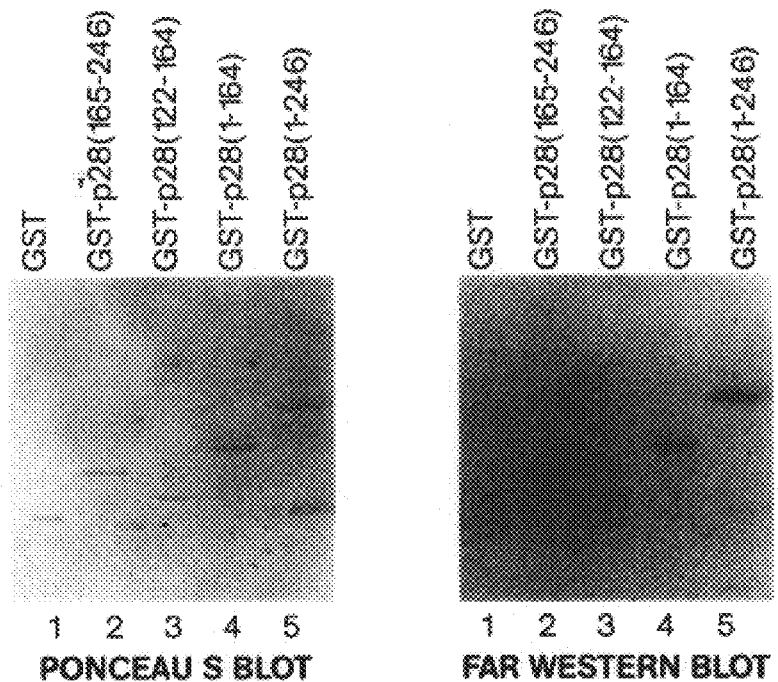
Figure 4A:
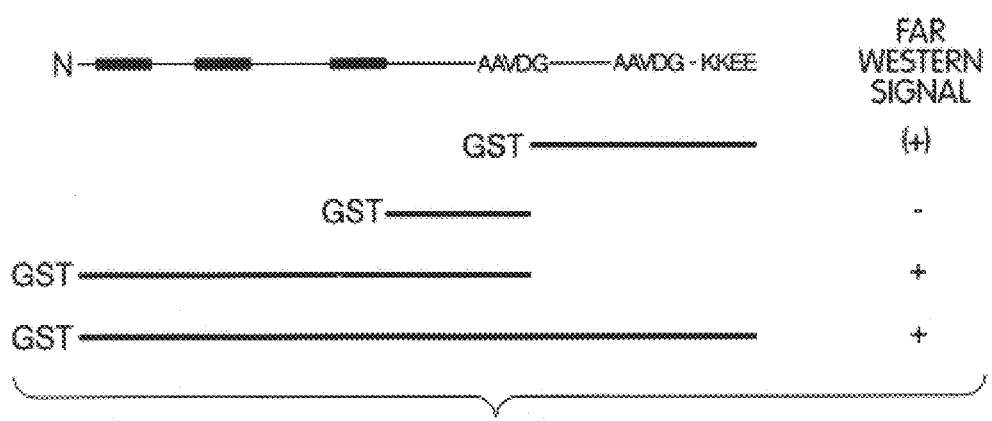

FIG. 4A shows duplicate SDS-PAGE blots (upper panel) of resolved p28 Bap31-GST fusion proteins, one stained with Ponceau S (left blot), and the other subjected to Far Western blotting analysis using $^{32}$P-Bcl-2$\Delta$c22/his6/HMK as a probe. Lanes are: GST (lane 1); GST fused to p28 Bap31 amino acids 165–246 (lane 2); GST fused to p28 Bap31 amino acids 122–164 (lane 3); GST fused to p28 Bap31 amino acids 1–164 (lane 4); and GST fused to p28 Bap31 amino acids 1–246 (lane 5) expressed in bacteria, purified, and transferred to nitrocellulose in duplicate following SDS PAGE. Constructs and results are summarized in the lower panel of the figure as, from top to bottom: GST-p28 (165–246); GST-p28 (122–164); GST-p28 (1–164); and GST-p28 (1–246).

Figure 4B:
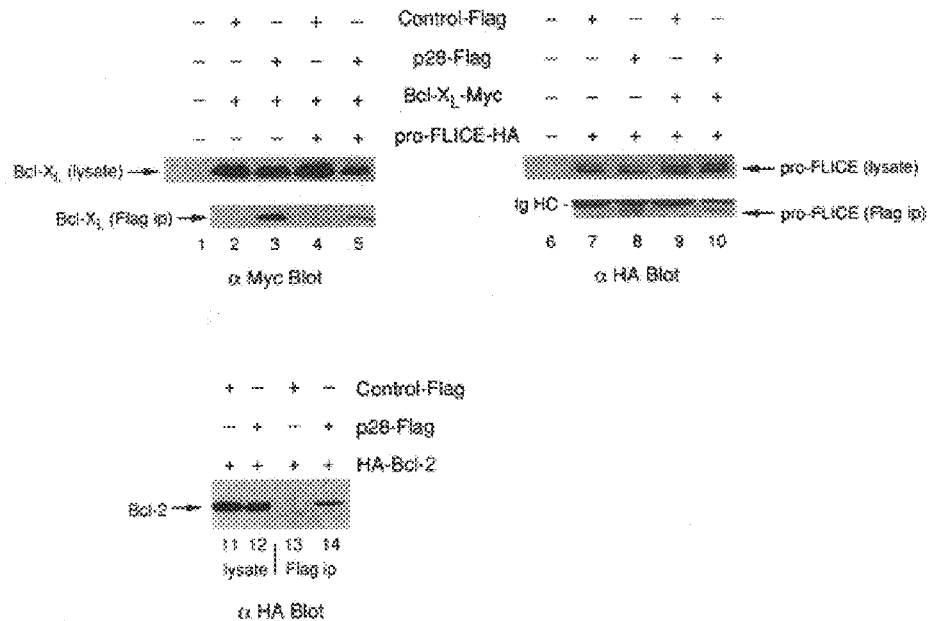

FIG. 4B shows a series of Western blotting analyses from cell lysates and Flag-immunoprecipitates from 293T cells transfected with Myc-tagged Bcl-$X_L$, HA-tagged pro-FLICE, HA-tagged Bcl-2, and/or Flag-tagged p28 Bap31, as indicated (pluses and minuses) probed with anti-Myc or anti-HA antibodies. Immunoreactive bands are visualized by electro-chemiluminescence. "Ig HC" indicates immunoglobulin heavy chain.

Figure 4C:
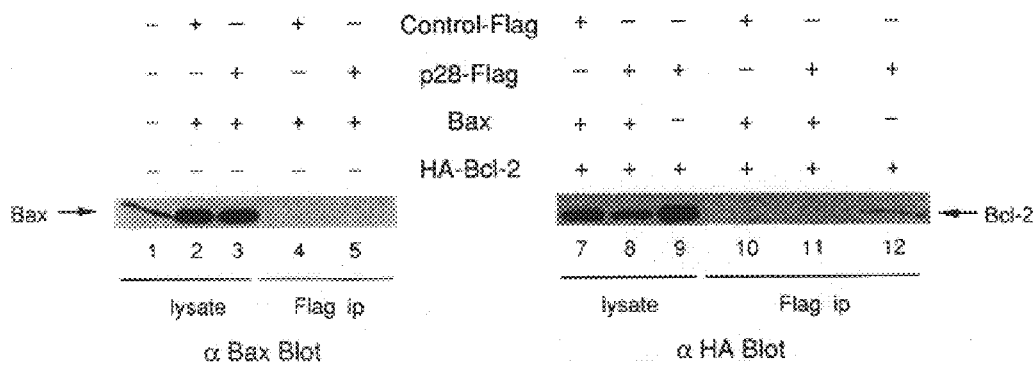

FIG. 4C shows a series of Western blotting analyses from cell lysates and Flag-immunoprecipitates from transfected 293T cells. The analyses were similar to those described in the above brief description of FIG. 4B, except that Bax was included in the 293T cell co-transfections, as indicated.

Figure 5A:
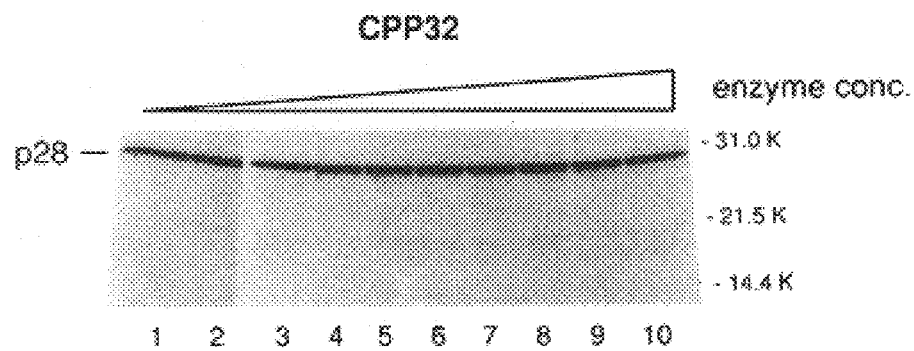
Figure 5A:
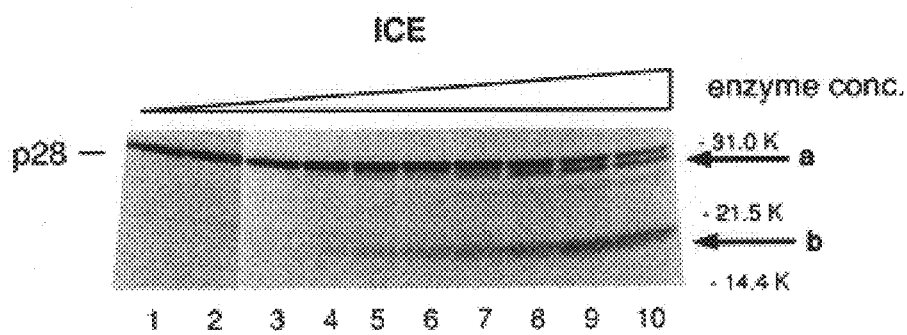
Figure 5A:
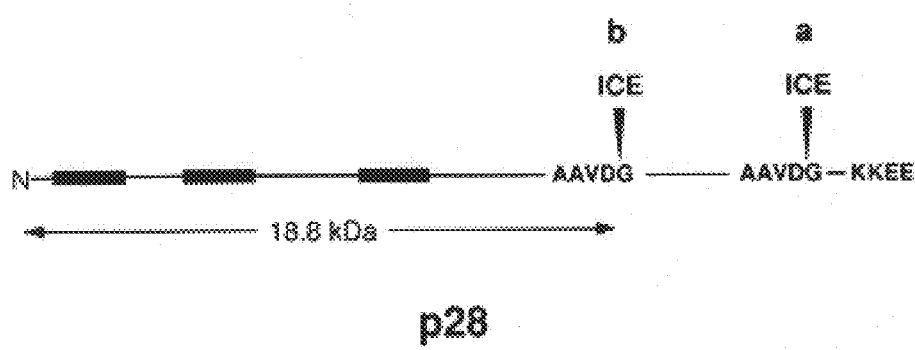

FIG. 5A are SDS-PAGE blots showing resolved products produced by incubating the $^{35}$S-labelled transcription-translation product of p28 Bap31 cDNA with increasing concentrations of CPP32 or ICE. Units of enzyme added per 25 μl reaction mixture were: none (lane 1), 0.0056 (lane 2), 0.98 (lane 3), 1.95 (lane 4), 3.9 (lane 5), 7.8 (lane 6), 15.6 (lane 7), 31.2 (lane 8), 62.5 (lane 9), and 125 (lane 10). The positions of polypeptide molecular mass markers are shown. Arrows designated "a" and "b" denote cleavage products whose sizes are consistent with cleavage of p28 Bap31 at the sites indicated by "a" and "b" in the schematic at the bottom of the figure.

Figure 5B:
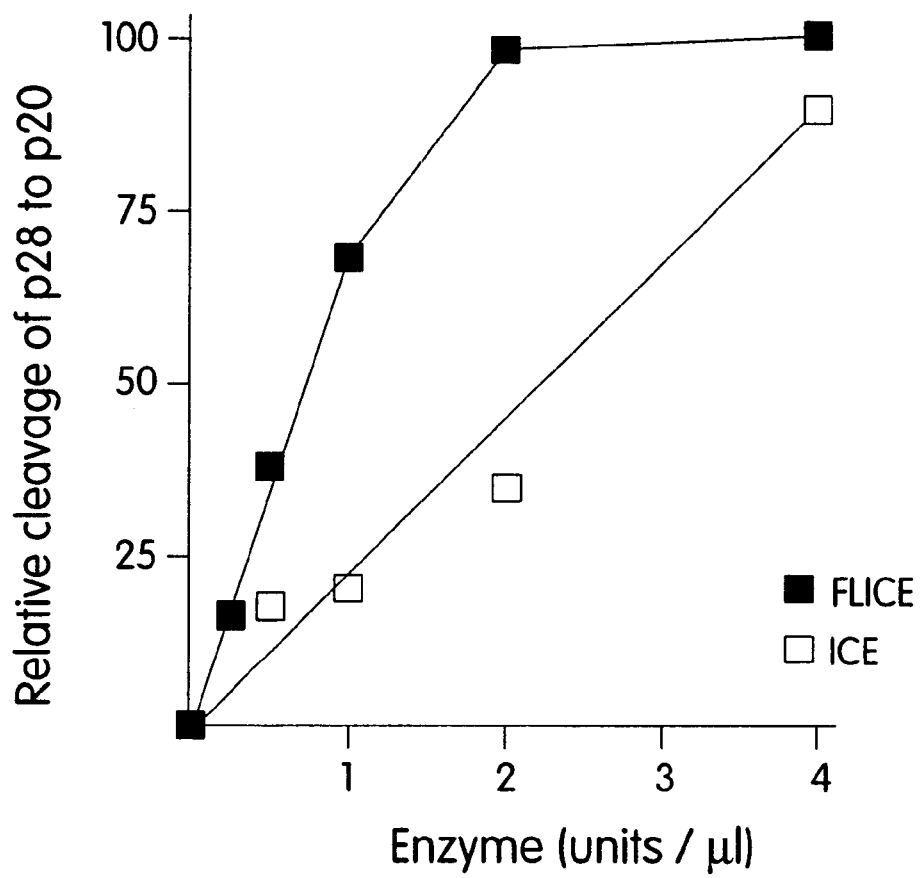

FIG. 5B is a graph showing the analysis as described in the brief description of FIG. 5A, where p28 Bap31 was incubated with purified ICE (caspase-1) or FLICE (caspase-8), and the resulting p20 cleavage product was quantitated using a Phosphorimager. One unit of caspase enzyme activity is equivalent to 1 pmol AMC liberated from fluorogenic tetrapeptide-AMC per min at 25° C. at saturating substrate concentrations (according to the methods described in Nicholson et al., Nature 376: 37–43, 1995).

Figure 6A:
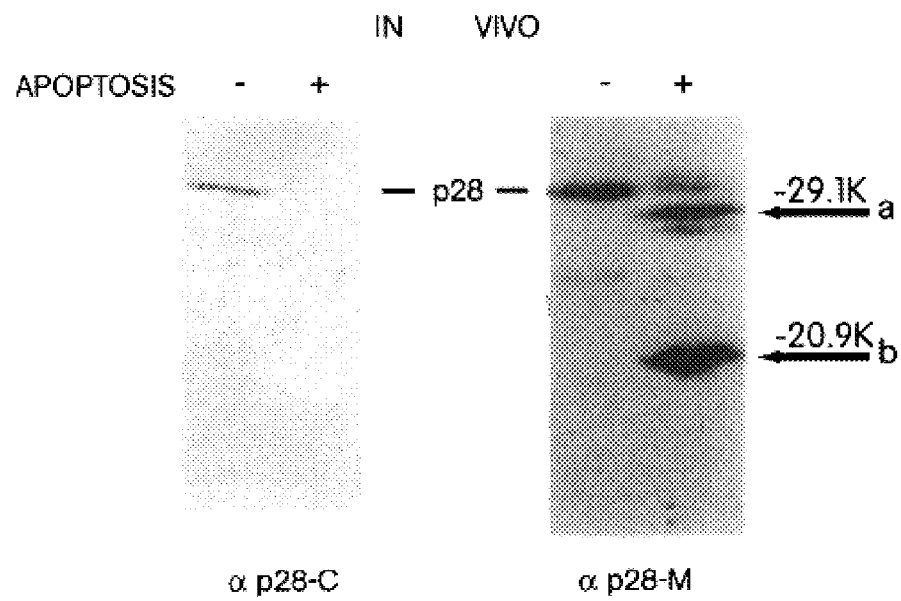
Figure 6A:
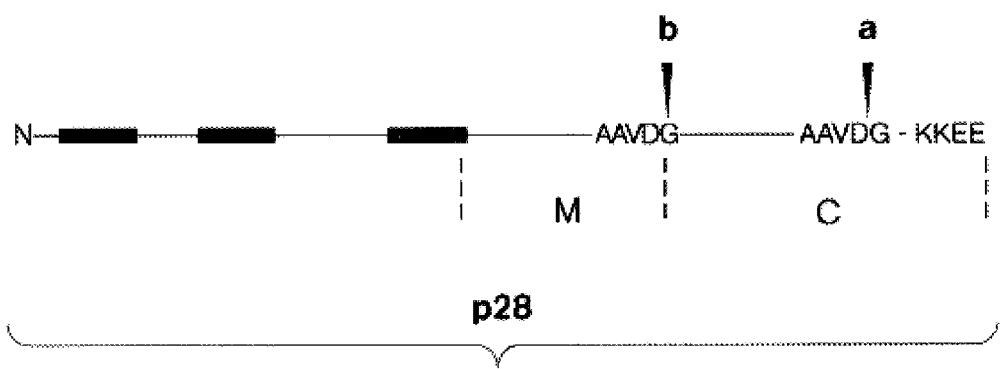

FIG. 6A shows two Western blotting analyses of cell extracts that were obtained from KB cells that had either been infected for 60 hours with adenovirus pm1716/2072 lacking expression of E1B 19K or had been mock-infected (+ or − apoptosis, respectively), probed with affinity-purified chicken antibody against p28 Bap31 amino acids 165–246 (α p28-C; left blot) or p28 Bap31 amino acids 122–164 (α p28-M; right blot). Bands corresponding to p28 Bap31 are indicated. Arrows labelled "a" and "b" denote products whose sizes are consistent with cleavage of p28 Bap31 at the sites designated "a" and "b" in the schematic shown in the lower panel below the blots.

Figure 6B:
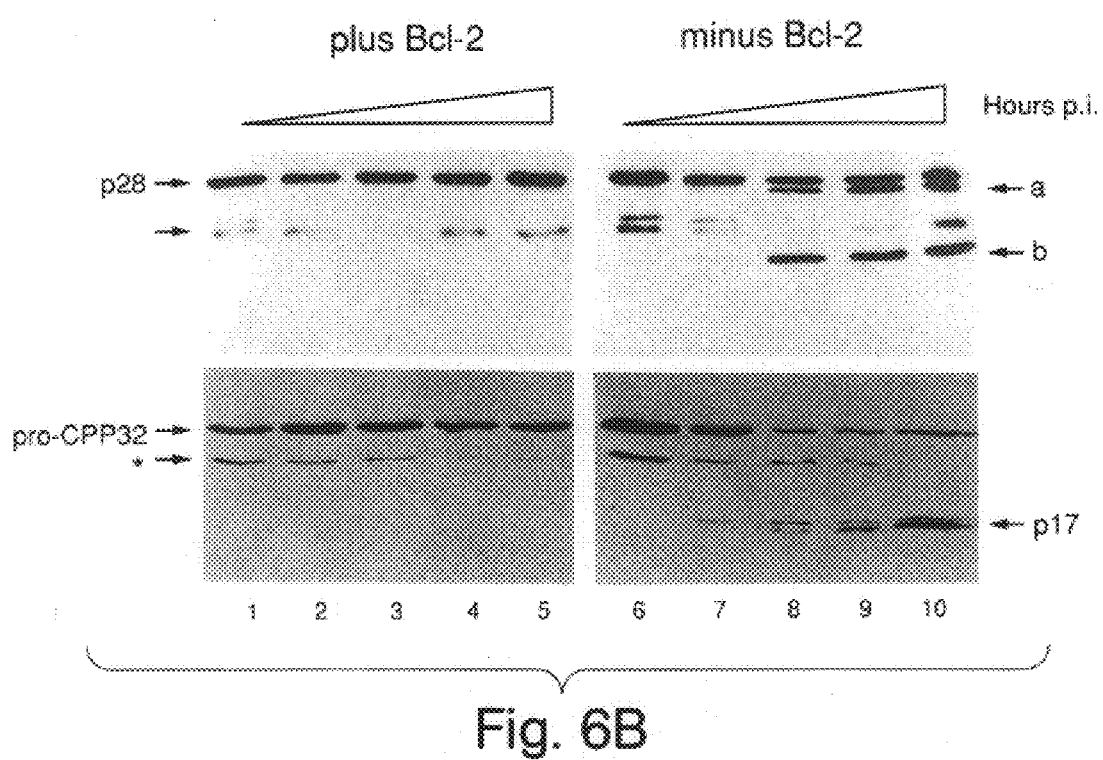

FIG. 6B shows a series of Western blotting analyses of cellular extracts prepared from KB cells expressing neomycin-resistance either alone (minus Bcl-2, lanes 6–10) or together with Bcl-2 (plus Bcl-2, lanes 1–5) infected with adenovirus pm1716/2072 lacking expression of E1B 19K, and probed with antibody against p28-M (upper two blots) or against the 17 kDa subunit of CPP32 (lower two blots; Boulakia et al., Oncogene 12: 529–535, 1996). The positions of p28 Bap31 and the cleavage products "a" and "b" are indicated in the upper two blots. The arrow in the upper left blot denotes a cross-reacting product whose appearance is variable (e.g., it did not appear in FIG. 6A). The positions of full-length pro-CPP32 and the processed 17 kDa subunit (p17) and putative 29 kDa processing intermediate (asterisk) are indicated in the lower two blots.

Figure 7A:
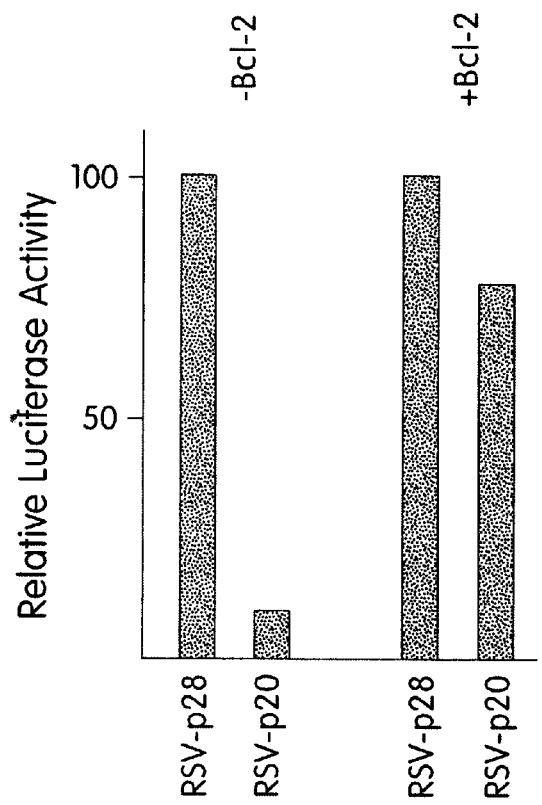

FIG. 7A is a graph showing the relative luciferase expression in CHO LR73 cells expressing neomycin-resistance, either alone (−Bcl-2) or together with Bcl-2 (+Bcl-2), that were co-transfected with a luciferase reporter plasmid and Rc/RSV expressing either full-length p28 Bap31 or p28 Bap31 amino acids 1–164 (i.e., p20). After 2 days, cells were recovered, analyzed for luciferase activity, and the enzyme activity expressed relative to the values obtained in the presence of p28 Bap31 (arbitrarily set at 100). The results shown are the average of two separate experiments.

Figure 7C:
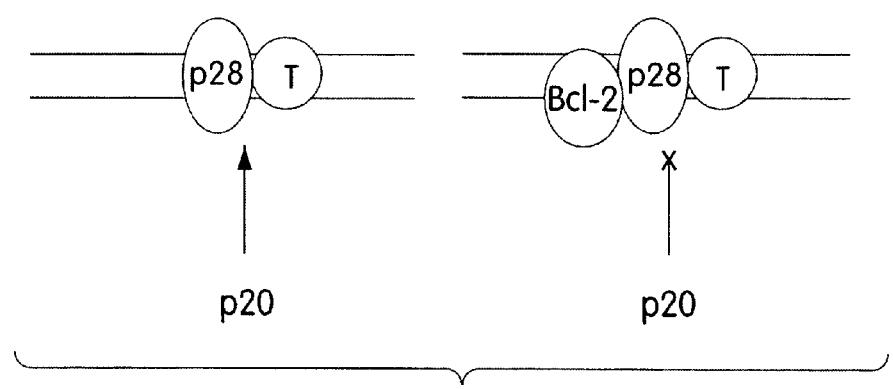
Figure 7B:
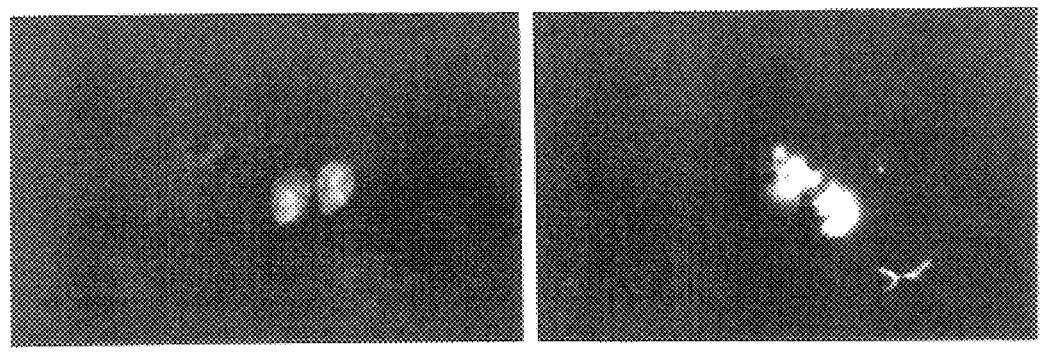

FIG. 7B are a set of photographs showing CHO cells transfected with the p28 Bap31 and p20 expression plasmids together with pHook (Invitrogen). 24 hours later, the transfected cells were recovered with Capture-Tec beads, cultured on coverslips, stained with 4',6'diamidino-2-phenyl indole (DAPI), and visualized under a microscope.

FIG. 7C is a schematic interpretation of the results of FIGS. 7A and 7B showing p28 Bap31 as part of a hypothetical complex with an interacting target, T.

Figure 8A:
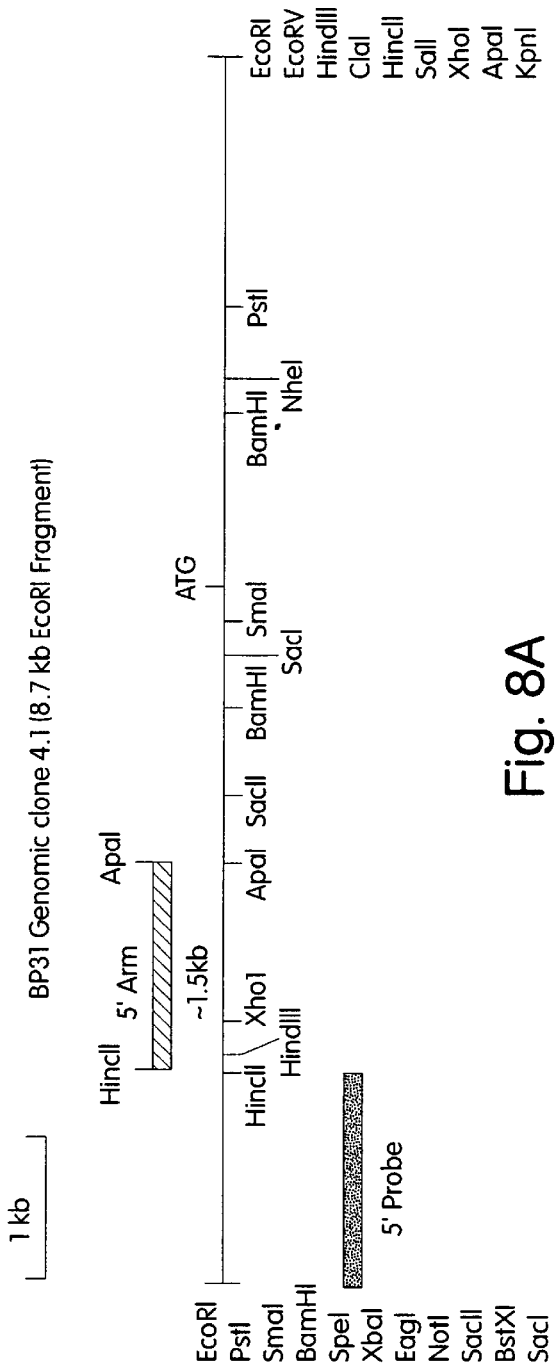
Figure 8B:
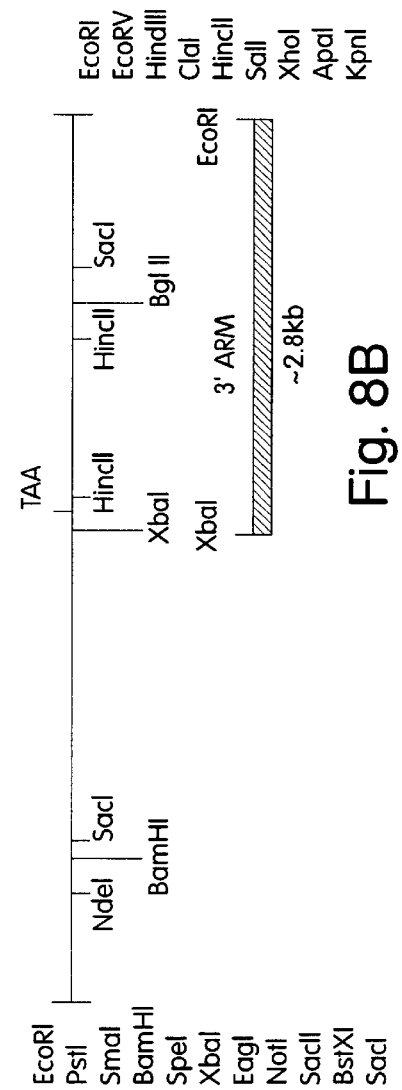
Figure 8C:
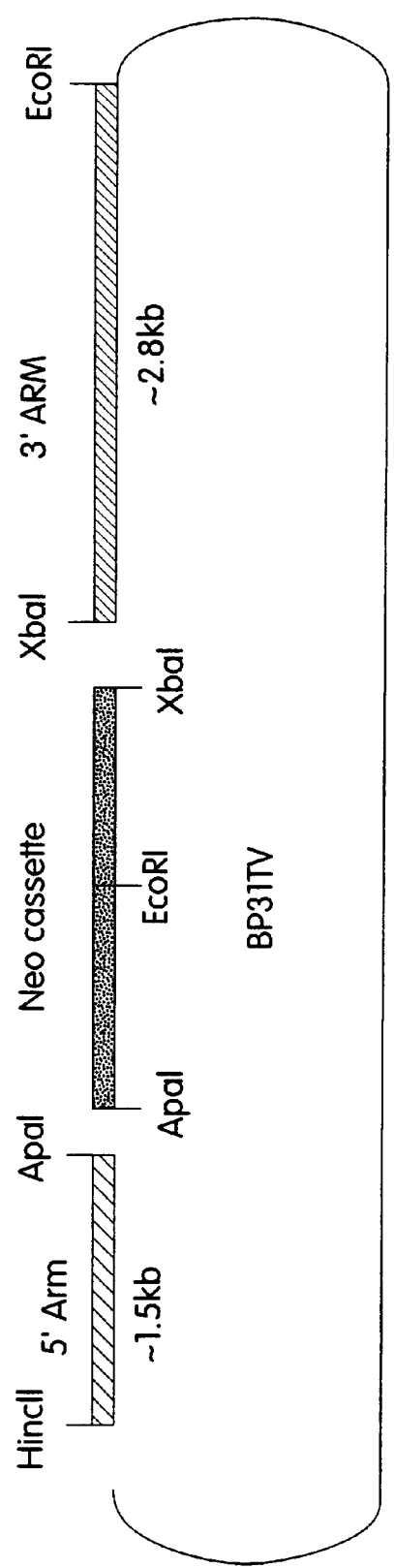

FIGS. 8A, 8B, and 8C are schematic diagrams showing the construction of the BP31 TV plasmid, which may be used to generate a p28 Bap31 knock out mouse.

Figure 9:
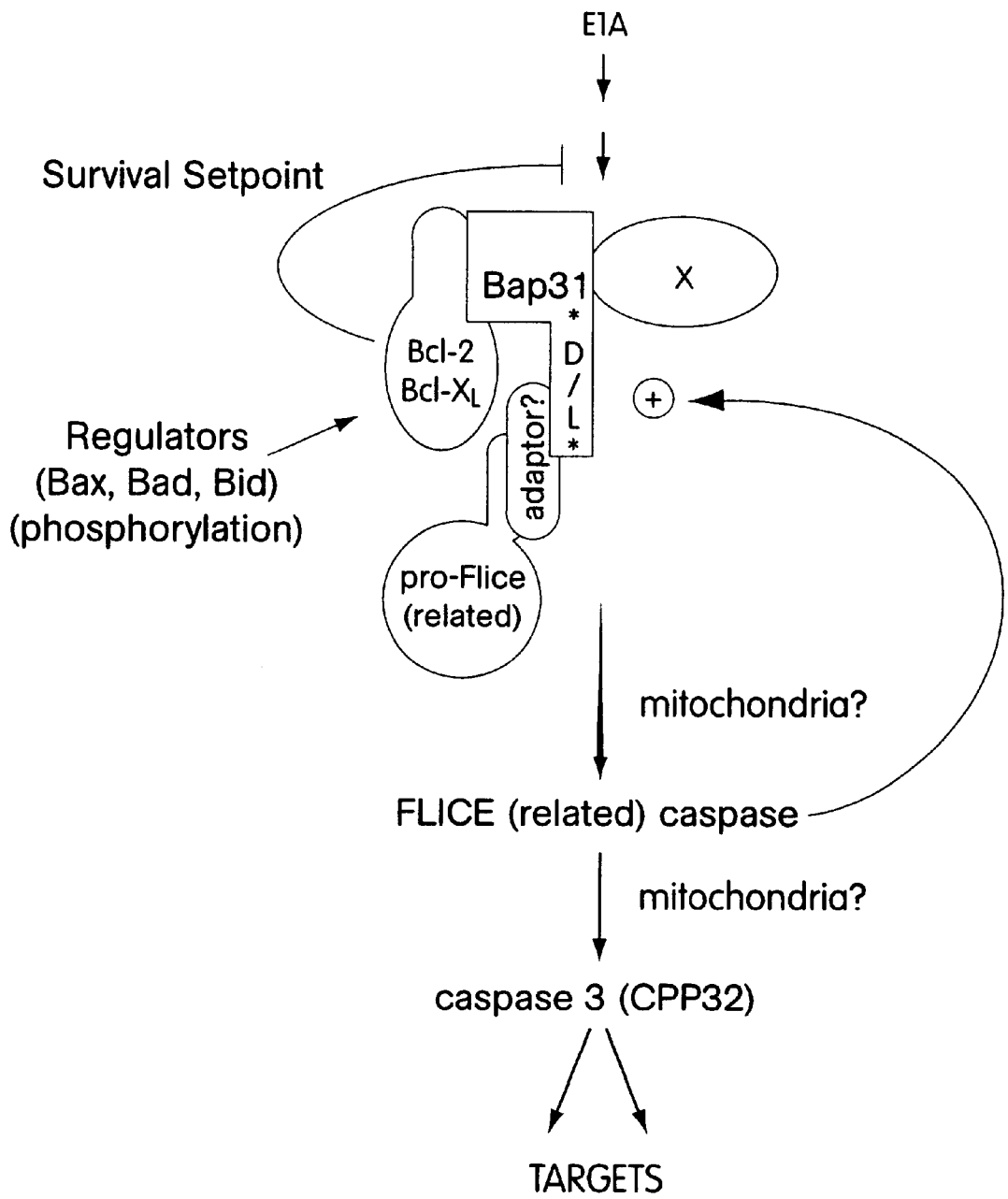

FIG. 9 is a schematic representation of a model for p28 Bap31 in the Bcl-2/caspase-apoptotic pathway.

DETAILED DESCRIPTION

The large pro-regions of initiator caspases contain a death effector domain that physically links these pro-enzymes to an apoptotic signalling complex. In the case of Fas (also known as CD95 or Apo-1) and the tumor necrosis receptor 1 (TNFR1) complexes, recruitment of pro-FLICE (FLICE has also been referred to as MACH or caspase-8) involves the adaptor molecule, FADD. This recruitment occurs via interactions between the death effector domains within the two molecules (Boldin et al., Cell 85: 803–815, 1996; Muzio et al., Cell 85: 817–827, 1996). Bcl-2 family member proteins are located in the endoplasmic reticulum (ER)/ nuclear envelope and mitochondrial outer membrane (Krajewski et al., Cancer Res. 53: 4701–4714, 1993; Nguyen et al., J. Biol. Chem. 268: 25265–25268, 1993; Gonzalez-Garcia et al., Development 120: 3033–3042, 1994) and, in the latter location, appear to prevent activation of downstream effector caspases such as procaspase-3 in response to diverse death signals.

We have now identified a Bcl-2/Bcl-$X_L$-interacting, polytopic integral membrane protein of the endoplasmic reticulum, p28 Bap31, that bears a canonical COOH-terminal ER retention motif in its cytosolic domain and that is part of a complex that contains Bcl-2 proteins and procaspase-8 (pro-FLICE). In the absence of Bcl-2, p28 Bap31 itself becomes a target of a ICE/FLICE-related caspase upon induction of apoptosis.

Appearance of a Bcl-2 Interacting Polypeptide Following Induction of Apoptosis

To detect potential Bcl-2-interacting polypeptides by Far Western blotting analysis, a $^{32}$P-labelled probe was constructed by expressing a modified version of the cytosolic domain of Bcl-2 in E. coli. To generate the modified Bcl-2 cytosolic domain, the last 21 amino acids of Bcl-2 were deleted and substituted with hexahistidine (his6) plus a heart muscle kinase (HMK) recognition peptide to facilitate purification and $^{32}$P-labeling, respectively. Isolation conditions were developed in which the recombinant protein was purified without the use of harsh denaturants, yielding a soluble product that included a mixture of monomers and dimers at pH 7.4, as judged by FPLC molecular sieve chromatography. The $^{32}$P-labelled probe ($^{32}$P-Bcl-2Δc2 1 /his6/HMK) readily detected either recombinant Bcl-2 or Bax as the only radioactive products on a Far Western blot of total bacterial lysate (not shown). When used as a probe to analyse potential Bcl-2-interacting polypeptides in cells induced to undergo apoptosis in response to various stimuli (including adenovirus E1A expression or treatment with puromycin), a product of approximately 20 kDa in size (p20) as judged by SDS PAGE was consistently observed.

Figure 1A:
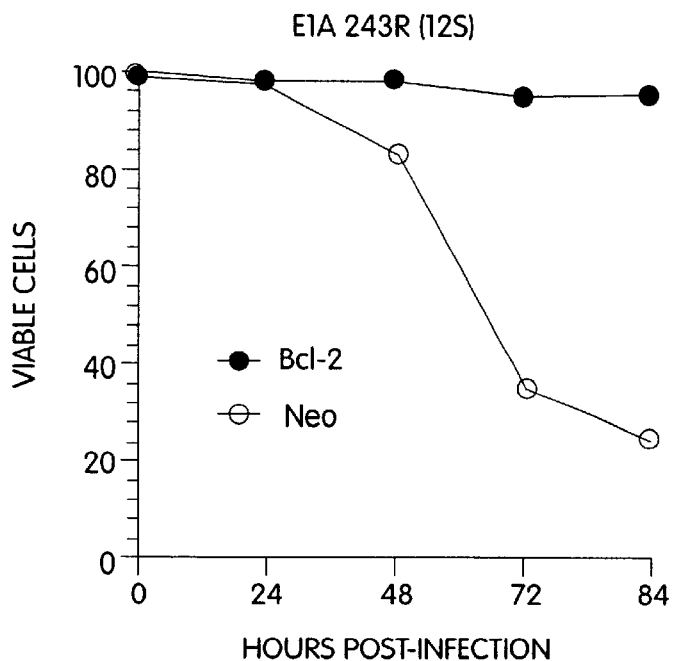
FIG. 1A is a graph showing the viability (as judged by exclusion of trypan blue at indicated times post-infection) of KB cells expressing neomycin-resistance, either alone (Neo) or together with Bcl-2, infected with adenovirus dl520E1B⁻ (expressing 12S E1A and no E1B products).
Figure 1B:
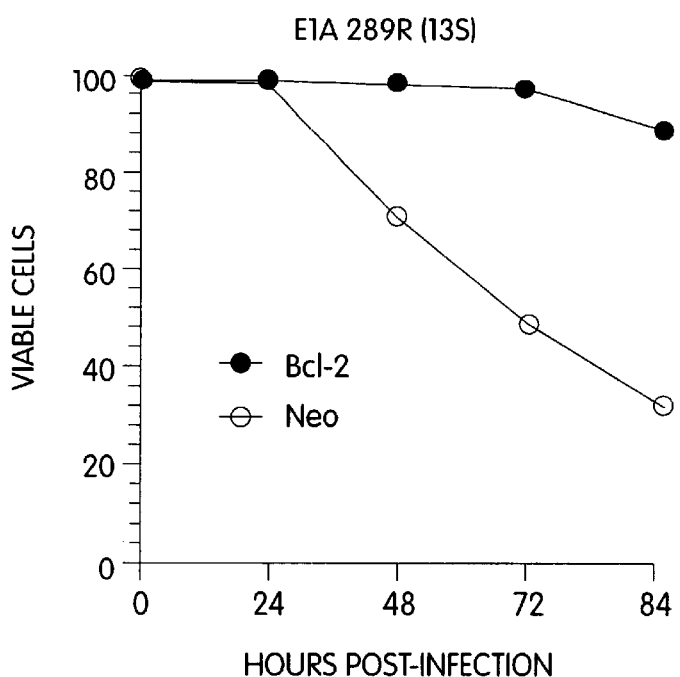
FIG. 1B is a graph showing the viability (as judged by exclusion of trypan blue at indicated times post-infection) of KB cells expressing neomycin-resistance, either alone (Neo) or together with Bcl-2, infected with adenovirus pm1760/2072 (expressing 12S and 13S E1A but not E1B 19K).
Figure 1C:
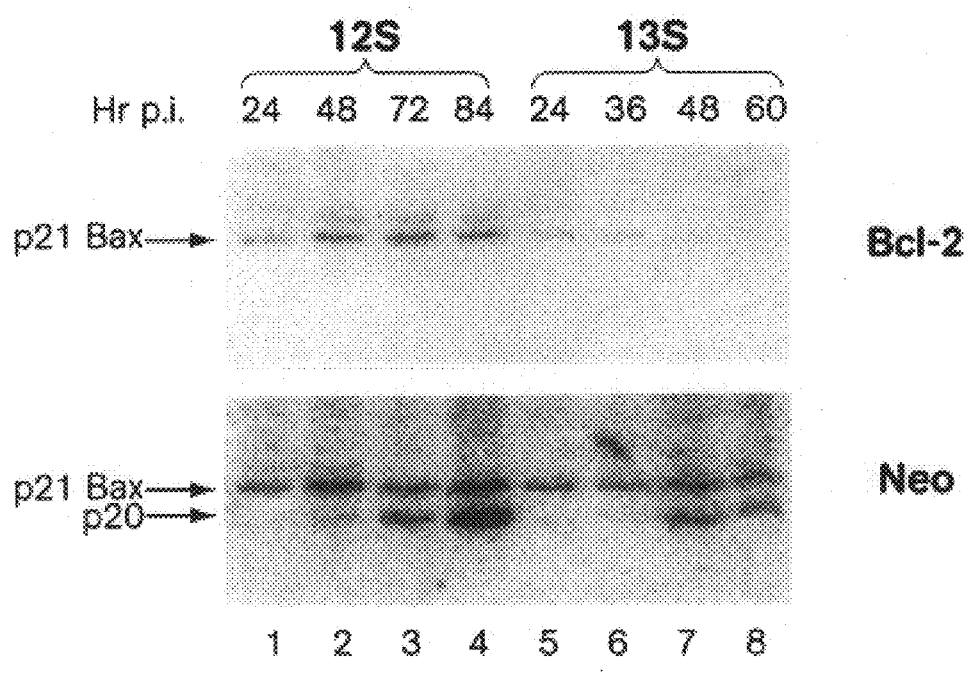
FIG. 1C is a Far Western blotting analysis showing the appearance of a Bcl-2 interacting polypeptide (probed with $^{32}P$-Bcl-2Δc21/his6/HMK) in total cellular protein prepared from KB cells expressing neomycin-resistance, either alone (Neo; lower panel) or together with Bcl-2 (upper panel), following infection at indicated times with either adenovirus dl520E1B⁻ (expressing 12S E1A and no E1B products; lanes 1–4) or adenovirus pm1760/2072 (expressing 12S and 13S E1A but not E1B 19K; lanes 5–8). The probe-reactive bands on the blots were visualized by phosphorimaging. The radioactive band associated with a polypeptide of $M_r$ 20 kDa is labelled p20, whereas that which co-migrates with Bax is labelled p21 Bax.

FIGS. 1A, 1B, and 1C show the appearance of a Bcl-2-interacting polypeptide during E1A-induced apoptosis. Samples of neo- and Bcl-2-expressing human KB cells were assessed for viability by exclusion of trypan blue (FIGS. 1A and 1B) or prepared for Far Western blotting analysis using $^{32}$P-Bcl-2Δc21/his6/HMK as a probe (FIG. 1C) at various times following infection. The neo- and Bcl-2-expressing human KB cells were infected with either adenovirus dl520E1B–, which expresses 12S E1A, but lacks expression of all E1B products (encodes the 243R E1A protein; FIG. 1A; lanes 1–4 of FIG. 1C), or adenovirus pm1760/2072, which expresses 12S and 13S E1A, but lacks expression of the dominant suppressor of apoptotic cell death, E1B 19 kDa protein (19K) (encodes both the 243R and 289R E1 A proteins; FIG. 1B; lanes 5–8 of FIG. 1C). Induction of apoptotic cell death by either virus (Nguyen et al., J. Biol. Chem. 269: 16521–16524, 1994; Teodoro et al., Oncogene 11: 467–474, 1995) was accompanied by the appearance of p20Bcl-2-binding activity. The radioactive band associated with a polypeptide of Mr 20 kDa is labelled p20 in FIG. 1C, whereas the band that co-migrates with Bax is designated p21Bax. Bax co-migration was determined using a blot cut along the vertical mid-line of a protein lane, and developing one half by Western blotting analysis with anti-human Bax (Chen et al., J. Biol. Chem. 271: 24221–24225, 1996) and the other by Far Western blotting analysis with $^{32}$P-Bcl-2Δc2l/his6/HMK (results not shown). Apparent binding of $^{32}$P-Bcl-2Δc21/his6/HMK to Bax did not alter significantly over the time course of infection (FIG. 1C). Of note, however, stable expression of Bcl-2 in KB cells countered cell death and prevented the appearance of p20Bcl-2-binding activity following viral infection (upper blot, FIG. 1C).

Identification of Bcl-2 Interacting p28 Bap31 and its Cleavage Product, p20

Figure 2A:
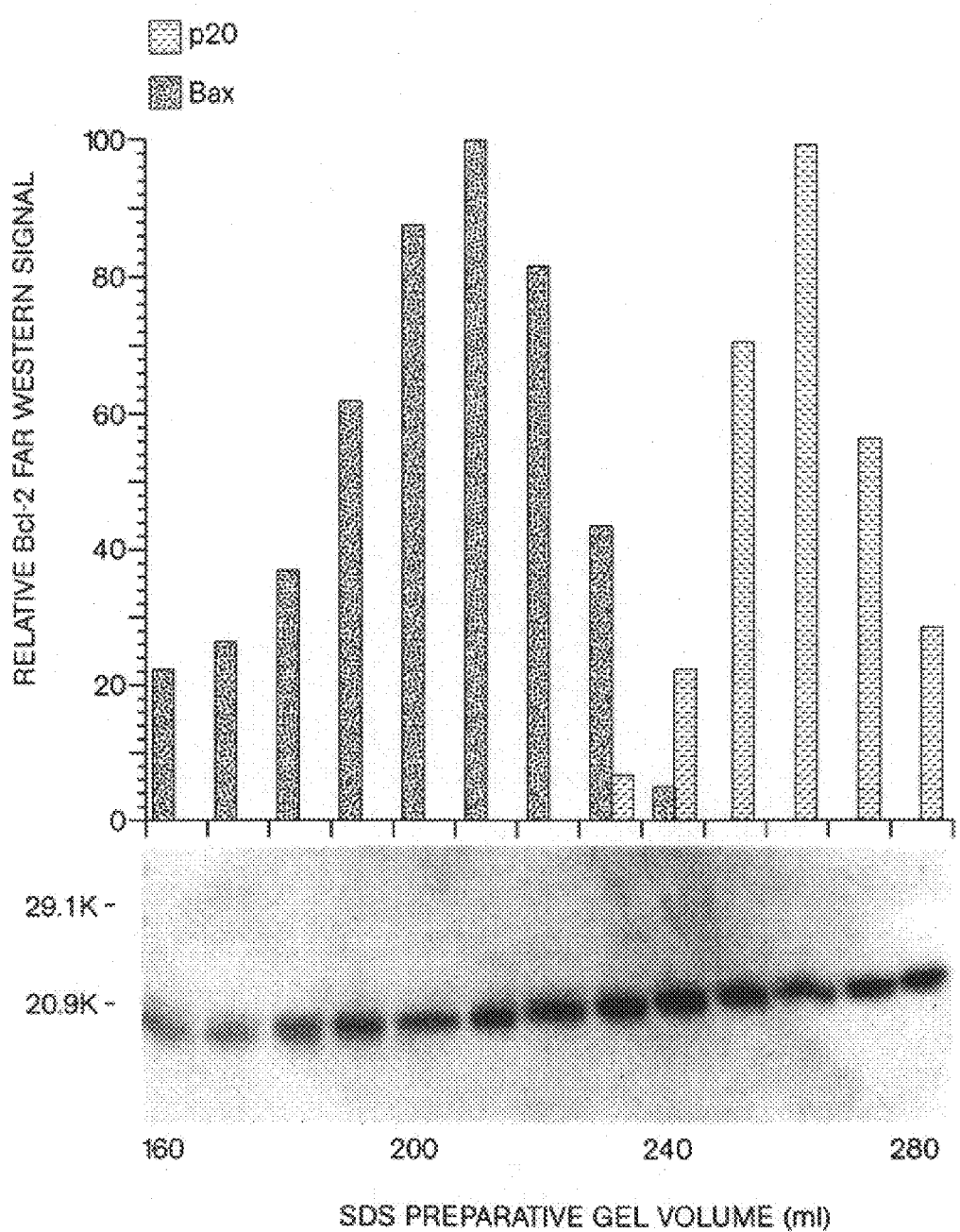
FIG. 2A shows a preparative SDS PAGE analysis (and a quantifying graph thereof) of differentially solubilized protein from KB cells 60 hours post-infection with adenovirus pm1760/2072. Aliquots of fractions eluted from the gel were assayed by $^{32}P$-Bcl-2Δc21/his6/HMK Far Western blotting analysis, and the radioactive bands corresponding to p20 and p21 Bax were detected and quantified by Phosphorimager. The levels relative to the maximal signal detected (set at 100) were plotted as a bar graph (upper panel). Equal aliquots from the same fractions were also subjected to analytical 12% SDS PAGE, and the gels stained with Coomassie brilliant blue (lower panel). The positions of molecular mass marker proteins are indicated. The black bars on the graph indicate p20. The white stippled bars on the graph indicate p21 Bax.
Figure 2B:
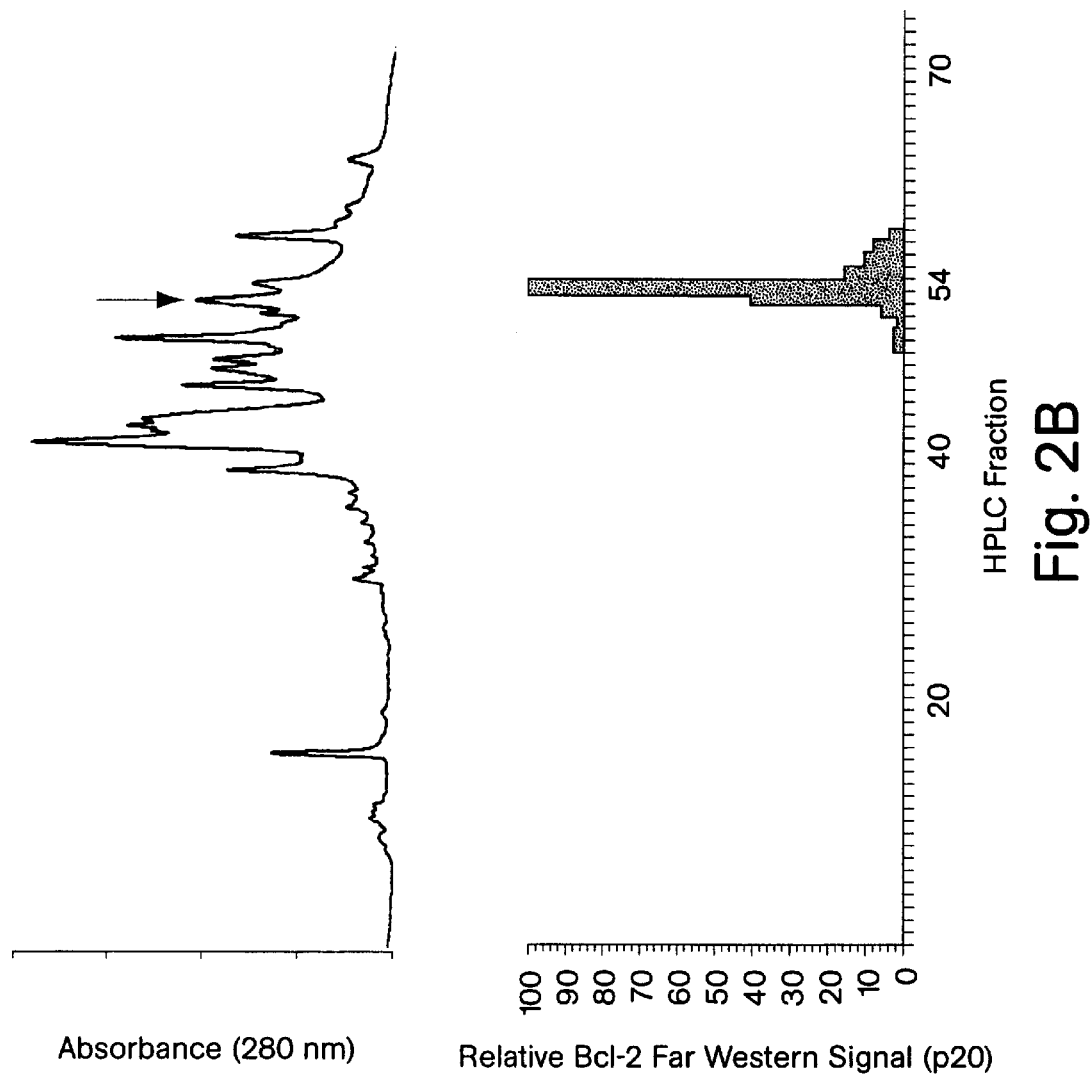
FIG. 2B is a reverse phase HPLC analysis ($A_{280}$ profile; upper panel) and corresponding graph (lower panel) showing proteins eluted between 190 and 220 ml from the preparative SDS PAGE of FIG. 2A. Equal aliquots from all fractions were assayed for $^{32}P$-Bcl-2Δc21/his6/HMK interacting protein by Far Western blotting analysis, for which only p20 was detected. Amounts relative to the maximal signal detected (set at 100) were plotted as a bar graph (lower panel). Fractions 52, 53, 54 (peak activity), and 55 were individually subjected to NH$_2$-terminal peptide sequence analysis.

Identification of the p20Bcl-2-binding polypeptide was obtained by NH$_2$-terminal peptide sequence analysis of p20 following its isolation by a combination of differential solubilization in detergent, preparative SDS PAGE, and reverse phase HPLC (FIGS. 2A and 2B). Several individual HPLC fractions were subjected to peptide sequence analysis in order to detect a polypeptide sequence whose appearance correlated with the appearance of p20Bcl-2 binding activity (FIGS. 2A and 2B). One candidate sequence emerged, and was the only sequence that was detected in the peak fraction of Bcl-2 binding activity (fraction 54, FIG. 2B). It showed a perfect match with amino acids 2–10 of human Bap31 (GenBank accession number X81817)/CDM (GenBank accession number Z31696), suggesting that p20 derives from the NH$_2$-terminus of Bap31/CDM, a 27,991 kDa (p28) protein (FIG. 2C). CDM was discovered because of its proximity to the adrenoleukodystrophy locus (Mosser et al., Genomics 22: 469–471, 1994) and Bap31 because it was one of several polypeptides that were found in immunoprecipitates of the B-cell receptor complex obtained from detergent solubilized cells (Kim et al., EMBO J. 13: 3793–3800, 1994; Adachi et al., EMBO J. 15: 1534–1541, 1996). RT PCR analysis of the p28 Bap31 coding region, using total RNA obtained from KB cells following induction of apoptosis, showed no evidence that p20 arose by differential splicing of p28 mRNA (data not shown). As demonstrated below, Bcl-2 also associates with full length p28 Bap31 in vitro and in vivo; failure to observe this interaction in the original ligand blot analyses (FIG. 1C) was likely the result of relatively inefficient transfer of p28 Bap31 to nitrocellulose blots.

Characterization of p28 Bap31

FIG. 2C highlights several predicted motifs in the human p28 Bap31 sequence. There are 3 potential transmembrane (TM) segments located in the NH$_2$-terminal half of the molecule (as detected using the method described in Kyte and Doolittle, J. Mol. Biol. 157: 105–132, 1982). TM1 and TM3 each contain charged residues. Additionally, two potential caspase cleavage sites, comprised of identical P1–P4 tetrapeptide recognition sequences (ala-ala-val-asp) plus a preferred small amino acid (gly) in the P1' position, are located at positions 164 and 238 in the polypeptide, on either side of a predicted leucine zipper domain (FIG. 2C) and overlapping homology to death effector domains found in such proteins as procaspase-8, procaspase-10, and FADD (FIG. 2D). Cleavage at the proximal caspase recognition site would generate a product (calculated M$_r$ (molecular mass) of 18.8 kDa) similar in size to p20. Interestingly, the distal caspase recognition site is lacking in the mouse p28 Bap31 sequence, however the proximal caspase recognition site, whose cleavage would generate an p20 product, is present in murine p28 Bap31 (FIG. 2D). Finally, the p28 Bap31 molecule terminates in lys-lys-glu-glu which conforms to a canonical KKXX COOH-terminal signal that retains integral ER proteins containing COOH-termini exposed to the cytosol within the ER, thus preventing their exit into the distal secretory pathway (Jackson et al., J. Cell Biol. 121: 317–333, 1993).

Figure 3A:
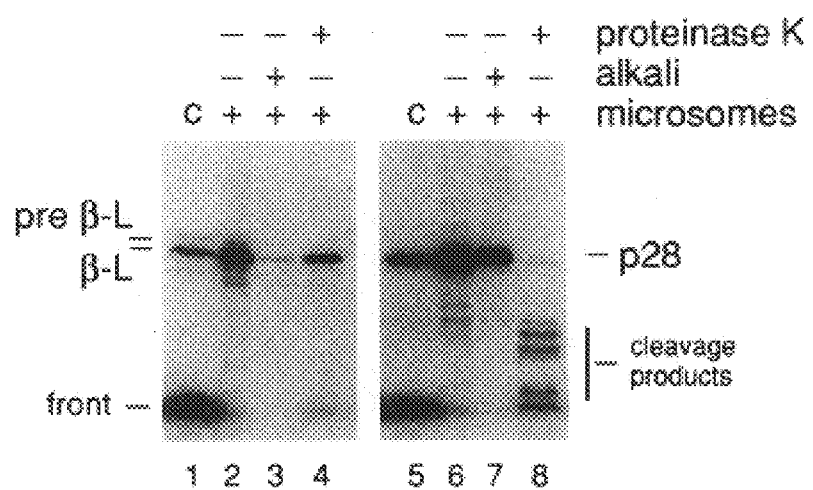
FIG. 3A is an SDS-PAGE analysis showing the insertion of p28 Bap31 into endoplasmic reticulum (ER) microsomes. The positions of p28 Bap31, pre-β-lactamase (pre-β-L), and processed β-lactamase (β-L) are indicated, as is the gel front. "c" indicates the marker translation product.

As shown in FIG. 3A, p28 Bap31 was efficiently inserted co-translationally into dog pancreas microsomes. Pre-β-lactamase (FIG. 3A, lanes 1–4) and p28 Bap31 (FIG. 3A, lanes 5–8) mRNA was translated in a rabbit reticulocyte lysate system in the presence of $^{35}$S-methionine, and in the presence (FIG. 3A, lanes 2–4 and 6–8) or absence (FIG. 3A, lanes 1 and 5) of ribosome-stripped canine pancreas microsomes (prepared according to the methods of Walter and Blobel, Meth. Enzymol. 96: 84–93, 1983). At the end of the reaction, microsomes were recovered and analyzed by SDS PAGE and autoradiography either directly (FIG. 3A, lanes 2 and 6) or following isolation of alkali-insoluble (NaCO$_3$, pH 11.5) product (FIG. 3A, lanes 3 and 7) (according to methods described in Nguyen et al., J. Biol.

Figure 3B:
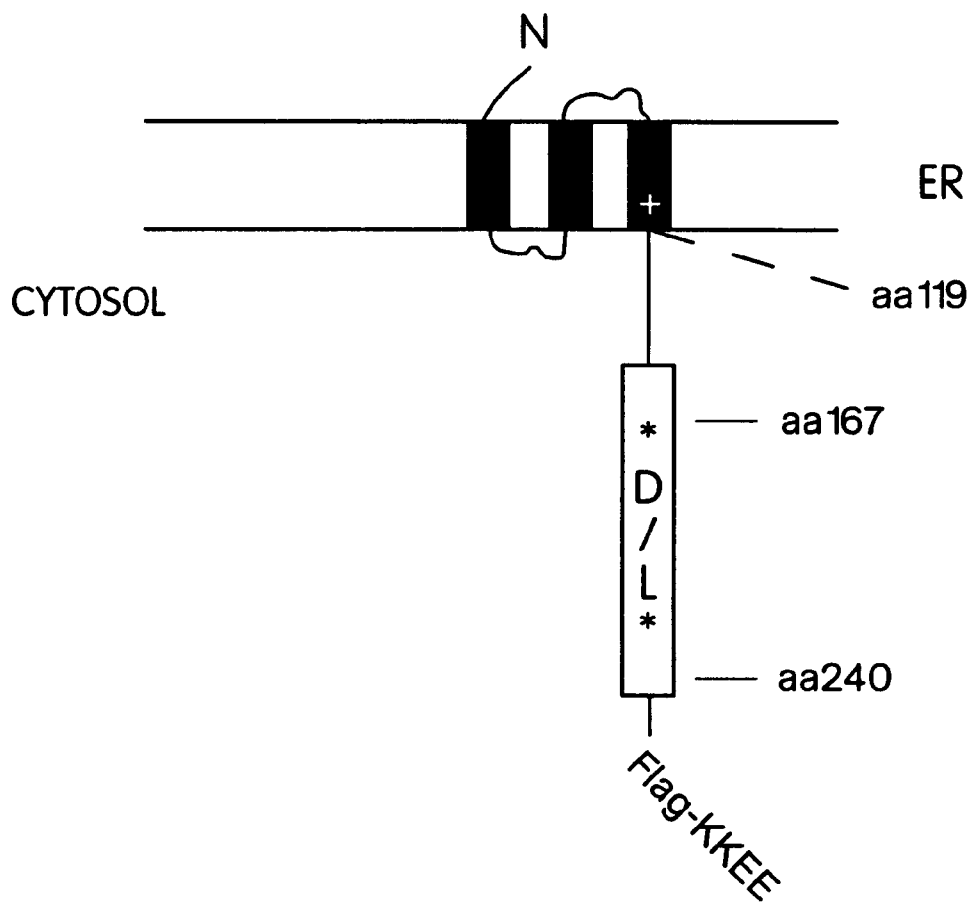
FIG. 3B is a schematic representation showing the deduced topology and domain structure of Flag-tagged p28

Chem. 268: 25265–25268, 1993), or following treatment with proteinase K (FIG. 3A, lanes 4 and 8) (according to methods described in McBride et al., J. Cell Biol. 119: 1451–1457, 1992). In contrast to β-lactamase, which was translocated across the ER membrane and deposited in the lumen as a soluble protein, p28 Bap31 was recovered as an integral protein following release from the ribosome. Whereas the processed form of β-lactamase was protected from external protease (FIG. 3A, lane 4) and liberated from microsomes by alkaline extraction (FIG. 3A, lane 3), p28 Bap31 was resistant to alkaline extraction (FIG. 3A, lane 7) and exhibited sensitivity to external protease (FIG. 3A, lane 8), resulting in the generation of proteolytic fragments which would be expected for a multi-spanning integral protein with an exposed cytosolic domain. Unlike β-lactamase, whose $NH_2$-terminal signal sequence was removed during translocation (FIG. 3A, compare lanes 1 and 4), processing of p28 Bap31 was not observed (FIG. 3A, compare lanes 5 and 6) suggesting that insertion into the microsomal membrane is initiated by an uncleaved signal anchor. Though not studied in detail, the observed properties of p28 Bap31 (FIG. 3A) together with predictions for the orientation of transmembrane segments in the ER based on charge-difference rules (as defined in von Heijne, G., J., Mol. Biol. 192: 287–290, 1986; Hartmann et al., Proc. Natl. Acad. Sci. USA 86: 5786–5790, 1989), suggests a topology for p28 Bap31 in the ER membrane in which the $NH_2$-terminus of this triple spanning polypeptide faces the lumen, leaving an approximately 13 kDa COOH-terminal fragment containing the predicted leucine zipper/death effector homology domain (amino acids 265–238) flanked on either side by sites that are cleaved by caspase-8 or related caspase during adenovirus E1A-induced apoptosis, and ER retention motif exposed to the cytosol. FIG. 3B shows a schematic diagram of p28 Bap31 that has been modified by the insertion of a Flag tag between pro 240 and met 241 of p28 Bap31 (i.e., the Flag tag was inserted immediately upstream of the C-terminal KKEE ER retrieval signal). Both biochemical fractionation and cryo-immunocytochemical electron microscopy confirmed that p28 Bap31 is predominantly located in the ER in rat hepatocytes (not shown).

Recombinant p28 Bap31 and p20 Interact with Bcl-2

Various p28 Bap31 fusion proteins were constructed in which glutathione S-transferase (GST) was linked to p28 Bap31 amino acids 1–246 (full length p28 Bap31), 1–164 (p20), 122–164, and 165–246. These constructs, together with GST itself, were purified and equal amounts examined for their ability to bind to the cytosolic domain of Bcl-2 in a Far Western blotting analysis assay. As shown in FIG. 4A, reactivity was observed for both GST-p28 Bap31 (FIG. 4A, lane 5) and GST-p20 (FIG. 4A, lane 4), with weak activity possibly registering with the COOH-terminal 165–246 amino acid domain (FIG. 4A, lane 2), and none detected for the middle 122–164 amino acid domain (FIG. 4A, lane 3) or for GST alone (FIG. 4A, lane 1).

Bcl-2 Proteins and Procaspase-8 (pro-FLICE) Associate with p28 Bap31 In Vivo

P28 Bap31 and its cleavage product, p20, associate with Bcl-2 in vitro. Thus, we attempted to detect the presence of a such a complex in vivo. Standard recombinant DNA manipulations were used to create cDNAs encoding Bcl-$X_L$ tagged at the C-terminus with the myc epitope, EQKLI-SEEDL (SEQ ID NO: 16; Chinnayan et al., Science 275: 1122–1126, 1997); pro-FLICE tagged at the C-terminus with the Hemagglutinen (HA) epitope, YPYDVPDYA (SEQ ID NO: 17; Chinnayan et al., Science 275: 1122–1126, 1997); Bcl-2 tagged at the N-terminus with the HA epitope (Nguyen et al., J. Biol. Chem. 269: 16521–16524, 1994); and p28 Bap31 tagged with the Flag epitope, in which the Flag sequence, MDYKDDDDKA (SEQ ID NO: 18), was inserted between pro 240 and met 241 of p28 Bap31 to avoid interference with the function of the ER retention signal in p28 Bap31 (i.e., the Flag tag was inserted immediately upstream of the C-terminal KKEE ER retrieval signal in p28 Bap31). The recombinant cDNAs encoding myc-tagged Bcl-$X_L$, HA-tagged pro-FLICE, or Flag-tagged p28 Bap31, or Flag DNA alone (Control-Flag), were inserted into the expression vector, pcDNA3 (commercially available from Invitrogen, Carlsbad, Calif.). The cDNA encoding HA-tagged Bcl-2 was inserted into the expression vector, RcRSV (commercially available from Pharmacia, Uppsala, Sweden). The resulting expression constructs were transfected into 293T cells, as is indicated in FIG. 4B (pluses and minuses), using the following procedure: 293T cells at 50–60% confluency in 10 cm culture plates were transfected by calcium phosphate precipitation with 15 μg total plasmid DNA and shocked with 15% glycerol 24 hours following transfection. Approximately 30 hours following transfection, the cells were washed in phosphate buffered saline (PBS) and homogenized in 1 ml lysis buffer (50 mM Hepes, pH 7.4, 150 mM NaCl, 1 mM ethylenediamine tetraacetate (EDTA), 0.5% v/v NP40, 10 μg/ml aprotinin, 1 mM phenylmethylsulfonyl fluoride (PMSF), and 10 μg/ml leupeptin) per 10 cm culture plate. After centrifugation at 11,000 g, the supernatant was incubated with 50 μl of a 1:1 slurry of protein G sepharose for 1 hour at 4° C. The sepharose was removed and the supernatant was incubated with mouse M2 anti-Flag antibody (commercially available from IBI Kodak) for 6–8 hours at 4° C., whereupon 20 μl of a 1:1 slurry of protein G sepharose was added. After another hour at 4° C., the beads were recovered, washed, and boiled in SDS sample buffer. Immunoprecipitates (ip) and boiled lysates (cell lysates prior to imunoprecipitation with the anti-Flag antibody) were resolved by SDS-PAGE, transferred to nitrocellulose, and probed with the indicated antibody directed toward either myc or HA, and are commercially available from Babco (Berkeley, Calif.). Immunoreactive bands were visualized by electrochemiluminescence of the immunoglobulin heavy chain (Ig HC).

Shown in FIG. 4B are the results of the Western blotting analysis of the lysates and immunoprecipitations probed with anti-Myc or anti-HA antibodies. As judged by the co-immunoprecipitation, Bcl-$X_L$, pro-FLICE, and Bcl-2 each demonstrated a specific association with p28 Bap31, as shown in FIG. 4B, lanes 3, 8, and 14, respectively. Pro-FLICE was observed as a doublet band that migrated immediately below the Ig heavy chain; transcription translation of the cDNA in vitro was found to likewise generate a doublet of similar size (not shown). Interestingly, Bcl-$X_L$ and pro-FLICE, when expressed in combination, did not mutually antagonize each other's ability to associate with p28 Bap31 (see FIG. 4B, lanes 5 and 10; note the lower input levels of Bcl-$X_L$ in the cell lysate in lane 5). Although some activation of wild-type procaspase-8 might be expected, the full length pro-enzyme was readily detectable at similar levels in both the presence and absence of Bcl-$X_L$ (FIG. 4B, lanes 8 and 10).

Finally, the pro-apoptotic member of the Bcl-2 family, Bax (Oltvai et al., Cell 74: 609–619, 1993), did not co-immunoprecipitate with p28 Bap31 following their co-expression in 293T cells (FIG. 4C, lane 5), despite the fact that significant expression levels of transfected Bax were recorded (FIG. 4C, lanes 2 and 3). However, Bax prevented Bcl-2 from associating with p28 Bap31 (FIG. 4C, compare lanes 11 and 12). Although the level of Bcl-2 in cell lysates was somewhat lower in transfectants containing Bax (FIG. 4C, compare lanes 8 and 9), such a level of Bcl-2 would otherwise have been sufficient to readily detect co-immunoprecipitation of Bcl-2 and p28 Bap31.

p28 Bap31 is Cleaved to p20 Following Induction of Apoptosis

Although we demonstrated that p28 Bap31 was cleaved into a product, p20, in a cell that had been induced to undergo apoptosis, the exact mechanism by which this cleavage occurred was unknown. To determine whether or not the caspase recognition sequences (AAVDG) in p28 Bap31 were in fact recognized by one or more of the caspases, a $^{35}$S-labelled p28 transcription-translation product of p28 Bap31 cDNA was generated by $^{35}$S-methionine labelling in vitro translated proteins according to the methods known in the art (see, for example, Ausubel et al., Current Protocols in Molecular Biology, John Wiley & Sons, New York, N.Y., 1994) using $^{35}$S-labelled methionine commercially available from Dupont/NEN. This $^{35}$S-labelled p28 was incubated with increasing concentrations of caspase-3 (CPP32) or caspase-1 (ICE) in vitro (according to the methods of Nicholson et al., Nature 376: 37–43, 1995), and the products examined following resolution on SDS-PAGE. As can be seen in FIG. 5A (upper blot), little reactivity was observed for caspase-3 over a wide range of enzyme concentration. ICE (caspase-1), on the other hand, generated two products (denoted "a" and "b" in the schematic diagram at the bottom of FIG. 5A) whose apparent sizes in SDS gels (approximately 27 kDA and 20 kDa, respectively) were more consistent with cleavage occurring at both AAVDG caspase recognition sequences (FIG. 5A, lower blot). Similar analysis was made by incubating $^{35}$S-methionine labelled p28 with FLICE and ICE, although in this experiment, the amount of the resulting p20 cleavage product was quantitated on a Phosphorimager. As shown in FIG. 5B, it is noteworthy that p28 Bap31 was more sensitive to cleavage by FLICE (caspase-8) than ICE (caspase-1).

Two cleavage products of p28 Bap31, similar in size to those seen in vitro (see FIG. 5A), were observed in KB cells that had been induced to undergo apoptotic cell death in response to infection by 19K-defective adenovirus (FIG. 6A). In FIG. 6A, p28 Bap31 cleavage during apoptosis in vivo was analyzed using antibodies raised in chicken to either of two regions of the protein: p28 Bap31 amino acids 122–164 (α p28-M) and 165–246 (α p28-C). Following resolution of cellular extract proteins by 12% SDS PAGE and transfer to nitrocellulose, the blots were incubated with the primary chicken antibody, and then developed with secondary antibody conjugated either to horseradish peroxidase and visualized by electrochemiluminescence (Amersham Intl., Arlington Heights, Ill.) (for α p28-M, right blot) or to alkaline phosphatase and visualized with NBT/BCIP (Boehringer Mannheim Biochemicals, Indianapolis, Ind.) (α p28-C; left blot), according to the manufacturer's instructions. Of note, cleavage products were detected with α p28-M but not with α p28-C, a finding consistent with the suggestion from peptide sequence analysis that the p20 cleavage product derives from the $NH_2$-terminus of p28 Bap31 (see FIG. 2C). α p28-C also failed to detect the larger of the two cleavage products (designated "a" in FIG. 6A) despite the predicted overlap of this product with the protein sequence injected into chickens. Presumably, this means that the extreme 8 amino acids of p28 Bap31 are critically important for epitope recognition by this antibody. Finally, protein electrophoretic blots were developed from apoptotic cell extracts, cut in half along the vertical midline of a protein lane, and one half probed with α p28-M and the other with $^{32}$P-Bcl-2Δc21/his6/HMK. p20 detected by Far Western blotting analysis migrated exactly with p20 detected by α p28-M immunoblotting (data not shown).

In FIG. 6B, the effect of Bcl-2 on the appearance of p28 Bap31 cleavage products following cell infection with 19K-deficient adenovirus was examined using the a p28-M antibody. Cellular extracts were prepared at 0 hours (FIG. 6B, lanes 1 and 6), 24 hours (FIG. 6B, lanes 2 and 7), 36 hours (FIG. 6B, lanes 3 and 8), 48 hours (FIG. 6B, lanes 4 and 9), and 60 hours (FIG. 6B, lanes 5 and 10) post-infection (p.i.) from KB cells expressing neo plus Bcl-2 (FIG. 6B, lanes 1–5) or neo only (FIG. 6B, lanes 6–10). Aliquots (15 μg protein) were subjected to 12% SDS-PAGE, transferred to nitrocellulose, and probed, and visualized as described above for the results pictured in FIG. 6A. In the absence of Bcl-2 expression, the time course of appearance of these products closely followed the time course for activation of pro-CPP32, as judged by processing of the pro-enzyme to the p17 subunit of CPP32 (FIG. 6B, lanes 6–10). However, both p28 Bap31 cleavage and pro-CPP32 processing were blocked in virus-infected cells that express Bcl-2 (FIG. 6B, lanes 1–5).

Ectopic Expression of p20 Induces Apoptosis in Transfected KB Cells

CHO (neo) cells were transiently co-transfected with a luciferase reporter gene together with RcRSV expressing either p28 Bap31 or p20. Subsequent measurements revealed that co-expression of p20 with the reporter severely depressed the amount of luciferase activity obtained relative to co-expression with p28 Bap31 (FIG. 7A). p28 Bap31, on the other hand, had no deleterious effect on the recovery of luciferase activity compared to a control RcRSV plasmid that did not encode protein (not shown). If these same transfections were conducted in KB cells stably expressing Bcl-2, however, Bcl-2 largely overcame the dominant negative influence of p20 on luciferase activity (FIG. 7A), presumably because p20 could no longer interfere with normal p28 Bap31 function. Because of this protective effect by Bcl-2, we concluded that the negative influence of p20 on luciferase activity was the result of induction of apoptotic cell death. This was confirmed by microscopic analysis, which revealed dying cells with condensed apoptotic nuclei in p20-, but not p28 Bap31-transfected cells (FIG. 7B). The findings described in FIG. 7A, and the above-mentioned microscopic analysis (FIG. 7B) have been consistently observed many times and in different cell types. Hence, the p20Bap31 product is a potent inducer of apoptosis when expressed ectopically in otherwise normal cells, presumably because it has a dominant-negative effect on endogenous p28 Bap31.

A p28 Bap31 Knockout ES Cells and Mouse Models: Construction of a Transgenic Animal P28 Bap31 gene characterization provides information that is necessary for p28 Bap31 knockout animal models to be developed by homologous recombination. Preferably, the models are mammalian animals, most preferably mice. Similarly, an animal model of p28 Bap31 overexpression may be generated by integrating one or more p28 Bap31 gene sequences into the genome, according to standard transgenic techniques.

A replacement-type targeting vector, which may be used to create a knockout model, may be constructed using an isogenic genomic clone, for example, from a mouse strain such as 129/Sv (Stratagene Inc., La Jolla, Calif.). The targeting vector may be introduced into a suitably-derived line of embryonic stem (ES) cells by electroporation to generate ES cell lines that carry a profoundly truncated form of a p28 Bap31 gene. The targeted cell lines may then be injected into a mouse blastula stage embryo to generate chimeric founder mice. Heterozygous offspring may be interbred to homozygosity. Knockout mice provide the means, in vivo, to screen for therapeutic compounds that modulate apoptosis via a pathway that involves p28 Bap31. Making such mice may require use of loxP sites if there are multiple copies of p28 Bap31 on the chromosome (see Sauer and Henderson, Nucleic Aids Res. 17: 147–61, 1989).

Hence, to further assess the role of p28 Bap31 at an organismal level, the generation of a mouse lacking the p28 Bap31 -encoding gene is desired. To achieve this, a plasmid bearing a "knock-out" version of the murine p28 Bap31 gene, such as the plasmid shown as schematic diagrams in FIGS. 8A, 8B, and 8C, may be used. The resulting plasmid, BP31TV, is shown in a schematic diagram in FIG. 8C, and bears a gene, "p28 Bap31-NEO" that encodes a protein capable of resisting the presence of neomycin (i.e., G418).

The BP31 TV was then transfected into embryonic stem cells (ES cells) from a mouse. Once homologous recombination of the BP31 TV DNA with genomic DNA is detected, the clone of ES cells bearing this homologous recombination is used to produce mice that are heterozygous and homozygous for a Bap31 knock-out mutation. It will be appreciated that the ES cells are, themselves, useful, e.g., for identifying compounds which mimic p28 Bap31 in culture.

It will be understood that once such an ES cell genetically engineered to lack an endogenous p28 Bap31 gene is generated, the cell may be further manipulated to express a mutated or truncated version of p28 Bap31. Nucleic acid encoding such a truncation or deletion may be generated by standard techniques, and introduced into a plasmid. The plasmid may then be introduced by artifice into the ES cells bearing the p28 Bap31-NEO gene at the locus normally bearing the endogenous p28 Bap31 gene. ES cells both lacking an endogenous p28 Bap31 gene and expressing a truncated or mutated p28 Bap31 are able to grow in culture media containing both G418 and hygromycin (commercially available from Sigma). The cells may be analyzed, or used to generate a transgenic mouse lacking expression of endogenous p28 Bap31 and expressing a truncated or mutated form of the protein.

The cooperative associations between Bcl-$X_L$, procaspase-8, and the p28 Bap31 cytosolic domain described herein suggest that Bap31 may provide a mechanism by which corresponding molecular complexes in mammalian cells are linked to the multitude of signals that can trigger activation of procaspases, and how they interface with the numerous proapoptotic and antiapoptotic regulators that modulate these signals. Without wanting to be limited to a particular hypothesis, we propose a working model (FIG. 9) in which apoptotic signalling induced by E1A expression and/or other Bcl-2-inhibiting events leads to activation of the caspase cascade by a pathway that involves p28 Bap31. One of the activated caspases (e.g., FLICE) then cleaves p28 Bap31 to produce p20, an event that may act to consolidate and amplify the commitment to apoptosis. By interacting with full length p28 Bap31 (and perhaps other targets), Bcl-2 abrogates activation of the caspase proteases and blocks apoptosis.

Experimental Procedures

Cells and Viruses

Human epithelial KB cells expressing the neomycin resistance gene (neo) either alone or together with Bcl-2 (Nguyen et al., J. Biol. Chem. 269: 16521–16524, 1994) were cultured in α-MEM supplemented with 10% fetal bovine serum, and 100 units/ml streptomycin and penicillin. After reaching 80% confluency, the medium was replaced with fresh medium containing either no virus or 25–35 plaque forming units (pfu)/cell of adenovirus type 5 lacking expression of E1B 19K (pm1716/2072, McLorie et al., J. Gen. Virol. 72: 1467–1471, 1991) or of adenovirus type 5 expressing only the 243R-form (12S) of E1A and no E1B products (dl520E1B–) (Shepherd et al., J. Virol. 67: 2944–2949, 1993). Following incubation for 1 hour at 37° C., fresh medium was added and cells were collected at various times for analysis. Both forms of the virus elicit a cytotoxic response in infected cells which exhibit all of the hallmark features of apoptosis (Nguyen et al., J. Biol. Chem. 269: 16521–16524, 1994; Teodoro et al., Oncogene 11: 467–474, 1995).

Bacterial Expression and Purification of $^{32}$P-labelled Bcl-2 Cytosolic Domain for Ligand Blot (Far Western) Analyses cDNA encoding the cytosolic domain of human Bcl-2 (i.e., lacking the COOH-terminal 21 amino acids) was inserted into the pTrchis vector (Invitrogen), and standard PCR methodology employed to extend hexahistidine at the COOH-terminus to include a heart muscle kinase recognition sequence using the oligonucleotides 5'-CTAGCGCCCGCCGCGCCTCTGTGGAATTCTGAA-3' (SEQ ID NO: 19) and 5'-AGCTTTCAGAAT TCCACAGAGGCGCGGCGGGCG-3' (SEQ ID NO: 20). The final construct encoded Bcl-2 (amino acid residues 1–218), hexahis, arg, arg, ala, ser —COOH, and the protein was designated Bcl-2Δc21/his6/HMK. The Bcl-2 portion contained three additional mutations which were introduced for reasons not related to this project (met 16 to leu; lys 17 to arg; lys 22 to arg). Stable epithelial cell lines that express full-length Bcl-2 harboring these mutations were found to be as effective as cells expressing wild-type Bcl-2 in countering apoptotic death stimuli.

E. coli MC1061 was transformed with pBcl-2Δc21/his6/HMK. When 500 ml cultures reached 0.6 $A_{600}$ of 0.6, they were treated with 1.0 mM IPTG, and cells recovered by centrifugation 4 hours later. Packed cells (2.5–3.0 ml) were suspended in 15 ml extraction medium (20 mM Na phosphate, pH 7.4, 0.5 M NaCl, 0.05% v/v Triton X-100, 10 mM β-mercaptoethanol, 1.0 mM phenylmethylsulfonylfluoride, and 1.0 mM benzamidine) and sonicated 8× with a Vibra Cell probe sonicator (Sonics and Materials, Inc., Danbury, Conn.) operating at setting 7.5 for 15 seconds at 4° C. The sonicate was adjusted to 10% (v/v) glycerol and centrifuged at 25,000 rpm for 30 minutes at 4° C. in a Beckman Ti 50.2 rotor (Beckman Instruments, Inc., Fullerton, Calif.). The supernatant was added to 1.2 ml $Ni^{2+}$-NTA agarose (commercially available from QIAGEN Inc., Chatsworth, Calif.) (a 1:1 (v/v) mixture with extraction medium) and incubated for 1.5 hours at 4° C. The beads were washed extensively in extraction medium containing 20% (v/v) glycerol and 22 mM imidazole, and Bcl-2Δc21/his6/HMK eluted in extraction medium containing 20% glycerol and 0.3M imidazole. One liter of induced culture yielded 0.8–1.0 mg protein which was greater than 95% pure. The purified protein was labelled with $^{32}$P following incubation with heart muscle kinase and $^{32}$P-γ-ATP, yielding 2.0–2.5×$10^6$ cpm/μg protein, and was employed for ligand blotting, as described in Blanar and Rutter (Science 256: 1014–1018, 1992).

Purification and Identification of p20 Fragment

KB cells were cultured in 20 15-cm plates until 80% confluent, and infected with 25 plaque forming units (pfu)/cell of adenovirus type 5 lacking expression of E1B 19K (pm1716/2072). After 60 hours, total cells (65–70% nonviable, as judged by exclusion of trypan blue) were collected, rinsed, and the packed cells (approximately 1.5 ml) suspended in ice-cold 6 ml lysis medium containing 10 mM Tris HCl, pH 7.5, 140 mM NaCl, 1.5 mM $MgCl_2$, 0.5% Triton X-100 and 1 mM phenylmethylsulfonylfluoride) and separated into 3 equal portions. Each was subjected to sonication for 4×10 sec using an Artek probe sonicator operating at setting 6.0 (Artek Systems Corp., Farmingdale, N.Y.). The combined sonicates were centrifuged at 11,000×g for 20 minutes and the supernatant mixed with 0.25 vol of 5×SDS sample buffer (250 mM Tris HCl, pH 6.8, 50% glycerol, 0.5% bromophenol blue, 10% SDS and 1M dithiothreitol). The total volume was subjected to preparative 14% SDS-PAGE using a Bio Rad Prep Cell 491 system (Bio Rad Laboratories, Hercules, Calif.) fitted with a 37 mm diameter resolving gel chamber. Fractions were collected at a flow rate of 1 ml/min, assayed for the presence of p20 by ligand blotting using $^{32}$P-Bcl-2Δc21/his6/HMK as probe, and the reactive peak fractions combined and concentrated approximately five-fold in a Centriprep-10 concentrator (commercially available from Amicon, Inc., Beverly, Mass.). The concentrated sample was mixed with an equal volume of 0.12% trifluoroacetic acid and subjected to reverse phase HPLC in a Hewlett Packard 1090 System (Hewlett Packard CO., Palo Alto, Calif.) outfitted with a Vydac C4 column (0.21×20 cm) (The Nest Group, Inc., Southboro, Mass.) prefixed with two SDS removal cartridges (2.1×20 mm). The column was developed with a linear gradient of 0 to 80% n-propyl alcohol containing 0.12% trifluoroacetic acid at a flow rate of 0.1 ml/min, and monitored at $A_{280}$. Fractions (0.1 ml) were collected and those containing Bcl-2-reactive p20, as judged by ligand blotting, were individually subjected to $NH_2$-terminal peptide sequence analysis at Harvard Microchem (Harvard University, Cambridge, Mass.).

Cloning of p28 Bap31/CDM cDNA

The coding region of p28 Bap31 was cloned by reverse transcriptase-polymerase chain reaction (RT-PCR) using human fibroblast RNA together with primers derived from the sequence of human BAP31 (EMBL accession number X81817). Conditions were exactly as described in Goping et al. (FEBS 373: 45–50, 1995) and used as the anti-sense primer, 5'-TCTCTAGAACAAACAGAAGTACTGGA-3' (SEQ ID NO: 21) and as the sense primer, 5'-GATCTAGACATCTTCCTGTGGGAA-3' (SEQ ID NO: 22). Authenticity was confirmed by DNA sequence analysis.

Glutathione S-Transferase (GST) Fusion Proteins

PCR was employed to generate cDNA fragments corresponding to p28 Bap31 amino acids 1–246 (full-length), 1–164, 122–164, and 165–246, using primers that contained either 5'-BamH1 or 3'-EcoR1 overhangs, respectively. The primers were 5'-GCGGATCCATGAGTCTG CAGTGGACT-3' (SEQ ID NO: 23) and 5'-GCGAAT TCTTACTCTTCCTTCTTGTC-3' (SEQ ID NO: 24) for p28 Bap31 amino acids 1–246; 5'-GCGGATCCATGAGTC TGCAGTGGACT-3' (SEQ ID NO: 25) and 5'-GCGAATTCAGTCAACAGCAGCTCCCTT-3' (SEQ ID NO: 26) for p28 Bap31 amino acids 1–164; 5'-GCGCGGATCCCCTCATTT CGCAGCAGGCC-3' (SEQ ID NO: 27) and 5'-GCGAATTCAGTCAACAGCAG CTCCCTT-3' (SEQ ID NO: 28) for p28 Bap31 amino acids 122–164; and 5'-GCGGATCCGGAGGCAAGT TGGATGTC-3' (SEQ ID NO: 29) and 5'-GCGAATTCT TACTCTTCCTTCTTGTC-3' (SEQ ID NO: 30) for p28 Bap31 amino acids 165–246.

Fragments generated by PCR were digested with BamH1 and EcoR1, inserted between the BamH1 and EcoR1 sites of pGEX-2T (Pharmacia), and the recombinant plasmids introduced into E. coli MC1061. Packed cells from 500 ml of induced culture were recovered, suspended in 25 ml phosphate buffered saline (PBS) and 0.1% Triton X-100, and sonicated using a Vibra Cell probe sonicator operating at setting 7.5 for 4×15 sec at 4° C. Following centrifugation at 25,000 rpm in a Beckman Ti 50.2 rotor for 25 min, the supernatant was recovered, mixed with 750 μl of a 1:1 suspension of glutathione Sepharose 4B beads, and the mixture rotated at 4° C. for 45 min. Following extensive washing of the beads in PBS and 0.1% Triton X-100, GST fusion protein was eluted with 3 ml of 50 mM Tris HCl, pH 8.0, and 12 mM reduced glutathione.

Antibodies

GST fusion proteins were injected into chickens and the resulting IgY antibodies recovered from eggs, exactly as described in Goping et al., FEBS. 373: 45–50, 1995. After adsorption of IgY that reacted with immobilized GST, antibodies specific for p28 Bap31 sequences were purified by affinity binding to immobilized GST-p28(165–246) or GST-p28(122–164) fusion protein, employing the methods described in the Amino Link Plus kit (Pierce Chemical Co., Rockford, Ill.).

Transient Transfections

CHO LR73 cells were seeded at a density of 5×10$^5$ cells per well in 6-well plates. 24 hours later, cells in each well were transfected by calcium phosphate precipitation with 0.5 μg luciferase reporter plasmid, 10 μg RcRSV-p28 or RcRSV-p20, and 10 μg sheared salmon sperm DNA (Goping et al., Nucl. Acids Res. 23: 1717–1721, 1995). After 24 hours, cells were shocked with 15% glycerol, and collected 24 hours later. Cells from each well were lysed in 0.4 ml 0.5% NP40 and 50 mM Tris HCl, pH 7.8, and aliquots assayed for luciferase activity as previously described (Goping et al., Nucl. Acids Res. 23: 1717–1721, 1995). 293T cells in 10 cm culture plates were similarly transfected with 15 μg total plasmid DNA when cells reached 50–60% confluency.

Co-immunoprecipitations

Approximately 30 hours post-transfection, 293T cells were washed in phosphate buffered saline, and homogenized in 1.0 ml lysis medium per 10 cm culture plate (50 mM Hepes, pH 7.4, 150 mM NaCl, 1 mM ethylenediamine tetraacetate, 0.5% v/v NP40, 10 μg/ml aprotinin, 10 μμg/ml leupeptin, and 1 mM phenylmethylsulfonylfluoride). After centrifugation at 11,000 g, the supernatant was incubated with 50 μl of a 1:1 slurry of protein G Sepharose for 1 hour at 4° C. The Sepharose was removed and the supernatant incubated with mouse M2 anti-Flag antibody (IBI-A Kodak Co., New Haven, Conn.) at 4° C. for 6–8 hours, at which time 20 μl of a 1:1 slurry of protein G Sepharose was added. After 1 hour at 4° C., the beads were recovered, washed, and boiled in SDS sample buffer. Following SDS PAGE and transfer to nitrocellulose, blots were developed with either mouse anti-Myc 9E1D antibody or mouse anti-HA 12CA5 antibody (both from Babco, Berkeley, Calif.) or rabbit anti-Bax sc-526 antibody (commercially available from Santa Cruz Biotech., Inc., Santa Cruz, Calif.).

Expression Plasmids cDNAs encoding proteins tagged with a specific epitopes were constructed in expression vectors. Flag epitope was inserted toward the C-terminus of Bap31, immediately upstream of the KKEE ER retrieval signal; Myc and HA epitopes were placed at the C-termini of Bcl-$X_L$ and proFLICE, respectively.

Synthesis of p28 Bap31

The characteristics of the cloned p28 Bap31 nucleic acid sequences may be analyzed by introducing the sequence into various cell types or using in vitro extracellular systems. The function of p28 Bap31 may then be examined under different physiological conditions. The p28 Bap31 nucleic acid sequence may be manipulated in studies to understand the expression of the gene and gene product. Alternatively, cell lines may be produced which over-express the gene product allowing purification of p28 Bap31 for biochemical characterization, large-scale production, antibody production, and patient therapy.

For protein expression, eukaryotic and prokaryotic expression systems may be employed in which either the p28 Bap31 nucleic acid sequence is introduced into a plasmid or other vector which is then introduced into living cells. An expression plasmid into which the entire open reading frame of either p28 Bap31 cDNA sequence has been inserted in the correct orientation may be used for protein expression. Alternatively, portions of the sequences, including wild-type or mutant p28 Bap31 sequences, may be inserted. Prokaryotic and eukaryotic expression systems allow various important functional domains of the protein to be recovered as fusion proteins and then used for binding, structural and functional studies and also for the generation of appropriate antibodies. Since p28 Bap31 is involved in modulating apoptosis, it may be desirable to control expression levels by use of an inducible promoter (e.g., tet or lac).

Typical expression vectors contain promoters that direct the synthesis of large amounts of mRNA corresponding to the gene. They may also include sequences allowing for their autonomous replication within the host organism, sequences that encode genetic traits that allow cells containing the vectors to be selected, and sequences that increase the efficiency with which the mRNA is translated. Some vectors contain selectable markers such as neomycin resistance that permit isolation of cells by growing them under selective conditions. Stable long-term vectors may be maintained as freely replicating episomal entities by using regulatory elements of viruses. Cell lines may also be produced in which the expression vector has been integrated into the cell's genomic DNA therefore allowing the production of the gene product on a continuous basis.

Expression of foreign sequences in bacteria such as *Escherichia coli* require the insertion of nucleic acid sequences of p28 Bap31 polypeptides into an expression vector, usually a bacterial plasmid. This plasmid vector contains several elements such as an origin of replication, sequences encoding a selectable marker that assures maintenance of the vector in the cell, a controllable transcriptional promoter (i.e., lac) which can produce large amounts of mRNA from the cloned gene upon induction, translational control sequences and a polylinker to simplify insertion of the gene in the correct orientation within the vector. In a simple *E. coli* expression vector utilizing the lac promoter, the expression vector plasmid contains a fragment of the *E. coli* chromosome containing the lac promoter and the neighbouring lacZ gene. In the presence of the lactose analog IPTG, RNA polymerase normally transcribes the lacZ gene producing lacZ mRNA which is translated into the encoded protein, β-galactosidase. The lacZ gene can be cut out of the expression vector with restriction endonucleases and replaced by p28 Bap31 nucleic acid sequences. When this resulting plasmid is transfected into *E. coli*, addition of IPTG and subsequent transcription from the lac promoter produces p28 Bap31 mRNA, which is translated into p28 Bap31.

Once the appropriate expression vectors containing the p28 Bap31 nucleic acid sequences are constructed, they may be introduced into an appropriate host cell by transformation techniques including calcium phosphate transfection, DEAE-dextran transfection, electroporation, microinjection, protoplast fusion, and liposome-mediated transfection. The host cells which are transfected with the vectors of this invention may be selected from the group consisting of *E. coli, pseudomonas, Bacillus subtillus,* or other bacilli, other bacteria, yeast, fungi, insect (using baculoviral vectors for expression), mouse or other animal or human tissue cells. Mammalian cells can also be used to express p28 Bap31 using a vaccinia virus expression system described in the art (see, for example, Ausubel et al., supra).

In vitro expression of proteins encoded by cloned DNA is also possible using the T7 late-promoter expression system. This system depends on the regulated expression of T7 RNA polymerase which is an enzyme encoded in the DNA of bacteriophage T7. The T7 RNA polymerase transcribes DNA beginning within a specific 23-bp promoter sequence called the T7 late promoter. Copies of the T7 late promoter are located at several sites on the T7 genome, but none is present in *E. coli* chromosomal DNA. As a result, in T7 infected cells, T7 RNA polymerase catalyzes transcription of viral genes but not of *E. coli* genes. In this expression system recombinant *E. coli* cells are first engineered to carry the gene encoding T7 RNA polymerase next to the lac promoter. These cells are then transformed with plasmid vectors that carry a copy of the T7 late promoter directing the expression of the p28 Bap31 proteins. When IPTG is added to the culture medium containing these transformed *E. coli* cells, large amounts of T7 RNA polymerase are produced. The polymerase then binds to the T7 late promoter on the plasmid expression vectors, catalyzing transcription of the inserted p28 Bap31 cDNAs at a high rate. Since each *E. coli* cell contains many copies of the expression vector, large amounts of mRNA corresponding to the cloned cDNA can be produced in this system and the resulting p28 Bap31 polypeptides can be radioactively labelled. Plasmid vectors containing late promoters and the corresponding RNA polymerases from related bacteriophages such as T3, T5, and SP6 may also be used for in vitro production of p28 Bap31 polypeptides from cloned DNA. *E. coli* can also be used for expression by infection with M13 Phage mGPI-2. *E. coli* vectors can also be used with phage lambda regulatory sequences, by fusion protein vectors, by maltose-binding protein fusions, and by glutathione-S-transferase fusion proteins.

Eukaryotic expression systems permit appropriate post-translational modifications to expressed proteins. This allows for studies of the p28 Bap31 gene and gene product, including determination of proper expression and post-translational modifications for biological activity, identifying regulatory elements located in the 5' region of the genes and analyzing their roles in tissue regulation of gene product expression. It also permits the production of large amounts of normal and mutant proteins for isolation and purification. Cells expressing p28 Bap31 may be used in a functional assay system for antibodies generated against the protein and are important vehicles in which to test the effectiveness of pharmacological agents modulating p28 Bap31, to assess the role of p28 Bap31 as a component of a signal transduction system, and to study the in vivo function of the normal complete protein, specific portions of the protein, or naturally occurring polymorphisms and artificially produced mutated polypeptides. The nucleic acid sequences encoding p28 Bap31 can be altered using procedures such as restriction endonuclease digestion, DNA polymerase fill-in, exonuclease deletion, terminal deoxynucleotide transferase extension, ligation of synthetic or cloned DNA sequences and site-directed sequence alteration using specific oligonucleotides together with PCR.

A p28 Bap31 may be produced by a stably-transfected mammalian cell line. A number of vectors suitable for stable transfection of mammalian cells are available to the public (e.g., see Pouwels et al., *Cloning Vectors: A Laboratory Manual*, 1985, Supp. 1987), as are methods for constructing such cell lines (see e.g., Ausubel et al., supra). In one example, cDNA encoding the desired protein (i.e., p28 Bap31) is cloned into an expression vector that includes the dihydrofolate reductase (DHFR) gene. Integration of the expression plasmid bearing the protein-encoding nucleic acid into the host cell chromosome is selected for by inclusion of 0.01–300 $\mu$M methotrexate in the cell culture medium (as described in, e.g., Ausubel et al., supra). This dominant selection can be accomplished in most cell types.

Recombinant protein expression can be increased by DHFR-mediated amplification of the transfected nucleic acid (e.g., nucleic acid encoding p28 Bap31). Methods for selecting cell lines bearing gene amplifications are described in Ausubel et al. (supra) and generally involve extended culture in medium containing gradually increasing levels of methotrexate. The most commonly used DHFR-containing expression vectors are pCVSEII-DHFR and pAdD26SV(A) (described in Ausubel et al., supra). The host cells described above or, preferably, a DHFR-deficient CHO cell line (e.g., CHO DHFR-cells, ATCC Accession No. CRL 9096) are among those most preferred for DHFR selection of a stably-transfected cell line or DHFR-mediated gene amplification.

Another preferred expression system is the baculovirus system using, for example, the vector pBacPAK9, which is available from Clontech (Palo Alto, Calif.). If desired, this system may be used in conjunction with other protein expression techniques, for example, the myc tag approach described by Evan et al. (Mol. Cell. Biol. 5: 3610–3616, 1985).

Once the recombinant protein is expressed, it is isolated by, for example, affinity chromatography. In one example, an anti-p28 Bap31 antibody, which may be produced by the methods described herein, can be attached to a column and used to isolate the p28 Bap31 polypeptide. Lysis and fractionation of p28 Bap31-expressing cells prior to affinity chromatography may be performed by standard methods (see e.g., Ausubel et al., supra). Once isolated, the recombinant protein may, if desired, be further purified by e.g., by high performance liquid chromatography (HPLC; e.g., see Fisher, *Laboratory Techniques In Biochemistry And Molecular Biology*, Work and Burdon, eds., Elsevier, 1980).

Polypeptides of the invention, particularly short p28 Bap31 fragments, can also be produced by chemical synthesis (e.g., by the methods described in *Solid Phase Peptide Synthesis*, 2nd ed., 1984 The Pierce Chemical Co., Rockford, Ill.). These general techniques of protein expression and purification can also be used to produce and isolate useful p28 Bap31 fragments or analogs, as described herein.

Those skilled in the art of molecular biology will understand that a wide variety of expression systems employing a wide variety of host cells may be used to produce the recombinant protein. The p28 Bap31 polypeptides may be produced in a prokaryotic host (e.g., *E. coli*) or in a eukaryotic host (e.g., *S. cerevisiae*, insect cells such as Sf9 cells, or mammalian cells such as COS-1, NIH 3T3, or HeLa cells). These cells are publically available, for example, from the American Type Culture Collection, Rockville, Md.; see also Ausubel et al., supra). The method of transduction and the choice of expression vehicle will depend on the host system selected. Transformation and transfection methods are described, e.g., in Ausubel et al. (supra), and expression vehicles may be chosen from those provided, e.g., in Pouwels et al., supra.

Testing for the Presence of p28 Bap31 Biological Activity

The identified Bcl-2-interacting protein, p28 Bap31, has been shown to be linked to apoptotic cell death in two ways. First, p28 Bap 31 is cleaved at the two ICE/FLICE recognition sequences following induction of apoptosis. Both cleavages are observed in intact cells and their appearance closely correlates with pro-enzyme activation of Caspase-3 (CPP 32) and cell death following infection of KB cells with adenovirus type 5 lacking expression of E1B 19K. Secondly, ectopic expression of the p20 cleavage product of p28 induces apoptosis. Without being limited to a particular model, the p20 cleavage product may induce apoptosis by a trans-dominant mechanism that interferes with normal p28 Bap31 function.

Identification of p28 Bap31 allows the study of p28 Bap31 co-association with a Bcl-2 protein (e.g., Bcl-$X_L$ and Bcl-2) and/or pro-FLICE, an ability to be cleaved to produce the p20 product, and involvement in apoptosis-associated cellular events. These p28 Bap31 biological activities may also be evaluated based upon the level of expression of p28 Bap31. For example, interaction of p28 Bap31 with pro-FLICE and a Bcl-2 protein may be measured by utilizing the various methods known in the art and described herein for measuring protein:protein interactions (e.g., the yeast two-hybrid interaction system assay). Furthermore, administration of a p28 Bap31 protein or polypeptide fragment thereof, or a p28 Bap31-inhibiting compound may be used to modulate apoptosis, as may be measured by apoptosis assays known in the art and described herein. Preferably, such assays are carried out in a cell capable of undergoing apoptosis (e.g., human KB cells).

Another method for assessing the biological activity of p28 Bap31 by measuring the level of expression of p28 Bap31 may be accomplished by measuring the amount of protein expression using p28 Bap31-specific antibodies (e.g., the antibodies described above), or by measuring the amount of p28 Bap31 mRNA, using detectably labelled p28 Bap31 nucleic acid as a probe. In addition, the proteolytic cleavage of p28 Bap31 into the p20 product may be detected using the assays described above (see, e.g., FIGS. 5A and 5B). These assays may also be used to assess the ability of a reagent or compound to inhibit or enhance the biological activity of the p28 Bap31 protein (which is, in this particular example, an ability to be cleaved to produce the p20 product), and thus modulate apoptosis.

P28 Bap31 Fragments

Polypeptide fragments comprising various portions of p28 Bap31 are useful in identifying regions of these proteins important for their biological activities (e.g., their abilities to modulate apoptosis). Methods for generating such fragments are well known in the art (see, for example, Ausubel et al., supra) using the nucleotide sequences encoding the full length p28 Bap31 polypeptides. For example, a p28 Bap31 fragment may be generated by PCR amplifying the desired fragment using oligonucleotide primers designed based upon the p28 Bap31 nucleic acid sequence. Preferably the oligonucleotide primers comprise unique restriction enzyme sites which facilitate insertion of the fragment into the cloning site of an expression vector. This vector may then be introduced into a cell by artifice by the various techniques known in the art and described herein, resulting in the production of p28 Bap31 polypeptide fragment.

In an alternative approach, polypeptide fragments comprising various portions of p28 Bap31 are useful in modulating p28 Bap31 mediated apoptosis, respectively, as may be assessed in the various apoptosis assays known in the art and described herein. P28 Bap31 polypeptide fragments (e.g., a fragment corresponding to the p20 product) may be used to induce apoptosis in a cell.

P28 Bap31-specific Antibodies

In order to prepare polyclonal antibodies, p28 Bap31 polypeptides, fragments thereof, or fusion proteins containing defined portions or the entire p28 Bap31 polypeptide can be synthesized in bacteria by expression of corresponding DNA sequences in a suitable cloning vehicle. A common source of antigen for producing antibodies are fusion proteins. Two widely used expression systems for *E. coli* are lacZ fusions using the pUR series of vectors and trpE fusions using the pATH vectors. The proteins may be purified, and then may be coupled to a carrier protein, mixed with Freund's adjuvant (to help stimulate the antigenic response by the animal), and injected into laboratory animals of choice (e.g., rabbits). Alternatively, p28 Bap31 proteins can be isolated from expressing cultured cells. Following booster injections at bi-weekly intervals, the immunized rabbits are bled and the sera isolated. The sera may be used directly or may be purified prior to use by various methods including affinity chromatography employing reagents such as Protein A-Sepharose, Antigen Sepharose, and Anti-rabbit-Ig-Sepharose. The sera may be used to probe tissue extracted proteins which have been resolved on a polyacrylamide gel to identify the p28 Bap31 polypeptides. Alternatively, synthetic peptides can be made that correspond to the antigenic portions of the protein and used to immunize the animals.

In order to generate polypeptide fragments or fill-length protein for use in making p28 Bap31-specific antibodies, the coding sequences can be expressed as a C-terminal fusion with glutathione S-transferase (GST; Smith et al., Gene 67: 31–40, 1988). The GST fusion proteins can be purified on glutathione-Sepharose beads, eluted with glutathione, and cleaved with thrombin (at the engineered cleavage site), and purified to the degree required to successfully immunize rabbits. Primary immunizations can be carried out with Freund's complete adjuvant and subsequent immunizations performed with Freund's incomplete adjuvant. Antibody titers are monitored by Western blot and immunoprecipitation analyses using the thrombin-cleaved p28 Bap31 fragment of the GST fusion protein. Immune sera are affinity purified using p28 Bap31 proteins coupled to CNBr-Sepharose. Antiserum specificity is determined using an unrelated GST protein which may be generated by PCR using known sequences.

The skilled artisan will understand that p28 Bap31-specific murine monoclonal antibodies may be prepared using the p28 Bap31 proteins described above and standard hybridoma technology (see, e.g., Kohler et al., Nature 256: 495–497, 1975; Kohler et al., Eur. J. Immunol. 6: 511–519, 1976; Kohler et al., Eur. J. Immunol. 6: 292–295, 1976; Hammerling et al., In *Monoclonal Antibodies and T Cell Hybridomas,* Elsevier, New York, N.Y., 1981; Ausubel et al., supra). To produce p28 Bap31-specific murine monoclonal antibodies, for example, mice may be immunized with recombinant p28 Bap31 proteins and fusion proteins described above, as well as p28 Bap31 isolated from cells which normally express p28 Bap31 or p28 Bap31 isolated from tissues. Cellular extracts or recombinant protein extracts containing the p28 Bap31, may, for example, be injected with Freund's adjuvant into mice. Following primary injection and subsequent boosters, serum samples may be collected and assessed for an ability to bind p28 Bap31. Spleens from mice whose sera are p28 Bap31 reactive are removed and minced to attain a suspension of isolated spleen cells. The spleen cells serve as a source of B lymphocytes, some of which are producing antibody of the appropriate specificity. The spleen cells are fused with a permanently growing myeloma partner cells, and the products of the fusion are plated into 96 well plates in culture media containing a selective agent such as hypoxanthine, aminopterine, and thymidine (HAT). The wells are then screened by ELISA to identify those containing cells producing antibody capable of binding p28 Bap31 protein or polypeptide fragments or mutants thereof. The cells producing p28 Bap31-reactive antibodies are returned to the selective culture media and cloned by limiting dilution into 96 well plates. After a period of growth, wells are again screened to identify p28 Bap31 specific antibody-producing cells. Several cloning procedures are carried out until over 90% of the wells contain single clones which are positive for p28 Bap31 specific antibody production. From this procedure a stable line of hybridoma clones is established, each of which produces a monoclonal antibody capable of specifically binding to the p28 Bap31. Ascites containing large amounts of p28 Bap31 specific monoclonal antibody can be generated by injecting the p28 Bap31 specific monoclonal antibody secreting hybridoma cells into a mouse having the same MHC haplotype as the mouse whose spleen cells were used to make the hybridoma cell clone.

The p28 Bap31-reactive monoclonal antibodies can be further purified by affinity chromatography using Protein A Sepharose, ion-exchange chromatography, as well as variations and combinations of these techniques. Truncated versions of monoclonal antibodies may also be produced by recombinant methods in which plasmids are generated which express the desired monoclonal antibody fragment(s) in a suitable host.

As an alternate or adjunct immunogen to GST fusion proteins, peptides corresponding to relatively unique hydrophilic regions of p28 Bap31 may be generated and coupled to keyhole limpet hemocyanin (KLH) through an introduced C-terminal lysine. Antiserum to each of these peptides is similarly affinity purified on peptides conjugated to CNBr-Sepharose, and specificity may be tested by ELISA and Western blotting using peptide conjugates, and by Western blotting and immunoprecipitation using p28 Bap31 expressed as GST fusion proteins. Methods describing these analysis techniques are well known in the art (see, for example, Ausubel et al., supra; Hammerling et al., supra; and Sambrook, et al., *Molecular Cloning: A Laboratory Manual* (2d ed.), CSH Press, 1989).

Antibodies that specifically recognize p28 Bap31, or fragments thereof are considered useful in the invention. They may, for example, be used in an immunoassay to monitor p28 Bap31 protein expression levels or to determine the subcellular location of the polypeptides or fragments produced by a mammal. P28 Bap31 fragments may also be used to inhibit binding of the p28 Bap31 to a Bcl-2 protein and/or to pro-FLICE. Antibodies that inhibit p28 Bap31 interactions described herein may be especially useful in preventing apoptosis in cells undergoing undesirable cell death.

Preferably, antibodies of the invention are produced using p28 Bap31 protein amino acid sequences that do not reside within highly conserved regions, and that appear likely to be antigenic, as analyzed by criteria such as those provided by the Peptide Structure Program (Genetics Computer Group Sequence Analysis Package, Program Manual for the GCG Package, Version 7, 1991) using the algorithm of Jameson and Wolf (CABIOS 4: 181, 1988). These fragments can be generated by standard techniques, e.g., by the PCR, and cloned into the pGEX expression vector (Ausubel et al., supra). GST fusion proteins are expressed in E. coli and purified using a glutathione agarose affinity matrix as described in Ausubel et al. (supra). To generate rabbit polyclonal antibodies, and to minimize the potential for obtaining antisera that is non-specific, or exhibits low-affinity binding to p28 Bap31, two or three fusions are generated for each protein, and each fusion is injected into at least two rabbits. Antisera are raised by injections in series, preferably including at least three booster injections.

In addition to intact monoclonal and polyclonal p28 Bap31-specific antibodies, the invention features various genetically engineered antibodies, humanized antibodies, and antibody fragments, including F(ab')2, Fab', Fab, Fv, and sFv fragments. Methods for making humanized antibodies are known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also features of the invention (Green et al., Nature Genetics 7: 13–21, 1994).

In addition, Ladner (U.S. Pat. Nos. 4,946,778 and 4,704,692) describes methods for preparing single polypeptide chain antibodies. Ward et al. (Nature 341: 544–546, 1989) describe the preparation of heavy chain variable domains, which they term "single domain antibodies," which have high antigen-binding affinities. McCafferty et al. (Nature 348: 552–554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describe various methods for producing immunoglobulins, and immunologically functional fragments thereof, which include at least the variable domains of the heavy and light chain in a single host cell. Cabilly et al. (U.S. Pat. No. 4,816,567) describe methods for preparing chimeric antibodies. These p28 Bap31-specific reagents are also features of the instant invention.

Use of p28 Bap31-specific Antibodies

Antibodies that specifically bind to p38 Bap31 or fragments thereof may be used, as noted above, to detect protein expression and modulate the biological activity of the protein. In addition, the antibodies may be coupled to compounds for diagnostic and/or therapeutic uses such as radionucleotides for imaging and therapy and liposomes for the targeting of compounds to a specific tissue location.

Detection of p28 Bap31 Gene Expression

As noted, the antibodies described above may be used to monitor p28 Bap31 expression in cells or tissues using Western blot or immunoprecipitation analysis (according to methods described herein and in the art.

Another method which may be used to detect the expression of p28 Bap31 genes is in situ hybridization, which relies upon the hybridization of a specifically labelled nucleic acid probe to the cellular RNA in individual cells or tissues. Therefore, it allows the identification of mRNA within intact tissues, such as the brain. In this method, oligonucleotides or cloned nucleic acid (RNA or DNA) fragments corresponding to unique portions of the desired gene (e.g., p28 Bap31) are used to detect specific mRNA species, e.g., in a neuron.

Identification of Compounds that Modulate p28 Bap31

Molecules that are found, by the methods described herein, to effectively modulate p28 Bap31 gene expression or biological activity may be tested further in animal models. If they continue to function successfully in an in vivo setting, they may be used as therapeutics to either inhibit or enhance apoptosis, as appropriate.

A) Compounds that Modulate p28 Bap31 Biological Activity

P28 Bap31-encoding cDNAs may be used to facilitate the identification of compounds that increase or decrease expression of these proteins. In one approach for detecting a compound that modulates p28 Bap31 expression, candidate compounds are added, in varying concentrations, to the culture medium of cells expressing p28 Bap31 mRNA. P28 Bap31 expression is then measured, for example, by Northern blot analysis (Ausubel et al., supra) using a p28 Bap31 DNA, or cDNA or RNA fragment, as a hybridization probe. The level of p28 Bap31 expression in the presence of the candidate compound is compared to the p28 Bap31 expression level in the absence of the candidate compound, all other factors (e.g., cell type and culture conditions) being equal.

The effect of candidate compounds on p28 Bap31 expression may, instead, be measured at the level of translation by using the general approach described above with standard protein detection techniques, such as Western blotting or immunoprecipitation with p28 Bap31-specific antibodies (for example, the antibodies described herein).

In an alternative approach to detecting compounds which modulate p28 Bap31 at the level of transcription, candidate compounds may be tested for an ability to regulate a reporter gene whose expression is directed by the p28 Bap31 promoter. For example, to detect a compound that can modulate p28 Bap31 expression, candidate compounds may then be added, in varying concentrations, to the culture medium of cells transfected with a expression plasmid comprising a luciferase reporter gene operably linked to the p28 Bap31 promoter. Luciferase expression levels may then be measured on a luminometer by subjecting the compound-treated transfected cells to standard luciferase assays known in the art, such as the luciferase assay system kit commercially available from Promega (Madison, Wis.). Luciferase expression in the presence of the candidate compound is compared to the level of luciferase expression in the absence of the candidate compound, all other factors (e.g., cell type and culture conditions) being equal.

Compounds that modulate the level of p28 Bap31 expression may be purified, or substantially purified, or may be one component of a mixture of compounds such as an extract or supernatant obtained from cells (Ausubel et al., supra). In an assay of a mixture of compounds, p28 Bap31 expression is tested against progressively smaller subsets of the compound pool (e.g., produced by standard purification techniques such as HPLC or FPLC) until a single compound or minimal number of effective compounds is demonstrated to modulate p28 Bap31 expression levels.

Compounds may also be screened for an ability to modulate other biological activities of p28 Bap31. In this approach, the degree of p28 Bap31 biological activity in the presence of a candidate compound is compared to the degree of p28 Bap31 biological activity in its absence, under equivalent conditions. The biological activity of p28 Bap31 may be assayed by its role in apoptosis. The biological activity of p28 Bap31 may additionally be assayed by its ability to be cleaved into the p20 product. Again, the screen may begin with a pool of candidate compounds, from which one or more useful p28 Bap31 biological activity-modulating compounds is isolated in a step-wise fashion.

A compound that induces an increase in expression and/or biological activity of p28 Bap31 or the p20 Bap31 product is considered particularly useful in the invention; such a compound may be used, for example, as a therapeutic to increase cellular levels of p28 Bap31 or the p20 Bap31 product and/or the biological activities of these proteins, and thereby exploit their abilities to promote apoptosis in a cell (e.g., a cancer cell) which has a reduced level of apoptosis.

A compound that inhibits the levels of p28 Bap31 or the p20 Bap31 product and/or biological activities of these proteins may be used to increase cellular proliferation in cells which show an undesirably high level of apoptosis. This would be advantageous in the treatment of degenerative diseases, such as neurodegenerative diseases (e.g., Alzheimer's disease, Huntington's disease) or other tissue-specific degenerative diseases (e.g., cirrhosis of the liver, T-lymphocyte depletion in AIDS).

One method for detecting compounds that modulate the biological activity of p28 Bap31 is to screen for compounds that alter the physical interaction of p28 Bap31 with either a Bcl-2 protein (e.g., Bcl-2 or Bcl-$X_L$) or pro-FLICE. These compounds are detected by adapting yeast two-hybrid expression systems known in the art. Yeast two-hybrid systems detect protein interactions using a transcriptional activation assay and are generally described by Gyuris et al. (Cell 75: 791–803, 1993) and Field et al. (Nature 340: 245–246, 1989). Reagents for yeast two-hybrid systems are also are commercially available from Clontech (Palo Alto, Calif.). Once an interaction between p28 Bap31 and either a Bcl-2 protein or pro-FLICE is detectable in yeast, compounds may be screened for an ability to alter that interaction.

In one example, if the Clontech Matchmaker Two-Hybrid System (Catalog number K1605-1) is used, p28 Bap31, Bcl-2, or Bcl-$X_L$ polypeptides fused to either the GAL4 DNA binding domain or activator domain can be made by cloning the nucleic acid sequences encoding full length polypeptides or fragments thereof into the appropriate vectors available in the kit. A vector, for example, a DNA binding domain vector, encoding a p28 Bap31 protein (or fragment thereof) fusion is then co-transformed with a vector, for example an activation domain vector, encoding a Bcl-2 protein (or fragment thereof) fusion into the yeast strains included in the kit. Polypeptides of p28 Bap31 which form strong interactions with a Bcl-2 polypeptide will result in blue colonies on X-gal containing media. A candidate compound or combinations thereof which are being screened for an ability to alter interactions between p28 Bap31 and a Bcl-2 protein can be administered to the yeast which form blue colonies on X-gal plates. A compound which can alter the color of the colony on X-gal plates as compared to an untreated colony is a compound that alters the interaction between p28 Bap31 and the protein (Bcl-2) which ws co-expressed as an activation fusion protein in the compound administered blue yeast colony.

By disrupting the association of p28 Bap31 to either a Bcl-2 protein or pro-FLICE, such a compound may function as modulator of p28 Bap31-associated apoptotic cell death and may include peptide and non-peptide molecules such as those present in cell extracts, mammalian serum, or growth medium in which mammalian cells have been cultured. The effect of interaction-disrupting compounds on p28 Bap31 apoptosis activity may be measured by any standard assay, for example, those described herein.

Another method for detecting compounds that modulate the biological activity of p28 Bap31 is to screen for compounds that affect the in vitro association of p28 Bap31 with Bcl-2. Compounds may be assessed for an ability to affect the binding of p28 Bap31 to Bcl-2 by adding a candidate compound to p28 Bap31 protein immunoprecipitates from cells co-transfected with p28 Bap31 and Bcl-2 protein-encoding nucleic acids. Following Western blotting analysis with an anti-Bcl-2 antibody (such as clones 100 or 4C11 commercially available from Santa Cruz Biotech., Inc., Santa Cruz, Calif.), whether or not a compound affects the binding of p28 Bap31 to Bcl-2 may be assessed by comparing the amount of anti-Bcl-2 immunoreactive protein in a compound-treated reaction versus an untreated reaction. The amount of Bcl-2 may be assessed, for example, by quantitation on a Phorphorimager.

In a method to detect a compound that affects the cleavage of p28 Bap31 to p20, a candidate compound may be added to the $^{35}$S-labelled transcription-translation product of p28 cDNA, which is then incubated with increasing concentrations of ICE (caspase-1). Following resolution by SDS-PAGE, the products can compared to a reaction carried out in absence of the candidate compound (control). A compound that affects the cleavage of p28 Bap31 as compared to the control reaction is a compound that modulates the biological activity of p28 Bap31.

By either affecting the association of p28 Bap31 with a Bcl-2 protein or with pro-FLICE, or by affecting the cleavage of p28 Bap31 to p20, a compound may function as modulator of p28 Bap31-associated apoptotic cell death. Such a compound may include peptide and non-peptide molecules such as those present in cell extracts, mammalian serum, or growth medium in which mammalian cells have been cultured.

B) Compounds that Modulate p20 Biological Activity

A compound that affects p20 biological activity may be assessed by treating cells with a candidate compound prior to intracellular expression of p20. Apoptosis may be assessed by a variety of assays described herein including, without limitation, DNA fragmentation, membrane blebbing, and Annexin V reactivity at the cell surface. A compound found to either enhance or inhibit the ability of p20 to induce apoptosis in a p20 expressing cell relative to a p20 expressing cell untreated with the compound is a compound that modulates p20 biological activity. Such a compound is useful to either induce cell death in hyperplasia cells (e.g., cancerous cell), or inhibit cell death in cells that undergo inappropriately high levels of apoptosis (e.g., T cells in HIV infected individuals).

High through-put screens may be employed to identify the protease responsible for the cleavage of p28 Bap31 into p20. Since p20 expression will cause apoptosis, a compound that produces p20 may be readily identified using the various apoptosis assays known in the art and described herein. For example, a cell may be stably transfected with a high expressing plasmid encoding for p28 Bap31. The stable p28 Bap31 cells may then be transiently transfected in groups with pools of plasmids from a cDNA expression library, and the groups of cells examined for apoptosis. Once a group of cells is identified as undergoing apoptosis at a frequency higher than is normally observed in p28 Bap31 stably expressing cells, the plasmid DNA used to transfect the cells is sub-divided and each division transfected into groups of p28 Bap31 stably expressing cells. Following repetition of this transfect/subdivision, an cDNA encoding a protein capable of cleaving p28 Bap31 to produce p20 may be isolated and subjected to DNA sequence analysis. Once identified, the protein (i.e., a protease) capable of cleaving p28 Bap31 to produce p20 may be subjected to the manipulations described herein for p28 Bap31.

Genes Related to p28 Bap31

Standard techniques, such as the polymerase chain reaction (PCR) and DNA hybridization, may be used to clone additional p28 Bap31 homologues in other species. For example, Southern blot analysis may be made of genomic DNA of various organisms (e.g., C. elegans or mice) with nucleic acid probes generated from the nucleic acid sequences encoding p28 Bap31. Hybridization at low stringency may reveal bands that correspond to p28 Bap31, and/or related family members. P28 Bap31 probes may be based on the codon preference displayed by the organism, or may be degenerate probes based upon all possible codon combinations, or a combination of codon preference and codon degeneracy. This probe may then be used to screen either genomic or cDNA libraries for sequences which hybridize to the probe. Thus, additional p28 Bap31 may be identified using low stringency hybridization. Furthermore, p28 Bap31 probes may be used as primers to clone additional p28 Bap31 related genes by RT-PCR.

Therapies

Therapies may be designed to prevent or treat a p28 Bap31 gene defect or an inadequate or excessive amount of p28 Bap31 gene expression, and thus modulate apoptosis. In considering various therapies, it is understood that such therapies may be targeted at any tissues demonstrated to express the p28 Bap31 protein. In particular, therapies to enhance p28 Bap31 gene expression are useful in promoting apoptosis in neoplastic cells. Apoptosis-inducing p28 Bap31 reagents may include, without limitation, full length or fragment p28 Bap31 polypeptides, p28 Bap31 mRNA, or any compound which increases p28 Bap31 expression and apoptosis-inducing activity.

a) Protein Therapy

Treatment or prevention of an inappropriate amount of apoptosis may be accomplished by correcting dysfunction caused by mutant, deficient, or surplus p28 Bap31 protein with normal protein, by modulating the function of mutant protein, or by delivering normal p28 Bap31 proteins to the appropriate cells. The pathophysiological pathway (e.g., the apoptosis signalling pathway) in which the protein participates may also be modified in order to correct the physiological defect.

To administer p28 Bap31 proteins to cells which either no longer express sufficient amounts of either of these proteins, or produce mutant dysfunctional protein, it is necessary to obtain large amounts of pure p28 Bap31 from cultured cell systems which can express the proteins. Delivery of the proteins to the affected tissues and/or cells (e.g., cancerous cells) can then be accomplished using appropriate packaging or administrating systems. Alternatively, compounds which act as p28 Bap31 agonists may be administered to the affected cells and/or tissues and in this manner produce the desired physiological effect. Methods for finding such compounds are provided herein.

b) Gene Therapy

Gene therapy is another potential therapeutic approach for treating cells which lack a normal level of expression of a functional p28 Bap31. In one approach, copies of the functional p28 Bap31 gene are introduced into selected tissues to encode for the normal level of expression of the functional protein in affected cell types (e.g., cancer cells which show reduced levels of apoptosis or degenerative cells which show an increased level of apoptosis). The gene must be delivered to those cells in a form in which it can be taken up and encode for sufficient protein to provide effective function.

Transducing retroviral vectors are particularly useful for somatic cell gene therapy because of their high efficiency of infection and stable integration and expression. The targeted cells, however, must be able to divide and require high levels of normal protein expression. For example, to treat a deficiency involving p28 Bap31, the full length p28 Bap31 gene, or portions thereof, may be cloned into a retroviral vector with its expression directed by its endogenous promoter or by the retroviral long terminal repeat or by a promoter specific for the target cell type of interest (such as a neuron). Other viral vectors which can be used include adeno-associated virus, vaccinia virus, bovine papilloma virus, or a herpes virus.

Gene transfer could also be achieved using non-viral means requiring in vitro transfection of affected cells with p28 Bap31 genes or fragments thereof. This in vitro transfection methods include calcium phosphate, DEAE dextran, electroporation, and protoplast fusion. Liposomes may also be potentially beneficial for delivery of DNA into a cell. Although these and other methods known in the art are available, many of these are of low transfection efficiency.

Strategies based upon antisense RNA may be employed to explore p28 Bap31 gene function and as a basis for therapeutic drug design. Antisense RNA based strategies are particularly useful in controlling p28 Bap31 overexpression in cells or tissues undergoing an increased level of apoptosis (e.g., neurons in a patient with a neurodegenerative disorder). The principle is based upon the hypothesis that sequence-specific suppression of gene expression can be achieved by intracellular hybridization between mRNA and a complementary antisense species. The formation of a hybrid RNA duplex may then interfere with the processing, transport, translation, and/or stability of the target p28 Bap31 mRNA. Antisense strategies may use a variety of approaches including, without limitation, the use of antisense oligonucleotides and injection of antisense p28 Bap31 RNA to a cell or tissue that is expected to undergo undesired apoptosis. The antisense p28 Bap31 RNA may be produced and isolated by any standard technique, but is most readily produced by in vitro transcription using an antisense cDNA under the control of a high efficiency promoter (e.g., the T7 promoter). Administration of antisense p28 Bap31 RNA to cells can be carried out by any of the methods for direct nucleic acid administration described above.

Introduction of normal p28 Bap31 genes into the affected cells of a patient may also be useful therapy. In this procedure, normal p28 Bap31-encoding nucleic acid is transfected into a cultivatable cell type, which may or may not be derived from the patient, such that the nucleic acid is either incorporated into the chromosome, or exists and replicates episomally. Preferably, the cell has the same MHC haplotype as the affected patient. The transfected cells are then injected serotologically into the targeted tissue(s) of the patient.

Retroviral, adenoviral, adenovirus-associated viral vectors, or other viral vectors with the appropriate tropism for cells likely to be involved in apoptosis (for example, lymphocytes) may be used as gene transfer delivery systems for a therapeutic p28 Bap31 gene construct. Numerous vectors useful for this purpose are generally known (Miller, A. D., Human Gene Ther. 1: 5–14, 1990; Friedmann T., Science 244: 1275–1281, 1989; Eglitis and Anderson, BioTechniques 6: 608–614, 1988; Tolstoshev and Anderson, Curr. Opin. in Biotech. 1: 55–61, 1990; Cornetta et al., Prog. Nucleic Acid Res. Mol. Biol. 36: 311–322, 1989; Anderson, W. F., Science 226: 401–409, 1984; Moen, R. C., Blood Cells 17: 407–416, 1991; Miller et al., BioTechniques 7: 980–990, 1989; Le Gal La Salle et al., Science 259: 988–990, 1993; and Johnson, L. G., Chest 107: 77S–83S, 1995). Retroviral vectors are particularly well developed and have been used in clinical settings (Rosenberg et al., N.

Engl. J. Med 323: 570–578, 1990; Anderson et al., U.S. Pat. No. 5,399,346). Non-viral approaches may also be employed for the introduction of therapeutic DNA into cells otherwise predicted to undergo apoptosis. For example, p28 Bap31 proteins may be introduced into a neuron or a T cell by lipofection (Felgner et al., Proc. Natl. Acad. Sci. USA 84: 7413–7417, 1987; Ono et al., Neurosci. Lett. 117: 259–263, 1990; Brigham et al., Am. J. Med. Sci. 298: 278–281, 1989; Straubinger et al., Methods Enzymol. 101: 512–527, 1983), asialorosonucoid-polylysine conjugation (Wu et al., J. Biol. Chem. 263: 14621–14624, 1988; Wu et al., J. Biol. Chem. 264: 16985–16987, 1989); or, less preferably, micro-injection under surgical conditions (Wolff et al., Science 247: 1465–1468, 1990).

For any of the methods of application described above, the therapeutic p28 Bap31 DNA construct is preferably applied (for example, by injection) to the site of cells or tissues affected by either abnormally high or low levels of apoptosis. However, it may also be applied to tissue in the vicinity of the affected site or to a blood vessel supplying the cells (e.g., cancerous cells) at the affected site.

In the constructs described, p28 Bap31 gene expression can be directed by any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in neural cells, lymphocytes, or muscle cells may be used to direct p28 Bap31 gene expression. Alternatively, if a p28 Bap31 genomic clone is used as a therapeutic construct, regulation may be mediated by the cognate regulatory sequences or, if desired, by regulatory sequences derived from a heterologous source, including any of the promoters or regulatory elements described above.

Ideally, the amount of p28 Bap31 protein produced by any gene therapy approach will result in cellular levels of protein that are at least equivalent to the normal cellular level of protein in an unaffected cell. Treatment by any p28 Bap31-mediated gene therapy approach may be combined with more traditional therapies.

Another therapeutic approach within the invention involves administration of recombinant p28 Bap31 protein, either directly to the site of a cells or tissues affected by increased or decreased levels of apoptosis (for example, by injection) or systemically (for example, by any conventional recombinant protein administration technique). The dosage of p28 Bap31 depends on a number of factors, including the size and health of the individual patient.

Administration of p28 Bap31 Polypeptides, Genes, or Modulators of p28 Bap31 Synthesis or Function A p28 Bap31 protein, gene, or modulator may be administered within a pharmaceutically-acceptable diluent, carrier, or excipient, in unit dosage form. Conventional pharmaceutical practice may be employed to provide suitable formulations or compositions to administer neutralizing p28 Bap31 antibodies or p28 Bap31-inhibiting compounds (e.g., a compound that prevents the cleavage of p28 Bap31 to p20) to patients suffering from a disease (e.g., a degenerative disease) that is caused by excessive apoptosis. Likewise, formulations or compositions may be provided to administer compounds which increase p28 Bap31 expression (e.g., a compound that induces p28 Bap31 expression and/or activity or recombinant p28 Bap31 protein) to patients suffering from a disease (e.g., cancer) that is caused by a reduced level of apoptosis. Such administration may be limited to the affected tissue or cell. Administration may also begin before the patient is symptomatic. Any appropriate route of administration may be employed, for example, administration may be parenteral, intravenous, intra-arterial, subcutaneous, intramuscular, intracranial, intraorbital, ophthalmic, intraventricular, intracapsular, intraspinal, intrathecal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods for making formulations are well known in the art and may be found, for example, in *Remington's Pharmaceutical Sciences,* (18$^{th}$ edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for p28 Bap31 modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a p28 Bap31 polypeptide or gene, or a p28 Bap31 modulatory compound may be combined with more traditional therapies for the disease such as surgery, chemotherapy, or radiation therapy for cancer, and antiviral therapy for AIDS.

Detection of Conditions Involving Altered Apoptosis

P28 Bap31 polypeptides and nucleic acid sequences may be used diagnostically to detect or monitor conditions involving aberrant levels of apoptosis. For example, a decreased expression of p28 Bap31 is found to be correlated with decreased apoptosis in humans. Similarly, overexpression of p28 Bap31 is found to be associated with increased apoptosis. Accordingly, a decrease or increase in the level of p28 Bap31 production or expression may provide an indication of a deleterious condition. Levels of p28 Bap31 expression may be assayed by any standard technique. For example, p28 Bap31 expression in a biological sample (e.g., a biopsy) may be monitored by standard Northern blot analysis or may be aided by PCR (see, e.g., Ausubel et al., supra; *PCR Technology: Principles and Applications for DNA Amplification,* H. A. Ehrlich, Ed. Stockton Press, NY; Yap et al., Nucl. Acids Res. 19: 4294, 1991).

Alternatively, a biological sample obtained from a patient may be analyzed for one or more mutations in the p28 Bap31 nucleic acid sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant p28 Bap31 detection, and all are well known in the art; examples of particular techniques are described, without limitation, in Orita et al., Proc. Natl. Acad. Sci. USA 86: 2766–2770, 1989; Sheffield et al., Proc. Natl. Acad. Sci. USA 86: 232–236, 1989; Ausubel et al., supra).

In yet another approach, immunoassays may be used to detect or monitor p28 Bap31 expression in a biological sample. P28 Bap31-specific polyclonal or monoclonal antibodies (produced as described above) may be used in any standard immunoassay format (e.g., ELISA, Western blot, or RIA) to measure expression levels of p28 Bap31. These levels would be compared to p28 Bap31 levels in a unaffected biological sample of the same source and kind, with a decrease in p28 Bap31 production indicating a condition involving decreased apoptosis. Examples of immunoassays are described, e.g., in Ausubel et al., supra. Immunohistochemical techniques may also be utilized for p28 Bap31 detection. For example, a tissue sample may be obtained from a patient, sectioned, and stained for the presence of p28 Bap31 using an anti-p28 Bap31 antibody and any standard detection system (e.g., one which includes a secondary antibody conjugated to horseradish peroxidase). General guidance regarding such techniques may be found in the art (see, for example, Bancroft and Stevens (*Theory and Practice of Histological Technigues,* Churchill Livingstone, 1982, and Ausubel et al., supra).

In one preferred example, a combined diagnostic method may be employed that begins with an evaluation of p28 Bap31 protein production (for example, by immunological techniques or the protein truncation test (Hogerrorst et al., Nature Genetics 10: 208–212, 1995) and also includes a nucleic acid-based detection technique designed to identify more subtle p28 Bap31 mutations (for example, point mutations). As described above, a number of mismatch detection assays are available to those skilled in the art, and any preferred technique may be used. Mutations in p28 Bap31 may be detected that either result in loss of a normal level of p28 Bap31 expression or loss of normal p28 Bap31 biological activity. In a variation of this combined diagnostic method, p28 Bap31 biological activity is measured as apoptotic-inducing activity using any appropriate apoptosis assay system, or as a Bcl-2 interacting activity using a protein:protein interaction assay (e.g., the yeast two-hybrid system described above).

Mismatch detection assays also provide an opportunity to diagnose a p28 Bap31-mediated predisposition to diseases caused by an inappropriate amount of apoptosis. For example, a patient heterozygous for a p28 Bap31 mutation that induces a p28 Bap31 overexpression may show no clinical symptoms and yet possess a higher than normal probability of developing one or more types of neurodegenerative or myelodysplastic disorders, or having severe sequelae to an ischemic event. Likewise, an a-symptomatic patient found to be heterozygous for a p28 Bap31 mutation that induces a reduced level of p28 Bap31 or expression may have an increased risk of developing cancer. Given such a diagnosis, a patient may take precautions to minimize his exposure to adverse environmental factors (for example, UV exposure or chemical mutagens) and to carefully monitor his medical condition (for example, through frequent physical examinations). These types of p28 Bap31 diagnostic approaches may also be used to detect p28 Bap31 mutations in prenatal screens. The p28 Bap31 diagnostic assays described above may be carried out using any biological sample (for example, any biopsy sample or other tissue) in which p28 Bap31 is normally expressed. Identification of a mutant p28 Bap31 gene may also be assayed using these sources for test samples.

A mutation in either p28 Bap31, particularly as part of a diagnosis for predisposition to p28 Bap31-associated disease, may also be tested using a nucleic acid sample from any cell, for example, by mismatch detection techniques. Preferably, the nucleic acid sample is subjected to PCR amplification prior to analysis.

Preventative Anti-Apoptotic Therapy

In a patient diagnosed to be heterozygous for a p28 Bap31 mutation that increases p28 Bap31 expression and/or biological activity or to be susceptible to such a mutation, or a patient diagnosed with a degenerative disease (e.g., neurodegenerative disorders such as Huntington's or ALS diseases), or diagnosed as HIV positive, any of the above therapies may be administered prior to the occurrence of the disease phenotype. For example, the therapies may be provided to a patient who is HIV positive but does not yet show a diminished T cell count or other overt signs of AIDS. In particular, the HIV positive patient may be treated with compounds shown to decrease p28 Bap31 expression or decrease p28 Bap31 biological activity which may be administered by any standard dosage and route of administration (see above). Alternatively, gene therapy using an antisense p28 Bap31 mRNA expression construct may be undertaken to reverse or prevent the T cell defect prior to the development of AIDS.

The methods of the instant invention may be used to reduce or diagnose the disorders described herein in any mammal, for example, humans, domestic pets, or livestock. Where a non-human mammal is treated or diagnosed, the p28 Bap31 polypeptide, nucleic acid, or antibody employed is preferably specific for that species.

Characterization of p28 Bap31 Biological Activity and Intracellular Localization Studies The ability of p28 Bap31 to modulate apoptosis can be defined in in vitro systems in which alterations of apoptosis can be detected. Mammalian expression constructs carrying p28 Bap31 cDNAs, which are either full-length or truncated, may be introduced into cell lines such as KB, CHO, NIH 3T3, HL60, Rat-1, or Jurkat cells. In addition, SF9 insect cells may be used, in which case the p28 Bap31 genes are preferentially expressed using an insect baculovirus expression system. Following introduction of expression constructs carrying p28 Bap31 cDNAs encoding either full-length or truncated polypeptides, cells can be induced to undergo apoptosis by standard methods, which include serum withdrawal, or application of staurosporine, menadione (which induces apoptosis via free radical formation), or treatment with anti-Fas or anti-TNF-R1 antibodies. Preferably, human KB cells are transfected by calcium phosphate precipitation and induced to undergo apoptosis by infection with adenovirus type 5 lacking expression of E1B 19K (pm1716/2072). KB cells thus infected but either not transfected, or transfected with a vector that lacks a p28 Bap31 insert are used as a control. The ability of each p28 Bap31 construct to induce or inhibit apoptosis upon expression can be quantified by calculating the survival index of the cells, i.e., the ratio of surviving transfected cells to surviving control cells. These experiments can confirm the presence of apoptosis inducing activity of the full length p28 Bap31 protein and, as discussed below, can also be used to determine the functional regions of p28 Bap31. These assays may also be performed in combination with the application of additional compounds in order to identify compounds that modulate apoptosis via p28 Bap31.

OTHER EMBODIMENTS

In other embodiments, the invention includes any protein which is substantially identical to a mammalian p28 Bap31 polypeptides; such homologues include other substantially pure naturally-occurring mammalian p28 Bap31 proteins as well as allelic variants; natural mutants; induced mutants; nucleic acid sequences which encode proteins and also hybridize to the p28 Bap31 nucleic acid sequences under high stringency conditions (e.g., washing at 1×SSC at 65° C. with a probe length of at least 20 nucleotides) or, less preferably, under low stringency conditions (e.g., washing at 2×SSC at 40° C. with a probe length of at least 40 nucleotides); and proteins specifically bound by antisera directed to a p28 Bap31 polypeptide. The term also includes chimeric polypeptides that include a portion from p28 Bap31.

The invention further includes analogs of any naturally-occurring p28 Bap31 polypeptides. Analogs can differ from the naturally-occurring p28 Bap31 protein by amino acid sequence differences, by post-translational modifications, or by both. Analogs of the invention will generally exhibit at least 85%, more preferably 90%, and most preferably 95% or even 99% identity with all or part of a naturally occurring p28 Bap31 amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring p28 Bap31 polypeptide by alterations in the primary amino acid sequence. These include genetic variants, both natural and induced (for example, resulting from random mutagenesis by irradiation or exposure to ethanemethylsulfate (EMS) or by site-specific mutagenesis as described in Sambrook, et al., supra or Ausubel et al., supra). Also included are cyclized peptides, molecules, and analogs which contain residues other than L-amino acids, e.g., D-amino acids or non-naturally occurring or synthetic amino acids. In addition to full-length polypeptides, the invention also includes p28 Bap31 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of p28 Bap31 polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a p28 Bap31 nucleic acid or amino acid sequences in a sample to be diagnosed. Particularly useful p28 Bap31 fragments for this purpose include, without limitation, the amino acid fragments which bind Bcl-2 or Bcl-$X_L$, which are retained in p20, which are cleaved to create the p20 product, or which are located in the death domain.

All publications and patent applications mentioned in this specification are herein incorporated by reference to the same extent as if each independent publication or patent application was specifically and individually indicated to be incorporated by reference.

What is claimed is:

1. A method for identifying a compound that modulates apoptosis, said method comprising the steps of:
   (a) providing a cell having:
       (i) a reporter gene operably linked to a DNA-binding-protein recognition site;
       (ii) a first fusion gene capable of expressing a first fusion protein comprising a polypeptide covalently bonded to a polypeptide which is a binding moiety that is capable of specifically binding to said DNA-binding-protein recognition site; and
       (iii) a second fusion gene capable of expressing a second fusion protein comprising a polypeptide of a second protein covalently bonded to a gene activating moiety, wherein either said first polypeptide or said second polypeptide is human p28 Bap31 (SEQ ID NO: 1) or mouse p28 Bap31 (SEQ ID NO: 33) or a fragment of said human or mouse p28 Bap31, said fragment comprising a domain required for association of p28 Bap31 with pro-FLICE or a domain required for association of p28 Bap31 with Bcl-2 or Bcl-$X_L$;
   (b) exposing said cell to said compound; and
   (c) measuring reporter gene expression in said cell, a change in said reporter gene expression identifying said candidate compound as a compound that modulates apoptosis.

2. The method of claim 1, wherein said cell is a yeast cell.

3. The method of claim 1, wherein said first polypeptide or said second polypeptide is Bcl-2 or Bcl-$X_L$.

4. A method for identifying a compound that modulates apoptosis, said method comprising:
   (a) providing human p28 Bap31 (SEQ ID NO: 1) or mouse p28 Bap31 (SEQ ID NO: 33) or a fragment of said human or mouse p28 Bap31, said fragment comprising a domain required for association of p28 Bap31 with pro-FLICE or a domain required for association of p28 Bap31 with Bcl-2 or Bcl-$X_L$; and
   (b) contacting said polypeptide with a candidate compound and monitoring the level of p28 Bap31 biological activity, wherein a change in said level of p28 Bap31 biological activity in response to said candidate compound relative to the level of p28 Bap31 biological activity of said p28 Bap31 polypeptide not contacted with said candidate compound identifies said candidate compound as a compound that modulates apoptosis.

5. The method of claim 4, wherein said biological activity is cleavage of said p28 Bap31 polypeptide to produce a p20 product.

6. The method of claim 4, wherein said biological activity is formation of a complex with pro-FLICE.

7. The method of claim 4, wherein said biological activity is formation of a complex with a Bcl-2 protein.

8. The method of claim 7, wherein said Bcl-2 protein is Bcl-2 or Bcl-$X_L$.

9. The method of claim 4, wherein said biological activity is binding of said p28 Bap31 polypeptide by an antibody that preferentially binds to human p28 Bap31 (SEQ ID NO: 1) or mouse p28 Bap31 (SEQ ID NO: 33).

10. A method for identifying a compound that modulates apoptosis, said method comprising the steps of:
    (a) contacting a first polypeptide comprising human p28 Bap31 (SEQ ID NO: 1) or mouse p28 Bap31 (SEQ ID NO: 33) or a fragment of said human or mouse p28 Bap31, said fragment comprising a domain required for association of p28 Bap31 with pro-FLICE or a domain required for association of p28 Bap31 with Bcl-2 or Bcl-$X_L$ with a second polypeptide that interacts with said p28 Bap31 polypeptide such that said first polypeptide and said second polypeptide can form an interaction;
    (c) contacting said first polypeptide and said second polypeptide with a candidate compound; and
    (d) measuring said interaction of said first polypeptide and said second polypeptide, a change in said interaction of said first polypeptide and said second polypeptide in the presence of said candidate compound relative to an interaction of said first polypeptide and said second polypeptide not contacted with said candidate compound identifying said compound as a compound that modulates apoptosis.

11. The method of claim 1, 4, or 10, wherein said change is a decrease indicating said compound is useful for inhibiting apoptosis or said change is an increase indicating said compound is useful for increasing apoptosis.

12. The method of claim 4 or 10, wherein said contacting takes place in a cell-free system.

13. The method of claim 12, wherein said second polypeptide comprises Bcl-$X_L$, Bcl-2, or FLICE.

14. The method of claim 4 or 10, wherein said contacting takes place in a cell.

15. The method of claim 14, wherein said cell is from a human or a rodent.

16. The method of claim 14, wherein said cell is a mammalian cell.

17. The method of claim 14, wherein said cell is a yeast cell.

18. The method of claim 1, 4, or 10, wherein said p28 Bap31 polypeptide is an amino terminal fragment of human p28 Bap31 (SEQ ID NO: 1) or mouse p28 Bap31 (SEQ ID NO: 33).

19. The method of claim 18, wherein said amino terminal fragment is a p20 fragment of human p28 Bap31 (SEQ ID NO: 1) or mouse p28 Bap31 (SEQ ID NO: 33).

20. The method of claim 10, wherein said second polypeptide is Bcl-2 or Bcl-$X_L$.

21. The method of claim 9, wherein said antibody is detectably-labelled.

* * * * *

UNITED STATES PATENT AND TRADEMARK OFFICE
CERTIFICATE OF CORRECTION

PATENT NO.    : 6,607,880 B1
DATED         : August 19, 2003
INVENTOR(S)   : Shore et al.

It is certified that error appears in the above-identified patent and that said Letters Patent is hereby corrected as shown below:

Column 17,
Line 65, "Hemagglutinen" should be -- Hemagglutinin --.

Column 18,
Line 36, "imunoprecipitation" should be -- immunoprecipitation --.
Line 37, "transfered" should be -- transferred --.

Column 24,
Line 43, "10μμg/ml" should be -- 10μg/ml --.

Column 33,
Line 51, "which ws co-expressed" should be -- which was co-expressed --.

Column 34,
Line 10, "Phorphorimager" should be -- Phosphorimager --.

Signed and Sealed this

Twenty-sixth Day of October, 2004

JON W. DUDAS
*Director of the United States Patent and Trademark Office*